United States Patent
Tseng et al.

(10) Patent No.: US 9,682,044 B2
(45) Date of Patent: Jun. 20, 2017

(54) METHODS OF PROCESSING FETAL SUPPORT TISSUES, FETAL SUPPORT TISSUE POWDER PRODUCTS, AND USES THEREOF

(75) Inventors: Scheffer Tseng, Pinecrest, FL (US); Ek Kia Tan, Miami, FL (US); Lorraine Chua, Miami, FL (US)

(73) Assignee: TISSUETECH, INC., Doral, FL (US)

( * ) Notice: Subject to any disclaimer, the term of this patent is extended or adjusted under 35 U.S.C. 154(b) by 378 days.

(21) Appl. No.: 14/125,301

(22) PCT Filed: Jun. 8, 2012

(86) PCT No.: PCT/US2012/041685
§ 371 (c)(1),
(2), (4) Date: Apr. 11, 2014

(87) PCT Pub. No.: WO2012/170905
PCT Pub. Date: Dec. 13, 2012

(65) Prior Publication Data
US 2014/0147511 A1    May 29, 2014

Related U.S. Application Data

(60) Provisional application No. 61/495,860, filed on Jun. 10, 2011.

(51) Int. Cl.
| A61K 9/19 | (2006.01) |
| A61K 35/50 | (2015.01) |
| A61K 35/51 | (2015.01) |
| A61K 35/48 | (2015.01) |

(52) U.S. Cl.
CPC ............... *A61K 9/19* (2013.01); *A61K 35/48* (2013.01); *A61K 35/50* (2013.01); *A61K 35/51* (2013.01)

(58) Field of Classification Search
None
See application file for complete search history.

(56) References Cited

U.S. PATENT DOCUMENTS

| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,909,816 A | 9/1975 | Teeters |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,100,022 A | 7/1978 | Ogasa et al. |
| 4,120,649 A | 10/1978 | Schechter |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory |
| 4,327,725 A | 5/1982 | Cortese et al. |
| 4,347,841 A | 9/1982 | Benyo et al. |
| 4,361,552 A | 11/1982 | Baur, Jr. |
| 4,405,616 A | 9/1983 | Rajadhyaksha |
| 4,476,116 A | 10/1984 | Anik |
| 4,599,084 A | 7/1986 | Nashef |
| 4,599,226 A | 7/1986 | Fox, Jr. et al. |
| 4,624,848 A | 11/1986 | Lee |
| 4,801,586 A | 1/1989 | Minaskanian et al. |
| 4,829,000 A | 5/1989 | Kleinman et al. |
| 4,861,764 A | 8/1989 | Samour et al. |
| 4,871,549 A | 10/1989 | Ueda et al. |
| 4,886,783 A | 12/1989 | Minaskanian et al. |
| 4,968,509 A | 11/1990 | Radebaugh et al. |
| 4,983,396 A | 1/1991 | Bodor et al. |
| 4,997,425 A | 3/1991 | Shioya et al. |
| 5,002,071 A | 3/1991 | Harrell |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,118,845 A | 6/1992 | Peck et al. |
| 5,135,915 A | 8/1992 | Czarniecki et al. |

(Continued)

FOREIGN PATENT DOCUMENTS

| CN | 1193515 A | * | 9/1998 |
| CN | 1203794 A | * | 1/1999 |

(Continued)

OTHER PUBLICATIONS

Co-pending U.S. Appl. No. 14/848,143, filed Sep. 8, 2015.
Co-pending U.S. Appl. No. 14/848,148, filed Sep. 8, 2015.
Co-pending U.S. Appl. No. 14/848,153, filed Sep. 8, 2015.
Co-pending U.S. Appl. No. 14/880,135, filed Oct. 9, 2015.
Co-pending U.S. Appl. No. 14/886,946, filed Oct. 19, 2015.
Co-pending U.S. Appl. No. 14/996,051, filed Jan. 14, 2016.
Diaz-Prado et al. Potential use of the human amniotic membrane as a scaffold in human articular cartilage repair. Cell Tissue Bank 11:183-195 (2010).
Hatano et al. Transplantation of amniotic membrane and limbal autograft in the treatment of recurrent pterygium. Clinical Ophthalmology 50(6):1101-1104 (1996) (English Abstract).
Hilmy et al. Physical and chemical properties of freeze-dried amnio-chorion membranes sterilized by γ irradiation. Atom Indonesia 13(2):1-3 (1987) Abstract only.

(Continued)

*Primary Examiner* — Qiuwen Mi
(74) *Attorney, Agent, or Firm* — Wilson Sonsini Goodrich & Rosati

(57) ABSTRACT

Disclosed herein, are methods of preparing fetal support tissue powders. Further disclosed herein, are methods of using the fetal support tissue powder product.

6 Claims, 25 Drawing Sheets

(56) References Cited

U.S. PATENT DOCUMENTS

| | | | |
|---|---|---|---|
| 5,192,744 | A | 3/1993 | Bouck et al. |
| 5,196,410 | A | 3/1993 | Francoeur et al. |
| 5,229,135 | A | 7/1993 | Philippon et al. |
| 5,260,068 | A | 11/1993 | Chen |
| 5,260,069 | A | 11/1993 | Chen |
| 5,294,446 | A | 3/1994 | Schlameus et al. |
| 5,323,907 | A | 6/1994 | Kalvelage |
| 5,336,168 | A | 8/1994 | Sibalis |
| 5,352,668 | A | 10/1994 | Burgeson et al. |
| 5,437,287 | A | 8/1995 | Phillips et al. |
| 5,456,923 | A | 10/1995 | Nakamichi et al. |
| 5,461,140 | A | 10/1995 | Heller et al. |
| 5,508,040 | A | 4/1996 | Chen |
| 5,516,527 | A | 5/1996 | Curatolo |
| 5,554,593 | A | 9/1996 | Nakaya et al. |
| 5,567,441 | A | 10/1996 | Chen |
| 5,622,721 | A | 4/1997 | Dansereau et al. |
| 5,665,378 | A | 9/1997 | Davis et al. |
| 5,686,105 | A | 11/1997 | Kelm et al. |
| 5,700,410 | A | 12/1997 | Nakamichi et al. |
| 5,837,280 | A | 11/1998 | Kenealy et al. |
| 5,837,284 | A | 11/1998 | Mehta et al. |
| 5,840,329 | A | 11/1998 | Bai |
| 5,869,090 | A | 2/1999 | Rosenbaum |
| 5,932,545 | A | 8/1999 | Henkin et al. |
| 5,977,175 | A | 11/1999 | Lin |
| 6,152,142 | A | 11/2000 | Tseng |
| 6,203,755 | B1 | 3/2001 | Odland |
| 6,326,019 | B1 | 12/2001 | Tseng et al. |
| 6,391,452 | B1 | 5/2002 | Antonsen et al. |
| 6,465,014 | B1 | 10/2002 | Moroni et al. |
| 6,521,179 | B1 | 2/2003 | Girardot et al. |
| 6,632,648 | B1 | 10/2003 | Kampinga et al. |
| 6,923,983 | B2 | 8/2005 | Morgan et al. |
| 6,929,801 | B2 | 8/2005 | Klose et al. |
| 6,932,983 | B1 | 8/2005 | Straub et al. |
| 6,946,144 | B1 | 9/2005 | Jordan |
| 7,476,221 | B2 | 1/2009 | Sun et al. |
| 7,494,802 | B2 | 2/2009 | Tseng et al. |
| 8,071,135 | B2 | 12/2011 | Liu et al. |
| 8,153,162 | B2 | 4/2012 | Tseng |
| 8,182,840 | B2 | 5/2012 | Tseng |
| 8,182,841 | B2 | 5/2012 | Tseng |
| 8,187,639 | B2 | 5/2012 | Tseng |
| 8,372,437 | B2 | 2/2013 | Daniel |
| 8,372,438 | B2 | 2/2013 | Daniel et al. |
| 8,420,126 | B2 | 4/2013 | Tseng et al. |
| 8,440,235 | B2 | 5/2013 | Tseng et al. |
| 8,455,009 | B2 | 6/2013 | Tseng et al. |
| 8,460,714 | B2 | 6/2013 | Tseng et al. |
| 8,486,374 | B2 | 7/2013 | Tamarkin et al. |
| 8,741,265 | B2 | 6/2014 | Tamarkin et al. |
| 2001/0041684 | A1 | 11/2001 | Lezdey |
| 2002/0192272 | A1 | 12/2002 | Popp |
| 2003/0064093 | A1 | 4/2003 | Jordan |
| 2003/0180181 | A1 | 9/2003 | Greib et al. |
| 2004/0048796 | A1 | 3/2004 | Hariri et al. |
| 2004/0057938 | A1 | 3/2004 | Ghinelli |
| 2004/0126323 | A1 | 7/2004 | Shevchuk et al. |
| 2005/0064391 | A1 | 3/2005 | Segal et al. |
| 2006/0153928 | A1* | 7/2006 | Kinoshita ............... A61L 15/40 424/582 |
| 2008/0069895 | A1 | 3/2008 | Liu et al. |
| 2008/0102135 | A1 | 5/2008 | Ollivier |
| 2008/0131522 | A1 | 6/2008 | Liu et al. |
| 2008/0193554 | A1 | 8/2008 | Dua et al. |
| 2008/0299087 | A1* | 12/2008 | Tseng ..................... A61K 35/48 424/93.7 |
| 2009/0226499 | A1 | 9/2009 | Wisniewski et al. |
| 2010/0104539 | A1 | 4/2010 | Daniel et al. |
| 2011/0212158 | A1 | 9/2011 | Tom et al. |
| 2012/0141595 | A1 | 6/2012 | Tseng et al. |
| 2012/0189583 | A1 | 7/2012 | Liu et al. |
| 2013/0156863 | A1 | 6/2013 | Tseng et al. |
| 2013/0195992 | A1 | 8/2013 | Tseng et al. |
| 2013/0195993 | A1 | 8/2013 | Tseng et al. |
| 2013/0195994 | A1 | 8/2013 | Tseng et al. |
| 2013/0280344 | A1 | 10/2013 | Tseng et al. |
| 2013/0344163 | A1 | 12/2013 | Tseng et al. |
| 2014/0067058 | A1 | 3/2014 | Koob et al. |
| 2015/0342998 | A1 | 12/2015 | Tseng et al. |
| 2016/0120912 | A1 | 5/2016 | Tseng |

FOREIGN PATENT DOCUMENTS

| | | |
|---|---|---|
| EP | 0669138 | 8/1995 |
| EP | 1604695 | 12/2005 |
| JP | 74043153 B | 11/1974 |
| JP | H01256967 A | 10/1989 |
| KR | 2001-098716 A | 11/2001 |
| WO | WO98-37903 | 9/1998 |
| WO | WO-0180844 A2 | 11/2001 |
| WO | WO03-77794 | 9/2003 |
| WO | WO-03097809 A2 | 11/2003 |
| WO | WO2004-026244 | 1/2004 |
| WO | WO2004-060388 | 7/2004 |
| WO | WO2007-038686 | 4/2005 |
| WO | WO2005-60988 A1 | 7/2005 |
| WO | WO2006-094247 | 9/2006 |
| WO | WO-2008060377 A2 | 5/2008 |
| WO | WO2011-031489 | 3/2011 |
| WO | WO-2012170905 A1 | 12/2012 |
| WO | WO-2013032938 A1 | 3/2013 |
| WO | WO-2013103413 A1 | 7/2013 |
| WO | WO-2015187812 A1 | 12/2015 |
| WO | WO-2016010984 A2 | 1/2016 |
| WO | WO-2016073667 A1 | 5/2016 |

OTHER PUBLICATIONS

Hori. Amniotic Membrane Transplantation and Immune Reaction. Folia Ophthalmologica Japonica 56(9):722-727 (2005) (English Abstract).

Liu et al. E-cadherin engagement stimulates proliferation via Rac1. Journal of Cell Biology, 2006, 173(3):431-441.

Tan et al. Structural and Biological Comparison of Cryopreserved and Fresh Amniotic membrane Tissues. Journal Biomaterial and Tissue Engineering 4:379-388 (2014).

U.S. Appl. No. 13/322,896 Office Action dated Jul. 6, 2015.
U.S. Appl. No. 13/322,896 Office Action mailed Oct. 22, 2014.
U.S. Appl. No. 13/704,231 Office Action dated Feb. 11, 2016.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.
U.S. Appl. No. 13/802,204 Office Action dated Jan. 22, 2016.
U.S. Appl. No. 13/802,264 Office Action dated Jul. 16, 2015.
U.S. Appl. No. 13/802,264 Office Action mailed Nov. 28, 2014.
U.S. Appl. No. 13/802,359 Office Action dated Dec. 10, 2014.
U.S. Appl. No. 13/802,447 Office Action dated Dec. 15, 2014.

Azuara-Blanco et al. Amniotic Membrane Transplantation for Ocular Surface Reconstruction. Invest. Ophthalmol. Vis. Sci. 39(4):S428 (1998).

Azuara-Blanco et al. Amniotic Membrane Transplantation for Ocular Surface Reconstruction. Br. J. Ophthalmol. 83(4):399-402 (1999).

Badawy et al. Evaluation of Tissue Healing and Adhesion Formation After an Intraabdominal Amniotic Membrane Graft in the Rat. J. Reproductive Med. 34:198 (1989).

Bae et al. Characterization of the Promoter Region of the Human Transforming Growth Factor-β Type II Receptor Gene,. J. Biol. Chem. 270(49):29460-29468 (1995).

Barton et al. Amniotic Membrane Transplantation in Glaucoma Surgery. Invest Optamol Vis Sci 38:S473 (1997).

Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).

(56) References Cited

OTHER PUBLICATIONS

Border et al. Transforming Growth Factor-β in Disease: The Dark Side of Tissue Repair. J. Clin. Invest. 90:1-7 (1992).
Budenz et al. Amniotic Membrane Transplantation for Repair of Leaking Glaucoma Filtering Blebs. Am. J. Ophthalmol. 130:580-588 (2000).
Chen et al. Amniotic Membrane Transplantation for Severe Neurotrophic Corneal Ulcers. Br. J. Ophthalmol. 84:826-833 (2000).
Chen et al. Recombinant Adenovirus Coexpressing Covalent Peptide/MHC Class II Complex and B7-1: In Vitro and In Vivo Activation of Myelin Basic Protein-Specific T Cells, J. Immunol. 167:1297-1305 (2001).
Chen et al. Functions of hyaluronan in wound repair, Wound Rep. Reg. 7:79-89 (1999).
Cho et al. Conjunctival Epithelial Cells Cultured on Human Amniotic Membrane Fail to Transdifferentiate into Corneal Epithelial-type Cells. Cornea, 18:216-224 (1999).
Cho et al. Conjunctival Epithelial Cells Cultured on Human Amniotic Membrane Do Not Transdifferentiate into Corneal Epithelial Type Cells. Invest. Ophthalmol. Vis. Sci. 39(4):S428 (1998).
Choi et al. Effect of the Application of Human Amniotic Membrane on Rabbit Corneal wound Healing After Excimer Laser Photorefractive Keratectomy. Cornea, 17:389-395 (1998).
Day et al. Hyaluronan cross-linking: a protective mechanism in inflammation? Trends in Immunology 26(12):637-643 (2005).
Derotth. Plastic Repair of Conjunctival Defects with Fetal Membranes. Archives of Opthamology 23:522-525 (1940).
Derynk et al. TGF-β receptor signaling, Biochem. Biophys. Acta. 1333:F105-F150 (1997).
Dua et al. Amniotic Membrane Transplantation. Br. J. Opthalmol. 83:748-752 (1999).
EP13163155.8 Extended Search Report mailed Oct. 21, 2013.
EP06804232.4 Search Report mailed May 10, 2010.
EP10815849.4 Extended Search Report mailed Mar. 31, 2014.
Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).
Fortunato et al. Interleukin-10 inhibition of interleukin-6 in human amniochorionic membrane: Transcriptional regulation. Am. J. Obstet. Gynecol. 175:1057-1065 (1996).
Fortunato et al. The effect of transforming growth factor and interleukin-10 on interleukin-8 release by human amniochorion may regulate histologic chorioamnionitis. Am. J. Obstet. Gynecol. 179(3):794-799 (1998).
Franch et al. Human Amniotic Membrane Transplantation. Invest. Ophthalmol. Vis. Sci. 39(4):S90 (1998).
Fries et al. Intera-a-inhibitor, hyaluronan and inflammation, Acta Biochim. Polonica 50(3):735-742 (2003).
Fujishima et al. Trabeculectomy With the Use of Amniotic Membrane for Uncontrolled Glaucoma, Ophthalmic. Surg. Lasers 29:428-431 (1998).
Fukuda et al. Differential Distribution of Subchains of the Basement Membrane Components Type IV Collagen and Laminin Among the AMniotic Membrane, Cornea, and Conjunctiva. Cornea 18:73-79 (1999).
Gabbiani. The myofibroblast in wound healing and fibrocontractive diseases. J. Pathol. 200:500-503 (2003).
Grande. Role of Transforming Growth Factor-β in Tissue Injury and Repair. Proc. Soc. Exp. Biol. Med. 214:27-40 (1997).
Guo. Carbopol® Polymers for Pharmaceutical Drug Delivery Applications. Drug Delivery Technology 3(6):1-4 (2003).
Hales et al. TGF-β-1 induces lens cells to accumulate a-smooth muscle actin, a marker for subcapsular cataracts. Curr. Eye Res. 13:885-890 (1994).
Hanada et al. Regulation of cytokine signaling and inflammation. Cytokine & Growth Factor Reviews 13(4-5):413-421 (2002).
Hao et al. Identification of Antiangiogenic and Antiinflammatory Proteins in Human Amniotic Membrane. Cornea 19(3):348-352 (2000).
He et al. Biochemical Characterization and Function of Complexes Formed by Hyaluronan and the Heavy Chains of Inter-a-inhibitor (HC-HA) Purified from Extracts of Human Amniotic Membrane, J. Biol. Chem. 284(30):20136-20146 (2009).
He et al. A simplified system for generating recombinant adenoviruses, PNAS USA 95:2509-2514 (1998).
Heiligenhaus et al. Improvement of HSV-1 Necrotizing Keratitis with Amniotic Membrane Transplantation, Invest. Ophthalmol. Vis. Sci. 42(9):1969-1974 (2001).
Howes et al. Receptor for Advanced Glycation End Products and Age-Related Macular Degeneration. Invest. Ophthal. Vis. Sci. 45(10):3713-3720 (2004).
Jester et al. Corneal Stromal Wound Healing in Refractive Surgery: the Role of Myofibroblasts. Prog. Retin. Eye Res. 18(3):311-356 (1999).
Jester et al. Induction of α-Smooth Muscle Actin Expression and Myofibroblast Transformation in Cultured Cornea Keratocytes. Cornea 15(5):505-516 (1996).
Keelan et al. Activin a Exerts both Pro- and -Anti-inflammatory Effectson Human Term Gestational Tissues. Placenta 31:38-43 (2000).
Kim et al. Temporary Amniotic Membrane Graft Promotes Healing and Inhibits Protease Activity in Corneal Wound Induced by Alkali Burn in Rabbits. Invest. Ophthalmol. Vis. Sci. 39(4):S90 (1998).
Kim et al. Amniotic Membrane Patching Promotes Healing and Inhibits Protease Activity on Wound Healing Following Acute Corneal Alkali Burns. Exp. Eye Res. 70:329-337 (1998).
Kim et al. Clinical Uses of Human Amniotic Membrane for Ocular Surface Diseases. In: Advances in Corneal Research, Lass, J.H. ed. (NY: Plenum Press), pp. 117-134 (1997).
Kim et al. The Effects on Inhibition of Corneal Neovascularization After Human Amniotic Membrane Transplantation in Severely Damaged Rabbit Corneas. Korean J. Ophthalmol. 9:32-46 (1995).
Kim et al. Transportation of Preserved Human Amniotic Membrane for Surface Reconstruction in Severely Damaged Rabbit Corneas. Cornea 15:473-84 (1995).
Klen. Influence of Ionizing Sterilization on the Permeability of Human Chorio-Amniotic, Dermo-Epidermal and Fascial Grafts. Res. Exp. Med. 167(1):15-21 (1976).
Koizumi et al. Amniotic Membrane as a Substrate for Cultivating Limbal Corneal Epithelial Cells for Autologous Transplantation in Rabbits. Cornea, 19:65-71(2000).
Koizumi et al. Cultivation of Corneal Epithelial Cells on Intact and Denuded Human Amniotic Membrane. Invest. Ophthalmol. Vis. Sci. 41:2506-2513 (2000).
Koizumi et al. Growth Factor mRNA and Protein in Preserved Human Amniotic Membrane. Curr. Eye Res. 20:173-177 (2000).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Kruse et al. Cryoperserved Human Amniotic Membrane for Ocular Surface Reconstruction. Graefe's Arch. Clin. Exp. Ophthalmol. 238:68-75 (2000).
Kruse et al. Multilayer Amniotic Membrane Transplantation for Reconstruction of Deep Corneal Ulcers. Ophthalmology 106:1504-1511(1999).
Lawrence, D.A., Transforming Growth Factor-β: a general review. Eur. Cytokine Netw. 7:363-374 (1996).
Lee et al. An Agarose Gel Electrophoretic Method for Analysis of Hyaluronan Molecular Weight Distribution. Anal. Biochem. 219:278-287 (1994).
Lee et al Amniotic Membrane Transplantation for Persistent Epithelial Defects with Ulceration. Am. J. Ophthalmol. 123:303-312 (1997).
Lee et al. Suppression of TGF-β signaling in both normal conjuctival fibroblasts and pterygial body fibroblasts by amniotic membrane. Curr. Eye Res. 20(4):325-334 (2000).
Li et al. An Experimental Study of the Effects of Human Amniotic Membrane on Human Retinal Pigment Epithelial Cell Proliferation

(56) References Cited

OTHER PUBLICATIONS in vitro. Acta Acadamiae Medicinae Militaris Tertia, 2003. 25(5):407-409 (with English Abstract).
Lieberman et al. Pharmaceutical Dosage Forms. 2 Ed. 1:209-214 (1990).
Liu et al. Biocompatibility and stability of disulfide-corsslinked hyaluronan films. Biomaterials 26(23):4737-4746 (2005).
Logan et al. Decorin Attenuates Gliotic Scar Formation in the Rat Cerebral Hemisphere. Exp. Neurol. 159:504-510 (1999).
Ma et al. Amniotic Membrane Graft for Primary Pterygium: Comparison with Conjuctival Autograft and Topical Mitomycin C Treatment. Br. J. Ophthalmol. 84:973-978 (2000).
Marek et al. TGF-β-(transforming growth factor-β) in chronic inflammatory conditions-a new diagnostic and prognostic marker? Med. Sci. Monitl 8(7):RA145-RA151 (2002).
Massague et al. Controlling TGF-β signaling. Genes and Development 14:627-644 (2000).
Meller. Conjunctival Epithelial Cell Differentiation on Amniotic Membrane. Invest. Ophthalmol. Vis. Sci. 40:878-886 (1999).
Meller et al. Amniotic Membrane Transplantation for Acute Chemical or Thermal Burns. Ophthalmology. 107:980-990 (2000).
Meller et al. Amniotic Membrane Transplantation for Symptomatic Conjunctivochalasis Refractory to Medical Treatments. Cornea 19:796-803 (2000).
Meller et al. In Vitro Conjunctival Epithelial Differentiation on Preserved Human Amniotic Membrane. Invest. Ophthalmol. Vis. Sci. 39(4):S428 (1998).
Milner et al. TSG-6: a multifunctional protein associated with inflammation, J. Cell Sci. 116(10):1863-1873 (2003).
Moller-Pedersen et al. Neutralizing antibody to TGF-β modulates stromal fibrosis but not regression of photoablative effect following PRK, Curr. Eye Res. 17:736-747 (1998).
Monteleone et al. SMAD7 in TGF-b-mediated negative regulation of gut inflammation. Trends in Immunology 25(10):513-517 (2004).
Mukhopadhyay et al. Two distinct populations of tumor necrosis factor-stimulated gene-6 protein in the extracellular matrix of expanded mouse cumulus cell-oocyte complexes. Archives of Biochemistry and Biophysics 394(2):173-181 (2001).
Na et al. Analysis of Human Amniotic Membrane Components as Proteinase Inhibitors for Development of Therapeutic Agent of Recalcitrant Keratitis. Invest. Ophthalmol. Vis. Sci. 39(4):S90 (1998).
Na et al. Analysis of Human Amniotic Membrane Components as Proteinase Inhibitors for Development of Therapeutic Agent for Recalcitrant Keratitis. Trophoblast Res. 13:453-466 (1999).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Ochsner et al. Decreased expression of tumor necrosis factor-alpha-stimulated gene 6 in cumulus cells of the cyclooxygenase2 and EP2 null mice. Endocrinology 144: 1008-1019 (2003).
Oikawa et al. Inhibition of Angiogenesis by 15-Deoxyspergualin. J. Antibiotics 44(9):1033-1035 (1991).
Park et al. Modulation of Acute Inflammation and Keratocyte Death by Suturing, Blood and Amniotic Membrane in PRK. Invest. Ophthalmol. Vis. Sci. 41:2906-2914 (2000).
Park et al. Temperature Cooling Reduces Keratocyte Death in Excimer Laser Ablated Corneal and Skin Wounds. Invest. Ophthalmol. Vis. Sci. 39(4):S449 (1998).
PCT/US06/37906 International Preliminary Report on Patentability mailed Apr. 1, 2008.
PCT/US06/37906 International Search Report and Written Opinion mailed Jul. 11, 2007.
PCT/US98/03665 International Search Report mailed Jun. 23, 1998.
PCT/US10/46675 International Preliminary Report on Patentability mailed Feb. 28, 2012.
PCT/US10/46675 International Search Report and Written Opinion mailed May 30, 2011.
PCT/US2011/042679 International Preliminary Report on Patentability mailed Jan. 8, 2013.
PCT/US2011/042679 International Search Report and Written Opinion mailed Mar. 9, 2012.
Petraglia et al. Inhibin and Activin in Human Fetal Membranes: Evidence of a Local Effect on Prostaglandin Release. J. Clin. Endocrinol. Metab. 77(2):542-548 (1993).
Pires et al. Amniotic Membrane Transplantation or Limbal Conjuctival Autograft for Limbal Stem Cell Deficiency Induced by 5-fluorouracil in Glaucome Surgeries. Cornea 19:284-287 (2000).
Pires et al. Amniotic Membrane Transplantation for Symptomatic Bullous Keratopathy. Arch. Ophthalmol. 117(10):1291-1297 (1999).
Prabhasawat et al. Impression Cytology Study of Epithelial Phenotype of Ocular Surfaces Reconstructed by Preserved Human Amniotic Membrane. Arch Opthamol. 115:1360-1367 (Nov. 1997).
Prabhasawat et al. Comparison of Conjunctival Autografts, Amniotic Membrane Grafts, and Primary Closure for Pterygium Excision. Ophthalmology 104:974-985 (1997).
Riley et al. Production of inhibin forms by the fetal membranes, decidua, placenta and fetus at parturition. Hum. Reprod. 15:578-583 (2000).
Rodriguez-Ares et al. Repair of Scleral Perforation with Preserved Scleral and Amniotic Membrane in Marfan's Syndrome. Ophthalmic Surg. Lasers 30(6):485-487 (1999).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-β1 in Quiescent Human Breast Gland Fibroblasts. Lab. Invest. 68:696-707 (1993).
Rovere et al. The long pentraxin PTX3 binds to apoptotic cells and regulates their clearance by antigen-presenting dendritic cells. Blood 96(13):4300-4306 (2000).
Sato et al. Role of Growth Factors for Ocular Surface Reconstruction After Amniotic Membrane Transplantation. Invest. Ophthalmol. Vis. Sci. 39(4):S428 (1998).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β. Lancet 339:213-214 (1992).
Shimazaki et al. Amniotic Membrane Transplantation for Ocular Surface Reconstruction in Patients with Chemical and Thermal Burns. Ophthalmology. 104(12):2068-2076 (1997).
Shimazaki et al. Transplantation of Amniotic Membrane and Limbal Autograft for Patients with Recurrent Pterygium Associated with Symblepharon. Br. J. Ophthalmol. 82(3):235-240 (1998).
Singh et al. Encyclopedia of Pharmaceutical Technology. 2nd ed., pp. 751-753 (2002).
Solomon et al. Suppression of Interleukin la and interleukin 1b in human limbal epithelial cells cultured on the amniotic membrane stromal matrix. Br. J. Ophthalmol 85:444-449 (2001).
Sorsby Amniotic Membrane Grafts in Burns. In: Modern Trends in Ophthalmology. Sorsby, A. ed. (NY: Paul B. Hoeber, Inc.), pp. 504-510 (1947).
Sorsby et al. Amniotic Membrane Grafts in Caustic Burns of the Eye (Burns of the Second Degree). Br. J. Opthamology 30:337-345 (1946).
Sorsby et al. Further Experience with Amniotic Membrane Grafts in Caustic Burns of the Eye. Br. J. Opthamology 31:409-18 (1947).
Taylor et al. Rate of Re-Epithelization Following Amnionic Membrane Transplantation. Invest. Ophthalmol. Vis. Sci. 39(4):S1038 (1998).
Travis et al. Hyaluronan Enhances Contraction of Collagen by Smooth Muscle BCells and Adventitial Fibroblasts Role of CD44 and Implications for Constrictive Remodeling, Cir. Res. 88:77-83 (2001).
Trelford. The Amnion in Surgery, Past and Present. Am J. Obstet. Gynecol 134:833 (1979).

(56) References Cited

OTHER PUBLICATIONS

Tsai. Corneal Surfaces Reconstruction by Amniotic Membrane with Cultivated Autologous Limbo-Corneal Epithelium. Invest. Ophthalmol. Vis. Sci. 39(4):S429 (1998).
Tsai et al. Reconstruction of Damaged Corneas by Transplantion of Autologous Limbal Epithelial Cells. N. Eng. J. Med. 343:86-93 (2000).
Tseng et al. Down-regulation of TGF-.beta.1, .beta.2, .beta.3 and TGF-.beta. Receptor II Expression in Human Corneal Fibroblasts by Amniotic Membrane. Invest. Ophthalmol. Vis. Sci. 39(4):S428 (1998).
Tseng et al. Amniotic Membrane Transplantation for Conjunctival Surface Reconstruction. Am. J. Opthamol. 124:765-774 (Dec. 1997).
Tseng et al. How Does Amniotic Membrane Work? Ocular Surface J. 2(3):177-187 (2004).
Tseng et al Amniotic Membrane Transplantation With or Without Limbal Allografts for Corneal Surface Reconstruction in Patients With Limbal Stem Cell Deficiency. Arch. Ophthalmol. 116:431-441 (1998).
Tseng et al. Suppression of Transforming Growth Factor-Beta Isoforms, TGF-β Receptor Type II, and Myofibroblast Differentiation in Cultured Human Corneal and Limbal Fibroblasts by Amniotic Membrane Matrix. J. Cell Physiol., 179:325-335 (1999).
Tsubota et al. Surgical Reconstruction of the Ocular Surface in Advanced Ocular Cicatricial Pemphigoid and Stevens-Johnson Syndrome. Am J. Opthamology 122:38-52 (1996).
U.S. Appl. No. 09/027,109 Notice of Allowance mailed Jul. 5, 2000.
U.S. Appl. No. 09/027,109 Office Action mailed Dec. 7, 1999.
U.S. Appl. No. 09/027,109 Office Action mailed Jun. 5, 2000.
U.S. Appl. No. 11/528,902 Notice of Allowance mailed Mar. 7, 2012.
U.S. Appl. No. 11/528,902 Office Action mailed Jan. 27, 2011.
U.S. Appl. No. 11/528,902 Office Action mailed Dec. 16, 2009.
U.S. Appl. No. 11/528,902 Office Action mailed Apr. 2, 2009.
U.S. Appl. No. 11/528,902 Office Action mailed Sep. 8, 2010.
U.S. Appl. No. 11/528,980 Notice of Allowance mailed Feb. 23, 2012.
U.S. Appl. No. 11/528,980 Office Action mailed Jan. 10, 2011.
U.S. Appl. No. 11/528,980 Office Action mailed Oct. 15, 2010.
U.S. Appl. No. 11/528,980 Office Action mailed Nov. 13, 2008.
U.S. Appl. No. 11/528,980 Office Action mailed Aug. 11, 2009.
U.S. Appl. No. 11/529,658 Notice of Allowance mailed Mar. 8, 2012.
U.S. Appl. No. 11/529,658 Office Action mailed Jan. 27, 2011.
U.S. Appl. No. 11/529,658 Office Action mailed Dec. 16, 2009.
U.S. Appl. No. 11/529,658 Office Action mailed Apr. 3, 2009.
U.S. Appl. No. 11/529,658 Office Action mailed Sep. 3, 2010.
U.S. Appl. No. 11/535,924 Notice of Allowance mailed Mar. 20, 2012.
U.S. Appl. No. 11/535,924 Office Action mailed Jan. 31, 2011.
U.S. Appl. No. 11/535,924 Office Action mailed Dec. 16, 2009.
U.S. Appl. No. 11/535,924 Office Action mailed Mar. 31, 2009.
U.S. Appl. No. 11/535,924 Office Action mailed Sep. 8, 2010.
U.S. Appl. No. 13/345,840 Office Action mailed Aug. 21, 2012.
Verbeek et al. Induction of alpha-smooth muscle actin expression in cultured human brain pericytes by transforming growth factor-beta 1. Am. J. Pathol. 144:372-382 (1994).
Wang et al. Corneal Haze is Reduced by Amniotic Membrane Matrix in Excimer Laser Photoablation in Rabbits. Invest Opthamol Vis Sci 38:S405 (1997).
Yamaguchi et al. Negative regulation of transforming growth factor-β by the proteoglycan decorin. Nature 346(6281):281-284 (1990).
Yokomori et al. Advantages and Pitfalls of Amnion Inversion Repair for the Treatment of Large Unruptured Omphalocele: Results of 22 Cases. Journal of Pediatric Surgery 23:882-884 (1992).
Ahmed et al. Expression and localization of alphavbeta6 integrin in extraplacental fetal membranes: possible role in human parturition. Mol Hum Reprod 10(3):173-179 (2004).

Kuznetsova et al. The N-terminal module of thrombospondin-1 interacts with the link domain of Tsg-6 and enhances its covalent association with the heavy chains of inter-alpha-trypsin inhibitor. J Biol Chem 280:30899-30908 (2005).
Saltzman. Drug Administration and Drug Effectiveness. Chapter 2. Drug Delivery-Engineering Principles for Drug Therapy. Oxford Press. p. 9-19 (2001).
Sur et al. Anti-inflammatory and anti-platelet aggregation activity of human placental extract. Acta Pharmacol Sin 24(2):187-192 (2003).
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
U.S. Appl. No. 13/322,896 Office Action dated Oct. 4, 2016.
U.S. Appl. No. 13/802,204 Office Action dated Oct. 4, 2016.
U.S. Appl. No. 14/240,712 Office Action dated Nov. 28, 2016.
U.S. Appl. No. 14/729,489 Office Action dated Dec. 7, 2016.
U.S. Appl. No. 14/848,143 Office Action dated Oct. 20, 2016.
U.S. Appl. No. 14/848,148 Office Action dated Oct. 28, 2016.
U.S. Appl. No. 14/848,153 Office Action dated Oct. 25, 2016.
U.S. Appl. No. 14/886,946 Office Action dated Oct. 5, 2016.
Wu et al. Wound healing effects of porcine placental extracts on rats with thermal injury. Br J Dermatol 148(2):236-245 (2003).
Yoshida. Placenta Power: For Health and Beauty—A useful guide for those seeking placenta-based remedies. Downloaded from http://www.melsmon.co.jp/img/commom/PlacentaPowerp002-121_04-09-08.pdf. (p. 1-41) (Aug. 2001).
Adatia et al. Correlation Between Corneal Sensitivity, Subjective Dry Eye Symptoms and Corneal Staining in Sjogren's Syndrome. Can I Ophthalmol 39:767-771 (2004).
Brophy. Gas Chromatographic Quality Control for Oil of *Melaleuca* Terpinen-4-ol Type (Australian Tea Tree). J. Agric. Food Chem. 37:1330-1335 (1989).
Budavari et al. The Merck Index, Thirteenth Edition, Merck & Co., Inc., Rahway, NJ (4 pgs) (2001).
Co-pending U.S. Appl. No. 15/195,189, filed Jun. 28, 2016.
Co-pending U.S. Appl. No. 15/215,228, filed Jul. 20, 2016.
CTFA (Cosmetic, Toiletry, and Fragrance Association) International Cosmetic Ingredient Dictionary and Handbook, 10th Ed. (2004) (abstract only).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) 2016 on May 1-May 5 (Washington State Convention Center, Seattle, Washington) Abstract No. 5384-B005 (2 pgs).
Inactive Ingredient Guide, U.S. Food and Drug Administration (FDA) Center for Drug Evaluation and Research (CDER) Office of Management, http://www.accessdata.fda.gov/scripts/cder/iig/index.cfm (8 pgs.) (2012).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7 (Colorado Convention Center Denver, CO) Abstract No. 1126-B029 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3-May 7 (Colorado Convention Center Denver, CO) Abstract No. 2287-B0192 (2 pgs).
Merck Manuals Online Medical Library, Age-Related Macular Degeneration (ARMD), originally printed Aug. 13, 2008/reprinted 2016 from http://www.merck.com/mmpe/print/sec09/ch106/ch106b.html (9 pgs.).
Mondello et al. In vivo activity of terpenin-4-ol, the main bioactive component of *Melaleuca alternifolia* Cheel (tea tree) oil against azole-susceptible and -resistant human pathogenic Candida species. BMC Infectious Diseases 6:158 (2006).
PCT/US2015/033955 International Search Report and Written Opinion dated Aug. 19, 2015.

(56) References Cited

OTHER PUBLICATIONS

PCT/US2015/059142 International Search Report and Written Opinion dated Jan. 19, 2016.
Rennie et al. Applications of Amniotic Membrane and Fluid in Stem Cell Biology and Regenerative Medicine. Stem Cells International (ID 721538):1-13 (2012).
Trommer et al. Overcoming the Stratum Corneum: Modulation of Skin Penetration. A review. Skin Pharmacol Physiol 19(2):106-121 (2006).
U.S. Appl. No. 13/704,231 Office Action dated Aug. 2, 2016.
U.S. Appl. No. 14/886,946 Office Action dated Apr. 18, 2016.
English Translation of JP74043153B (App. S45-107284) (9 pgs.) (Pub. Nov. 19, 1974).
PCT/US2015/033955 International Preliminary Report on Patentability dated Dec. 15, 2016.
Relucenti et al. Cumulus oophorus extracellular matrix in the human oocyte: a role for adhesive proteins. Ital J Anat Embryol 110(2 Supp 1):219-224 (2005).
Salustri et al. PTX3 plays a key role in the organization of the cumulus oophorus extracellular matrix and in in vivo fertilization. Development 131:1577-1586 (2004).
U.S. Appl. No. 13/704,231 Office Action dated Jan. 19, 2017.
U.S. Appl. No. 14/848,148 Office Action dated Mar. 20, 2017.
U.S. Appl. No. 14/880,135 Office Action dated Dec. 23, 2016.
Wisniewski et al. Cytokine-induced gene expression at the crossroads of innate immunity, inflammation and fertility: TSG-6 and PTX3/TSG-14. Cytokine Growth Factor Rev 15(2-3):129-146 (2004).

\* cited by examiner

\*: indicates p < 0.05 when HC-HA, AMP, or mAMP is compared with PBS.
\* \*: indicates p < 0.05 when AMP is compared with mAMP at the same concentration

METHODS OF PROCESSING FETAL SUPPORT TISSUES, FETAL SUPPORT TISSUE POWDER PRODUCTS, AND USES THEREOF

CROSS REFERENCE

This application is the National Phase entry of International Application No. PCT/US2012/041685, filed on Jun. 8, 2012, which claims the benefit of and right of priority to U.S. Provisional Application No. 61/495,860, filed Jun. 10, 2011, both of which are incorporated herein by reference in their entireties.

BACKGROUND OF THE INVENTION

The placenta is a temporary organ that surrounds the fetus during gestation. The placenta allows for transport of gases and nutrients, and also provides other metabolic and endocrine functions. The amniotic membrane (AM) is an avascular membranous sac that is filled with amniotic fluid. This membrane is the innermost membrane surrounding a fetus in the amniotic cavity. This tissue consists of an epithelial layer and a subadjacent avascular stromal layer. The chorion surrounds the amniotic membrane. The chorion consists of two layers: an outer layer formed by the trophoblast, and an inner layer formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The umbilical cord connects the placenta to the fetus and transports oxygen to the fetus.

SUMMARY OF THE INVENTION

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal tissue powder product. In some embodiments, the fetal support tissue is selected from an umbilical cord, placenta, placental amniotic membrane, umbilical amniotic membrane, chorion, amnion-chorion or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising grinding a lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) obtaining fetal support tissue; (b) freezing the fetal support tissue to produce frozen fetal support tissue, (c) lyophilizing the frozen fetal support tissue to produce a lyophilized fetal support tissue; and (d) grinding the lyophilized fetal support tissue to generate a fetal tissue powder product. In some embodiments, the fetal support tissue is selected from an umbilical cord, placenta, placental amniotic membrane, umbilical amniotic membrane, chorion, amnion-chorion or any combination thereof. In some embodiments, the fetal support tissue is fresh. In some embodiments, the fetal support tissue is frozen or previously frozen. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising: (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) lyophilizing fetal support tissue to produce a lyophilized fetal support tissue; and (b) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: grinding lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) obtaining fetal support tissue; (b) freezing the fetal support tissue to produce frozen fetal support tissue, (c) lyophilizing the frozen fetal support tissue to produce a lyophilized fetal support tissue; and (d) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) freezing the fetal support tissue to produce frozen fetal support tissue, (b) lyophilizing the frozen fetal support tissue to produce a lyophilized fetal support tissue; and (c) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) lyophilizing frozen fetal support tissue to produce a lyophilized fetal support tissue; and (b) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are fetal support tissue powder products prepared by a method comprising: (a) obtaining fetal support tissue; (b) lyophilizing the fetal support tissue to produce a lyophilized fetal support tissue; and (c) grinding the lyophilized fetal support tissue to generate a fetal tissue powder product. In some embodiments, the fetal support tissue is selected from an umbilical cord, placenta, placental amniotic membrane, umbilical amniotic membrane, chorion, amnion-chorion or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are fetal support tissue powder products prepared by a method comprising (a) lyophilizing a fetal support tissue to produce a lyophilized fetal support tissue, and (b) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are fetal support tissue powder products prepared by a method comprising grinding a lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, is a pharmaceutical composition, comprising a fetal support tissue powder product disclosed herein and a pharmaceutically-acceptable carrier. In some embodiments, the pharmaceutically-acceptable carrier is selected from carbomer, cellulose, collagen, glycerin, hexylene glycol, hyaluronic acid, hydroxypropyl cellulose, phosphoric acid, polysorbate 80, propylene glycol, propylene glycol stearate, saline, sodium hydroxide, sodium phosphate, sorbital, water, xanthan gum, or any combination thereof. In some embodiments, the pharmaceutical composition is administered or provided as a cream, lotion, ointment, ophthalmic solution, spray, paste, gel, film, or paint. In some embodiments, the pharmaceutical composition is anti-inflammatory, anti-scarring, anti-angiogenic, anti-adhesion, or promotes wound healing. In some embodiments, the pharmaceutical composition further comprises at least one component of a basement membrane matrix. In some embodiments, the pharmaceutical composition further comprises collagen, fibrin, hyaluronic acid, or any combinations thereof. In some embodiments, the pharmaceutical composition further comprises collagen. In some embodiments, the pharmaceutical composition further comprises fibrin. In some embodiments, the pharmaceutical composition further comprises hyaluronic acid.

Disclosed herein, in certain embodiments, are methods of treating a wound in an individual in need thereof, comprising administering a pharmaceutical composition comprising a fetal support tissue powder product disclosed herein to the wound for a period of time sufficient to treat the wound. In some embodiments, the pharmaceutical composition is anti-inflammatory, anti-scarring, anti-angiogenic, anti-adhesion, or promotes wound healing. In some embodiments, the wound is a dermatological condition selected from a dermal burn or a scar. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of treating a spinal condition in an individual in need thereof, comprising administering a pharmaceutical composition comprising a fetal support tissue powder product disclosed herein to the individual for a period of time sufficient to treat the spinal condition. In some embodiments, the pharmaceutical composition is anti-inflammatory, anti-scarring, anti-angiogenic, anti-adhesion, or promotes wound healing. In some embodiments, the spinal condition is selected from a herniated disc, spinal adhesion or discitis. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of treating an arthritic condition in an individual in need thereof, comprising administering a pharmaceutical composition comprising a fetal support tissue powder product disclosed herein to the individual for a period of time sufficient to treat the arthritic condition. In some embodiments, the pharmaceutical composition is anti-inflammatory, anti-scarring, anti-angiogenic, anti-adhesion, or promotes wound healing. In some embodiments, the arthritic condition is selected from osteoarthritis, rheumatoid arthritis, septic arthritis, ankylosing spondylitis, or spondylosis. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of regenerating or repairing bone, tissue or cartilage in an individual in need thereof, comprising administering a pharmaceutical composition comprising a fetal support tissue powder product disclosed herein to the individual for a period of time sufficient to regenerate or repair bone, tissue or cartilage. In some embodiments, the pharmaceutical composition is anti-inflammatory, anti-scarring, anti-angiogenic, anti-adhesion, or promotes wound healing. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of treating inflammation in an individual in need thereof, comprising administering a pharmaceutical composition comprising a fetal support tissue powder product disclosed herein to the individual for a period of time sufficient to treat the inflammation. In some embodiments, the inflammation is associated with Acute coronary syndrome; Atopic dermatitis; Crohn's disorder; Dermatitis; Diabetes mellitus type 1; Dry eye; Endotoxic shock; Graft-versus-host disease; Psoriasis; Rheumatoid arthritis; Rheumatoid spondylitis; Periodontitis; or any combination thereof. In some embodiments, the inflammation is associated with acute coronary syndrome. In some embodiments, the inflammation is associated with atopic dermatitis. In some embodiments, the inflammation is associated with Crohn's disorder. In some embodiments, the inflammation is associated with dermatitis. In some embodiments, the inflammation is associated with Diabetes mellitus type 1. In some embodiments, the inflammation is associated with dry eye. In some embodiments, the inflammation is associated with endotoxic shock. In some embodiments, the inflammation is associated with Graft-versus-Host disease. In some embodiments, the inflammation is associated with psoriasis. In some embodiments, the inflammation is associated with rheumatoid arthritis. In some embodiments, the inflammation is associated with rheumatoid spondylitis. In some embodiments, the inflammation is associated with periodontitis. In some embodiments, the pharmaceutical composition is administered or provided as a patch. In some embodiments, the pharmaceutical composition is administered or provided as a wound dressing. In some embodiments, the pharmaceutical composition is formulated for injection. In some embodiments, the pharmaceutical composition is administered systemically.

Disclosed herein, in certain embodiments, is a composition comprising a fetal support tissue powder product and a biologically compatible aqueous solution that is syringeable through a 20 gauge needle. In some embodiments, the composition is syringeable through a 21 gauge needle. In some embodiments, the composition is syringeable through a 23 gauge needle.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15 exemplifies the dose-dependent effects of AMP on pre-osteoblastic MC3T3-E1 cells.

FIG. 16 exemplifies the effects of AMP on mineralization as compared to conventional agents.

FIG. 17 demonstrates that AMP enhances mineralization of MC3T3-E1 cells.

FIG. 18 demonstrates that AMP does not increase cell proliferation in MC3T3-E1 cells.

FIG. 19 demonstrates that AMP alone can induce human bone marrow mesenchymal stem cells (hBMMSCs) and human amniotic membrane stromal stem cells (hAM Stroma) to undergo osteogenesis and mineralization.

DETAILED DESCRIPTION OF THE INVENTION

Figure 1:
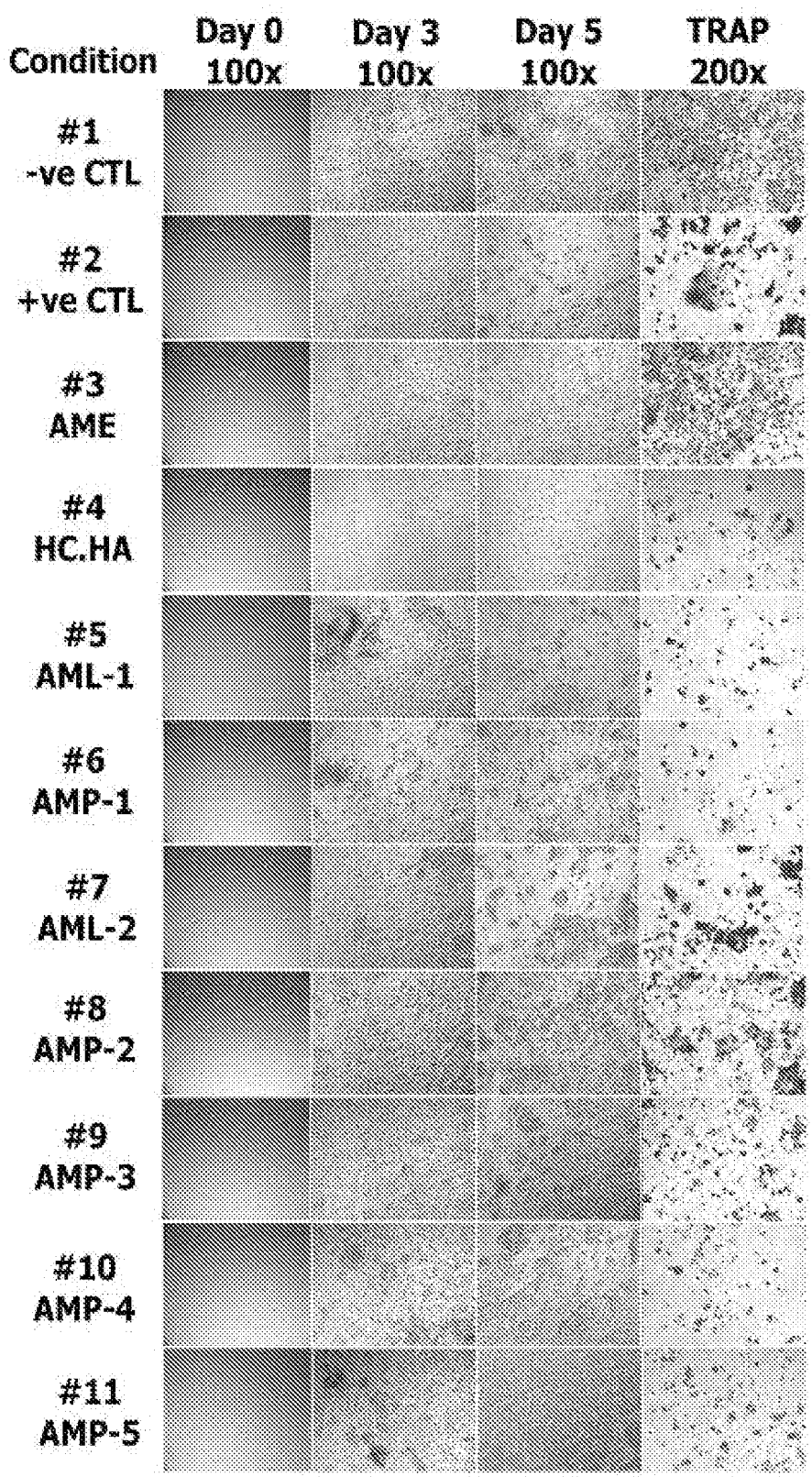
FIG. 1 exemplifies the effects of treating macrophages with AMP. Tartrate Resistant Acid Phosphatase (TRAP) staining of macrophage cells, treated with amniotic membrane extract (AME), Hyaluronan and the Heavy Chains of Inter-α-inhibitor (HC-HA) complex, amniotic membrane lysate (AML), or amniotic membrane powder (AMP). TRAP is highly expressed in osteoclasts, which are bone-absorbing cells.

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal tissue powder product. In some embodiments, the fetal support tissue is selected from an umbilical cord, placenta, placental amniotic membrane, umbilical amniotic membrane, chorion, amnion-chorion or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising grinding a lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) obtaining fetal support tissue; (b) freezing the fetal support tissue to produce frozen fetal support tissue, (c) lyophilizing the frozen fetal support tissue to produce a lyophilized fetal support tissue; and (d) grinding the lyophilized fetal support tissue to generate a fetal tissue powder product. In some embodiments, the fetal support tissue is selected from an umbilical cord, placenta, placental amniotic membrane, umbilical amniotic membrane, chorion, amnion-chorion or any combination thereof. In some embodiments, the fetal support tissue is fresh. In some embodiments, the fetal support tissue is frozen or previously frozen. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising: (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) lyophilizing fetal support tissue to produce a lyophilized fetal support tissue; and (b) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: grinding lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) obtaining fetal support tissue; (b) freezing the fetal support tissue to produce frozen fetal support tissue, (c) lyophilizing the frozen fetal support tissue to produce a lyophilized fetal support tissue; and (d) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) freezing the fetal support tissue to produce frozen fetal support tissue, (b) lyophilizing the frozen fetal support tissue to produce a lyophilized fetal support tissue; and (c) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are methods of preparing a fetal support tissue powder product, comprising: (a) lyophilizing frozen fetal support tissue to produce a lyophilized fetal support tissue; and (b) grinding the lyophilized fetal support tissue in a grinding container, wherein a fetal support tissue powder product is produced. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the grinding container is immersed in liquid nitrogen prior to grinding. In some embodiments, the grinding container is immersed in liquid nitrogen for at least 1 minute of the grinding process. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are fetal support tissue powder products prepared by a method comprising: (a) obtaining fetal support tissue; (b) lyophilizing the fetal support tissue to produce a lyophilized fetal support tissue; and (c) grinding the lyophilized fetal support tissue to generate a fetal tissue powder product. In some embodiments, the fetal support tissue is selected from an umbilical cord, placenta, placental amniotic membrane, umbilical amniotic membrane, chorion, amnion-chorion or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are fetal support tissue powder products prepared by a method comprising (a) lyophilizing a fetal support tissue to produce a lyophilized fetal support tissue, and (b) grinding the lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are fetal support tissue powder products prepared by a method comprising grinding a lyophilized fetal support tissue to produce a fetal support tissue powder product. In some embodiments, the fetal support tissue is selected from an amniotic membrane, chorion, amnion-chorion, umbilical cord, placenta or any combination thereof. In some embodiments, the fetal support tissue is fresh. In some embodiments, the fetal support tissue is frozen or previously frozen. In some embodiments, the fetal support tissue is frozen prior to lyophilization. In some embodiments, the fetal support tissue is divided into pieces prior to lyophilization. In some embodiments, the lyophilized fetal support tissue is divided into pieces prior to grinding. In some embodiments, the fetal support tissue powder product is frozen. In some embodiments, the fetal support tissue powder product is stored at ambient temperature. In some embodiments, the fetal support tissue powder product is aliquoted. In some embodiments, the fetal support tissue powder product is a) frozen; b) thawed; and c) aliquoted. In some embodiments, the fetal support tissue powder product is aliquoted without prior freezing. In some embodiments, the fetal support tissue powder product is stored at ambient temperature prior to being aliquoted. In some embodiments, the aliquoted fetal support tissue powder product is packaged into a packet, a vial, a pre-filled syringe, or a bottle. In some embodiments, the fetal support tissue powder product is anti-inflammatory, anti-scarring, anti-angiogenic, anti-adhesion, or promotes wound healing.

Disclosed herein, in certain embodiments, are pharmaceutical compositions, comprising a fetal support tissue powder product disclosed herein and a pharmaceutically-acceptable carrier. In some embodiments, the pharmaceutically-acceptable carrier is selected from carbomer, cellulose, collagen, glycerin, hexylene glycol, hyaluronic acid, hydroxypropyl cellulose, phosphoric acid, polysorbate 80, propylene glycol, propylene glycol stearate, saline, sodium hydroxide, sodium phosphate, sorbital, water, xanthan gum, or any combination thereof. In some embodiments, the pharmaceutical composition is administered or provided as a cream, lotion, ointment, ophthalmic solution, spray, paste, gel, film, or paint. In some embodiments, the pharmaceutical composition is anti-inflammatory, anti-scarring, anti-angiogenic, anti-adhesion, or promotes wound healing. In some embodiments, the pharmaceutical composition further comprises at least one component of a basement membrane matrix. In some embodiments, the pharmaceutical composition further comprises collagen, fibrin, hyaluronic acid, or any combinations thereof. In some embodiments, the pharmaceutical composition further comprises collagen. In some embodiments, the pharmaceutical composition further comprises fibrin. In some embodiments, the pharmaceutical composition further comprises hyaluronic acid.

Disclosed herein, in certain embodiments, are methods of treating a wound in an individual in need thereof, comprising administering a pharmaceutical composition comprising a fetal support tissue powder product disclosed herein to the wound for a period of time sufficient to treat the wound. In some embodiments, the pharmaceutical composition is anti-inflammatory, anti-scarring, anti-angiogenic, anti-adhesion, or promotes wound healing. In some embodiments, the wound is a dermatological condition selected from a dermal burn or a scar. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of treating a spinal condition in an individual in need thereof, comprising administering a pharmaceutical composition comprising a fetal support tissue powder product disclosed herein to the individual for a period of time sufficient to treat the spinal condition. In some embodiments, the pharmaceutical composition is anti-inflammatory, anti-scarring, anti-angiogenic, anti-adhesion, or promotes wound healing. In some embodiments, the spinal condition is selected from a herniated disc, spinal adhesion or discitis. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of treating an arthritic condition in an individual in need thereof, comprising administering a pharmaceutical composition comprising a fetal support tissue powder product disclosed herein to the individual for a period of time sufficient to treat the arthritic condition. In some embodiments, the pharmaceutical composition is anti-inflammatory, anti-scarring, anti-angiogenic, anti-adhesion, or promotes wound healing. In some embodiments, the arthritic condition is selected from osteoarthritis, rheumatoid arthritis, septic arthritis, ankylosing spondylitis, or spondylosis. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of regenerating or repairing bone, tissue or cartilage in an individual in need thereof, comprising administering a pharmaceutical composition comprising a fetal support tissue powder product disclosed herein to the individual for a period of time sufficient to regenerate or repair bone, tissue or cartilage. In some embodiments, the pharmaceutical composition is anti-inflammatory, anti-scarring, anti-angiogenic, anti-adhesion, or promotes wound healing. In some embodiments, the pharmaceutical composition is administered or provided as a patch. In some embodiments, the pharmaceutical composition is administered or provided as a wound dressing. In some embodiments, the pharmaceutical composition is formulated for injection.

Disclosed herein, in certain embodiments, are methods of treating inflammation in an individual in need thereof, comprising administering a pharmaceutical composition comprising a fetal support tissue powder product disclosed herein to the individual for a period of time sufficient to treat the inflammation. In some embodiments, the inflammation is associated with Acute coronary syndrome; Atopic dermatitis; Crohn's disorder; Dermatitis; Diabetes mellitus type 1; Dry eye; Endotoxic shock; Graft-versus-host disease; Psoriasis; Rheumatoid arthritis; Rheumatoid spondylitis; Periodontitis; or any combination thereof. In some embodiments, the inflammation is associated with acute coronary syndrome. In some embodiments, the inflammation is associated with atopic dermatitis. In some embodiments, the inflammation is associated with Crohn's disorder. In some embodiments, the inflammation is associated with dermatitis. In some embodiments, the inflammation is associated with Diabetes mellitus type 1. In some embodiments, the inflammation is associated with dry eye. In some embodiments, the inflammation is associated with endotoxic shock. In some embodiments, the inflammation is associated with Graft-versus-Host disease. In some embodiments, the inflammation is associated with psoriasis. In some embodiments, the inflammation is associated with rheumatoid arthritis. In some embodiments, the inflammation is associated with rheumatoid spondylitis. In some embodiments, the inflammation is associated with periodontitis. In some embodiments, the pharmaceutical composition is administered or provided as a patch. In some embodiments, the pharmaceutical composition is administered or provided as a wound dressing. In some embodiments, the pharmaceutical composition is formulated for injection. In some embodiments, the pharmaceutical composition is administered systemically.

Disclosed herein, in certain embodiments, are compositions comprising a fetal support tissue powder product and a biologically compatible aqueous solution that is syringeable through a 20 gauge needle. In some embodiments, the composition is syringeable through a 21 gauge needle. In some embodiments, the composition is syringeable through a 23 gauge needle.

Certain Terminology

As used herein, "fetal support tissue" means tissue used to support the development of a fetus. Examples of fetal support tissue include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

As used herein, "fetal support tissue powder product" means a powder or any other product resulting from grinding fetal support tissue. Examples of fetal support tissue include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

As used herein, "powder" means matter in the form of fine dry particles or matrix. In some embodiments, the particles are not uniform in size. In some embodiments, the particles are substantially uniform in size.

As used herein, "grinding" means any method of reducing fetal support tissue to small particles or a powder. The term grinding includes micronizing, pulverizing, homogenizing, filing, milling, grating, pounding, and crushing.

As used herein, "placenta" means the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" means the membrane formed by extraembryonic mesoderm and the two layers of trophoblast. The chorionic villi emerge from the chorion, invade the endometrium, and allow transfer of nutrients from maternal blood to fetal blood. The chorion consists of two layers: an outer layer formed by the trophoblast, and an inner layer formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The avascular amnion is adherent to the inner layer of the chorion.

As used herein, "amnion-chorion" means a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

As used herein, "umbilical cord" means the organ that connects a developing fetus to the placenta. The umbilical cord is composed of Wharton's jelly, a gelatinous substance made largely from mucopolysaccharides. It contains one vein, which carries oxygenated, nutrient-rich blood to the fetus, and two arteries that carry deoxygenated, nutrient-depleted blood away.

As used herein, "placental amniotic membrane" (PAM) means amniotic membrane derived from the placenta. In some embodiments, the PAM is substantially isolated.

As used herein, "umbilical cord amniotic membrane" (UCAM) means amniotic membrane derived from the umbilical cord. UCAM is a translucent membrane. The UCAM has multiple layers: an epithelial layer; a basement membrane; a compact layer; a fibroblast layer; and a spongy layer. It lacks blood vessels or a direct blood supply. In some embodiments, the UCAM is substantially isolated. In some embodiments, the UCAM comprises Wharton's Jelly. In some embodiments, the UCAM comprises blood vessels and/or arteries. In some embodiments, the UCAM comprises Wharton's Jelly and blood vessels and/or arteries.

"Substantially isolated" or "isolated" means that the fetal support tissue powder product has been separate from undesired materials (e.g., red blood cells, blood vessels, and arteries) derived from the original source organism. Purity, or "isolation" may be assayed by standard methods, and will ordinarily be at least about 10% pure, more ordinarily at least about 20% pure, generally at least about 30% pure, and more generally at least about 40% pure; in further embodiments at least about 50% pure, or more often at least about 60% pure; in still other embodiments, at least about 95% pure.

As used herein, "biological activity" means the activity of polypeptides and polysaccharides. In some embodiments, the activity of polypeptides and polysaccharides found in umbilical cord (and substantially isolated umbilical cord), UCAM (and substantially isolated UCAM), placenta (and substantially isolated placenta), PAM (and substantially isolated PAM), chorion (and substantially isolated chorion), or amnion-chorion (and substantially isolated amnion-chorion).

As used herein, the substantial preservation of biological activity or structural integrity means that when compared to the biological activity and structural integrity of non-processed tissue, the biological activity and structural integrity of the fetal support tissue powder product has only decreased by about 5%, about 10%, about 15%, about 20%, about 25%, about 30%, about 35%, about 40%, about 50%, or about 60%.

The term "fresh" refers to tissue that is less than 10 days old following birth, and which is in substantially the same form as it was following birth.

The terms "subject" and "individual" are used interchangeably. As used herein, both terms mean any animal, preferably a mammal, including a human or non-human. The terms patient, subject, and individual are used interchangeably. None of the terms are to be interpreted as requiring the supervision of a medical professional (e.g., a doctor, nurse, physician's assistant, orderly, hospice worker).

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, a "biologically compatible aqueous solution" refers to a solution having a pH and osmotic properties (e.g., tonicity, osmalality and/or oncotic pressure) suitable for maintaining the integrity of biological cells and/or tissues. Suitable biologically compatible aqueous solutions typically have a pH between 4 and 8.5 and are isotonic or only moderately hypotonic or hypertonic.

As used herein, "syringeable" refers to a composition being flowable through the tip of a hypodermic needle upon mild to moderate pressure.

Preparation of Powder

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal support tissue powder. Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to generate a fetal support tissue powder. Disclosed herein, in certain embodiments, are methods of preparing a fetal support tissue powder product comprising grinding a lyophilized fetal support tissue to generate a fetal support tissue powder. Disclosed herein, in certain embodiments, are methods of preparing a fetal support tissue powder product, comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate a fetal support tissue powder. Disclosed herein, in certain embodiments, are methods of preparing a fetal support tissue powder product comprising (a) freezing fetal support tissue to produce frozen fetal support tissue, (b) lyophilizing the frozen fetal support tissue to produce a lyophilized fetal support tissue, and (c) grinding the lyophilized fetal support tissue to generate a fetal support tissue powder. Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to generate a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Disclosed herein, in certain embodiments, are fetal support tissue powder products prepared by the method comprising: (a) obtaining fetal support tissue; (b) lyophilizing the fetal support tissue to produce a lyophilized fetal support tissue; and (c) grinding the lyophilized fetal support tissue to generate fetal support tissue powder. Disclosed herein, in certain embodiments, are fetal support tissue powder products prepared by the method comprising (a) lyophilizing a fetal support tissue to produce a lyophilized fetal support tissue, and (b) grinding the lyophilized fetal support tissue to produce a fetal support tissue powder. Disclosed herein, in certain embodiments, are fetal support tissue powder products prepared by the method comprising grinding a lyophilized fetal support tissue. Disclosed herein, in certain embodiments, are fetal support tissue powder products prepared by the method comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate fetal support tissue powder. Disclosed herein, in certain embodiments, are fetal support tissue powder products prepared by the method comprising (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder. Disclosed herein, in certain embodiments, are fetal support tissue powder products prepared by the method comprising (a) lyophilizing frozen fetal support tissue to produce a lyophilized fetal support tissue, and (c) grinding the lyophilized fetal support tissue to produce a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Initial Processing

Fetal support tissue is obtained from any suitable source (e.g., a hospital or tissue bank). Fetal support tissue may be obtained from any mammal, such as a human, non-human primate, cow or pig.

In some embodiments, the fetal support tissue is frozen (e.g., at or below 0° C.) until donor and specimen eligibility has been determined. In some embodiments, freezing the fetal support tissue kills substantially all cells found in the fetal support tissue. In some embodiments, freezing the fetal support tissue kills substantially all cells found in fetal support tissue while maintaining or increasing the biological activity of the fetal support tissue relative to fresh (i.e., non-frozen) fetal support tissue. In some embodiments, freezing the fetal support tissue results in the loss of metabolic activity in substantially all cells found in the fetal support tissue. In some embodiments, freezing the fetal support tissue results in the loss of metabolic activity in substantially all cells found in the fetal support tissue while maintaining or increasing the biological activity of the fetal support tissue (e.g., its anti-inflammatory, anti-scarring, anti-antigenic, and anti-adhesion properties) relative to fresh (i.e., non-frozen) fetal support tissue.

In some embodiments, the fetal support tissue is not frozen. If the fetal support tissue is not frozen, it is processed as described immediately below.

All processing is done following Good Tissue Practices (GTP) to ensure that no contaminants are introduced into the fetal support tissue powder products.

The fetal support tissue is tested for HIV-1, HIV-2, HTLV-1, hepatitis B and C, West Nile virus, cytomegalovirus, human transmissible spongiform encephalopathy (e.g., Creutzfeldt-Jakob disease) and *treponema pallidum* using an FDA licensed screening test. Any indication that the tissue is contaminated with HIV-1, HIV-2, HTLV-1, hepatitis B and C, West Nile virus, or cytomegalovirus results in the immediate quarantine and subsequent destruction of the tissue specimen.

Further, the donor's medical records are examined for risk factors for and clinical evidence of hepatitis B, hepatitis C, or HIV infection. Any indication that the donor has risk factors for, and/or clinical evidence of, infection with HIV-1, HIV-2, HTLV-1, hepatitis B and C, West Nile virus, cytomegalovirus, human transmissible spongiform encephalopathy (e.g., Creutzfeldt-Jakob disease) and *treponema pallidum* results in the immediate quarantine and subsequent destruction of the tissue specimen.

In some embodiments, substantially all blood is removed from the fetal support tissue. In some embodiments, substantially all blood is removed from the fetal support tissue before the fetal support tissue is frozen.

In some embodiments, blood is not removed from the fetal support tissue. In some embodiments, blood is not removed from the fetal support tissue before the fetal support tissue is frozen.

In some embodiments, the fetal support tissue is contacted with an isotonic buffer. In some embodiments, the fetal support tissue is contacted with saline, PBS, PBS 1X, Ringer's solution, Hartmann's solution, TRIS-buffered saline, HEPES-buffered saline, EBSS, HBSS, Tyrode's salt Solution, Grey's Balanced Salt Solution, DMEM, EMEM, GMEM, RPMI, or any combinations thereof.

In some embodiments, the fetal support tissue is washed with buffer with agitation to remove excess blood and tissue. Washing with agitation may reduce wash time.

In some embodiments, the fetal support tissue is umbilical cord or umbilical cord amniotic membrane. In some embodiments, the Wharton's Jelly is not removed from the umbilical cord or the umbilical cord amniotic membrane. In some embodiments, part or all of the Wharton's Jelly is removed from the umbilical cord or the umbilical cord amniotic membrane.

Umbilical cord comprises two arteries (the umbilical arteries) and one vein (the umbilical vein). In certain instances, the vein and arteries are surrounded (or suspended or buried) within the Wharton's Jelly. In some embodiments, the veins and arteries are not removed from the umbilical cord. In some embodiments, the vein and arteries are removed from the umbilical cord. In some embodiments, the vein and arteries are removed concurrently with the removal of the Wharton's Jelly.

Freezing

In some embodiments, the isolated fetal support tissue is frozen (e.g., exposed to a temperature below about 0° C., −20° C., −40° C., −50° C., −60° C., −70° C., −75° C., −80° C., −90° C., or −100° C.) before being lyophilized. In some embodiments, the samples are frozen at about −40° C. In some embodiments, freezing the fetal support tissue prior to lyophilization results in the fetal support tissue powder product having greater potency (e.g., anti-inflammatory potency, anti-scarring potency, anti-angiogenesis potency, anti-adhesion potency, or wound healing potency) as compared to a fetal support tissue powder product that is not frozen prior to lyophilization.

In some embodiments, methods of making fetal support tissue powder products comprise (a) freezing the fetal support tissue, and (b) drying the fetal support tissue.

In some embodiments, methods of making fetal support tissue powder products comprise (a) freezing the fetal support tissue at about −40° C., and (b) drying the fetal support tissue at −5° C. at a pressure of 100 millitorr. In some embodiments, methods of making fetal support tissue powder products comprise (a) freezing the fetal support tissue at about −40° C. for about 3 hours, and (b) drying the fetal support tissue at −5° C. at a pressure of 100 millitorr for about 21 hours.

In some embodiments, methods of making fetal support tissue powder products comprise (a) freezing the fetal support tissue at about −40° C., (b) drying the fetal support tissue at −5° C. at a pressure of 100 millitorr, and (c) drying the fetal support tissue 25° C. at a pressure of about 100 millitorr. In some embodiments, methods of making fetal support tissue powder products comprise (a) freezing the fetal support tissue at about −40° C. for about 3 hours, (b) drying the fetal support tissue at −5° C. at a pressure of 100 millitorr for about 21 hours, and (c) drying the fetal support tissue at about 25° C. at a pressure of about 100 millitorr for about 16 hours.

Lyophilization

In some embodiments, methods of making a fetal support tissue powder product comprise lyophilizing the fetal support tissue before grinding the fetal support tissue. Duration of lyophilization, temperature at which lyophilization is conducted, and the pressure at which lyophilization is conducted may be varied according to the desired outcome. It is within the skill of one skilled in the art to determine the necessary parameters.

In some embodiments, the isolated fetal support tissue is lyophilized by any suitable method (e.g., exposure to a liquid gas, placement in a freezer). In some embodiments, the isolated fetal support tissue is placed in the vacuum chamber of a lyophilization device until all or substantially all fluid (e.g., water) has been removed.

In some embodiments, the fetal support tissue is frozen prior to lyophilization.

Primary Drying Cycle

The fetal support tissue is lyophilized at any suitable temperature. In some embodiments, lyophilizing the fetal support tissue at a temperature at or below freezing results in the fetal support tissue powder product having greater potency (e.g., anti-inflammatory potency, anti-scarring potency, anti-angiogenesis potency, anti-adhesion potency, or wound healing potency) as compared to a fetal support tissue powder product that is not lyophilized at or below freezing. In some embodiments, the fetal support tissue is lyophilized at a temperature below freezing. In some embodiments, the fetal support tissue is lyophilized at a temperature below about 0° C., −20° C., −40° C., −50° C., −60° C., −70° C., −75° C., −80° C., −90° C., −100° C.). In some embodiments, the fetal support tissue is lyophilized at −5° C.

In some embodiments, the primary drying cycle occurs at a pressure of less than about 500 millitorr. In some embodiments, the primary drying cycle occurs at a pressure of less than about 400 millitorr. In some embodiments, the primary drying cycle occurs at a pressure of less than about 300 millitorr. In some embodiments, the primary drying cycle occurs at a pressure of less than about 250 millitorr. In some embodiments, the primary drying cycle occurs at a pressure of less than about 200 millitorr. In some embodiments, the fetal support tissue is lyophilized at a pressure of 100 millitorr. In some embodiments, decreasing the lyophilization pressure decreases the lyophilization time. In some embodiments, lyophilization is more effective at a pressure of less than 500 millitorr.

In some embodiments, lyophilization occurs until the fetal support tissue is dry enough for the fetal support tissue to be effectively ground. Grinding ease and efficiency is increased with the dryness of the fetal support tissue. In some embodiments, lyophilization occurs until substantially all moisture is removed from the fetal support tissue. The lyophilization time required depends on the type of tissue used, the amount of tissue, and the thickness of the tissue. In some embodiments, lyophilization occurs for more than about 12 hours. In some embodiments, lyophilization occurs for more than about 14 hours. In some embodiments, lyophilization occurs for more than about 16 hours. In some embodiments, lyophilization occurs for more than about 18 hours. In some embodiments, lyophilization occurs for more than about 20 hours. In some embodiments, lyophilization occurs for more than about 21 hours. In some embodiments, lyophilization occurs for more than about 22 hours. In some embodiments, lyophilization occurs for more than about 23 hours. In some embodiments, lyophilization occurs for about 24 hours.

In some embodiments, the fetal support tissue is lyophilized at −5° C. at a pressure of 100 millitorr. In some embodiments, the fetal support tissue is lyophilized at −5° C. at a pressure of 100 millitorr for about 21 hours.

In some embodiments, methods of making a fetal support tissue powder product further comprise gradually increasing the ambient temperature of the lyophilizer to room temperature (i.e., about 25° C.) following lyophilization. The rate at which the temperature of the lyophilizer is increased depends on the capability of the equipment. In some embodiments, increasing the temperature of the lyophilizer to room temperature helps to prevent condensation when taking the tissue out of the lyophilizer.

Secondary Drying Cycle

In some embodiments, methods of making fetal support tissue powder products further comprise a secondary drying cycle. In some embodiments, the secondary drying cycle occurs at room temperature (e.g., about 25° C.). The temperature of the secondary drying cycle may be any temperature above the temperature set for primary drying. In some embodiments, condensation is decreased or prevented if the temperature of the secondary drying cycle is at about room temperature (e.g., 25° C.).

In some embodiments, the secondary drying cycle occurs at a pressure of less than about 500 millitorr. In some embodiments, the secondary drying cycle occurs at a pressure of less than about 400 millitorr. In some embodiments, the secondary drying cycle occurs at a pressure of less than about 300 millitorr. In some embodiments, the secondary drying cycle occurs at a pressure of less than about 250 millitorr. In some embodiments, the secondary drying cycle occurs at a pressure of less than about 200 millitorr. In some embodiments, the secondary drying cycle occurs at a pressure of about 100 millitorr. In some embodiments, decreasing the drying pressure decreases the lyophilization time.

In some embodiments, the secondary drying cycle lasts for less than about 24 hours. In some embodiments, the secondary drying cycle lasts for less than about 20 hours. In some embodiments, the secondary drying cycle lasts for less than about 18 hours. In some embodiments, the secondary drying cycle lasts for less than about 16 hours. In some embodiments, the secondary drying cycle lasts for about 16 hours. In some embodiments, the secondary drying cycle lasts for less than about 14 hours. In some embodiments, the secondary drying cycle lasts for less than about 12 hours. In some embodiments, the secondary drying cycle lasts for less than about 10 hours. In some embodiments, the secondary drying cycle lasts for less than about 8 hours. In some embodiments, the secondary drying cycle lasts for less than about 6 hours. In some embodiments, the secondary drying cycle lasts for less than about 4 hours. In some embodiments, the secondary drying cycle lasts for less than about 2 hours. In some embodiments, the secondary drying cycle lasts for less than about 1 hours.

In some embodiments, methods of making fetal support tissue powder products further comprise a secondary drying cycle at 25° C. at a pressure of 100 millitorr. In some embodiments, methods of making fetal support tissue powder products further comprise a secondary drying cycle at 25° C. at a pressure of 100 millitorr for less than about 16 hours.

In some embodiments, methods of making fetal support tissue powder products comprise a primary drying cycle at about −5° C. at a pressure of about 100 millitorr, and a secondary drying cycle at about 25° C. at a pressure of about 100 millitorr. In some embodiments, methods of making fetal support tissue powder products comprise a primary drying cycle at about −5° C. at a pressure of about 100 millitorr for about 21 hours, and a secondary drying cycle at about 25° C. at a pressure of about 100 millitorr for less than about 16 hours.

Grinding

In some embodiments, the lyophilized fetal support tissue is ground by any suitable method. Duration and frequency of grinding may be varied according to the desired outcome. It is within the skills of one skilled in the art to determine the necessary parameters.

In some embodiments, the lyophilized fetal support tissue is ground by use of a grinding container. In some embodiments, the lyophilized fetal support tissue is ground by use of a pulverizer (e.g., a Bessman Tissue Pulverizer or a Covaris CryoPrep). In some embodiments, the lyophilized fetal support tissue is ground by use of a tissue grinder (e.g., a Potter-Elvehjem grinder or a Wheaton Overhead Stirrer). In some embodiments, the lyophilized fetal support tissue is ground by use of a sonicator. In some embodiments, the lyophilized fetal support tissue is ground by use of a bead beater. In some embodiments, the lyophilized fetal support tissue is ground by use of a freezer/mill (e.g., a SPEX SamplePrep Freezer/Mill). In some embodiments, lyophilized fetal support tissue is ground by use of a pestle and mortar. In some embodiments, the lyophilized fetal support tissue is ground by manual use of a pestle and mortar.

In some embodiments, the lyophilized fetal support tissue is ground by use of a grinding container. In some embodiments, the fetal support tissue is ground at a frequency of between about 10 Hz and about 25 Hz. In some embodiments, the fetal support tissue is ground at a frequency of about 10 Hz. In some embodiments, the fetal support tissue is ground at a frequency of about 15 Hz. In some embodiments, the fetal support tissue is ground at a frequency of about 20 Hz. In some embodiments, the fetal support tissue is ground at a frequency of about 25 Hz. In some embodiments, grinding lasts for any suitable time period. The lower the grinding frequency, the greater the amount of time required to grind the lyophilized fetal support tissue. The duration of grinding varies with the desired form of the powder. In some embodiments, grinding lasts for between about 1 and about 6 minutes, for example about 1 minute, about 2 minutes, about 3 minutes, about 4 minutes, about 5 minutes, or about 6 minutes.

In some embodiments, grinding the lyophilized fetal support tissue further comprises continuously freezing the lyophilized fetal support tissue. For example, in some embodiments, the lyophilized fetal support tissue is placed in a grinding container and the grinding container is exposed to temperatures below 0° C. (e.g., the grinding container is immersed in liquid nitrogen or the container comprises an automated liquid nitrogen cooling feature).

Exemplary Protocols

In some embodiments, the fetal support tissue powder product is prepared by (a) freezing the fetal support tissue at a temperature of about −40° C. for about 3 hours to generate frozen fetal support tissue; (b) drying (i.e., lyophilizing) the frozen fetal support tissue at about −5° C. and a pressure of about 100 millitorr for between about 20 and about 21 hours to generate lyophilized fetal support tissue; and (c) grinding the lyophilized fetal support tissue at a frequency of about 25 Hz for about 6 minutes to generate a fetal support tissue powder product.

In some embodiments, the fetal support tissue powder product is prepared by (a) freezing the fetal support tissue at a temperature of about −40° C. for about 3 hours to generate frozen fetal support tissue; (b) drying (i.e., lyophilizing) the frozen fetal support tissue at about −5° C. and a pressure of about 100 millitorr for between about 20 and about 21 hours in a lyophilization device to generate lyophilized fetal support tissue; (d) increasing the temperature of the lyophilization device from about −5° C. to ambient temperature (e.g., room temperature); and (d) grinding the lyophilized fetal support tissue at a frequency of about 25 Hz for about 6 minutes to generate a fetal support tissue powder product.

In some embodiments, the fetal support tissue powder product is prepared by (a) freezing the fetal support tissue at a temperature of about −40° C. for about 3 hours to generate frozen fetal support tissue; (b) drying (i.e., lyophilizing) the frozen fetal support tissue at about −5° C. and a pressure of about 100 millitorr for between about 20 and about 21 hours to generate a primary lyophilized fetal support tissue; (c) drying the primary lyophilized fetal support tissue powder product at about 25° C. to generate a lyophilized fetal support tissue powder product; and (d) grinding the lyophilized fetal support tissue at a frequency of about 25 Hz for about 6 minutes to generate a fetal support tissue powder product.

In some embodiments, the fetal support tissue powder product is prepared by (a) freezing the fetal support tissue at a temperature of about −40° C. for about 3 hours to generate frozen fetal support tissue; (b) drying (i.e., lyophilizing) the frozen fetal support tissue at about −5° C. and a pressure of about 100 millitorr for between about 20 and about 21 hours in a lyophilization device to generate lyophilized fetal support tissue; (c) increasing the temperature of the lyophilization device from about −5° C. to ambient temperature (e.g., room temperature); (d) drying the primary lyophilized fetal support tissue powder product at about 25° C. to produce a lyophilized fetal support tissue powder product; and (e) grinding the lyophilized fetal support tissue at a frequency of about 25 Hz for about 6 minutes to generate a fetal support tissue powder product.

Resuspension

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal support tissue powder. Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to generate a fetal support tissue powder. Disclosed herein, in certain embodiments, are methods of preparing a fetal support tissue powder product comprising grinding a lyophilized fetal support tissue to generate a fetal support tissue powder. Disclosed herein, in certain embodiments, are methods of preparing a fetal support tissue powder product, comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate a fetal support tissue powder. Disclosed herein, in certain embodiments, are methods of preparing a fetal support tissue powder product comprising (a) freezing fetal support tissue to produce frozen fetal support tissue, (b) lyophilizing the frozen fetal support tissue to produce a lyophilized fetal support tissue, and (c) grinding the lyophilized fetal support tissue to generate a fetal support tissue powder. Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to generate a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Disclosed herein, in certain embodiments, are fetal support tissue powder products prepared by the method comprising: (a) obtaining fetal support tissue; (b) lyophilizing the fetal support tissue to produce a lyophilized fetal support tissue; and (c) grinding the lyophilized fetal support tissue to generate fetal support tissue powder. Disclosed herein, in certain embodiments, are fetal support tissue powder products prepared by the method comprising (a) lyophilizing a fetal support tissue to produce a lyophilized fetal support tissue, and (b) grinding the lyophilized fetal support tissue to produce a fetal support tissue powder. Disclosed herein, in certain embodiments, are fetal support tissue powder products prepared by the method comprising grinding a lyophilized fetal support tissue. Disclosed herein, in certain embodiments, are fetal support tissue powder products prepared by the method comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate fetal support tissue powder. Disclosed herein, in certain embodiments, are fetal support tissue powder products prepared by the method comprising (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder. Disclosed herein, in certain embodiments, are fetal support tissue powder products prepared by the method comprising (a) lyophilizing frozen fetal support tissue to produce a lyophilized fetal support tissue, and (c) grinding the lyophilized fetal support tissue to produce a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

In some embodiments, a fetal support tissue powder product disclosed herein is rehydrated by contacting the fetal support tissue powder product with a buffer or with water. In some embodiments, a fetal support tissue powder product disclosed herein is contacted with an isotonic buffer. In some embodiments, a fetal support tissue powder product disclosed herein is contacted with saline. In some embodiments, a fetal support tissue powder product disclosed herein is contacted with PBS. In some embodiments, a fetal support tissue powder product disclosed herein is contacted with Ringer's solution. In some embodiments, a fetal support tissue powder product disclosed herein is contacted with Hartmann's solution. In some embodiments, a fetal support tissue powder product disclosed herein is contacted with a TRIS-buffered saline. In some embodiments, a fetal support tissue powder product disclosed herein is contacted with a HEPES-buffered saline; 50% DMEM+50% Glycerol; 10%, 20%, 30%, 40%, 50%, 60%, 70%, 80%, 90% or 100% glycerol; and/or 10%, 20%, 30%, 40%, 50%, 60%, 70%, 80%, 90% or 100% propylene glycol.

In some embodiments, a fetal support tissue powder product disclosed herein is contacted with saline. In some embodiments, a fetal support tissue powder product disclosed herein is contacted with about 0.9% saline.

Storage of Fetal Support Tissue and/or Fetal Support Tissue Powder Products

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal support tissue powder. Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to generate a fetal support tissue powder. Disclosed herein, in certain embodiments, are methods of preparing a fetal support tissue powder product comprising grinding a lyophilized fetal support tissue to generate a fetal support tissue powder. Disclosed herein, in certain embodiments, are methods of preparing a fetal support tissue powder product, comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate a fetal support tissue powder. Disclosed herein, in certain embodiments, are methods of preparing a fetal support tissue powder product comprising (a) freezing fetal support tissue to produce frozen fetal support tissue, (b) lyophilizing the frozen fetal support tissue to produce a lyophilized fetal support tissue, and (c) grinding the lyophilized fetal support tissue to generate a fetal support tissue powder. Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to generate a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Disclosed herein, in certain embodiments, are fetal support tissue powder products prepared by the method comprising: (a) obtaining fetal support tissue; (b) lyophilizing the fetal support tissue to produce a lyophilized fetal support tissue; and (c) grinding the lyophilized fetal support tissue to generate fetal support tissue powder. Disclosed herein, in certain embodiments, are fetal support tissue powder products prepared by the method comprising (a) lyophilizing a fetal support tissue to produce a lyophilized fetal support tissue, and (b) grinding the lyophilized fetal support tissue to produce a fetal support tissue powder. Disclosed herein, in certain embodiments, are fetal support tissue powder products prepared by the method comprising grinding a lyophilized fetal support tissue. Disclosed herein, in certain embodiments, are fetal support tissue powder products prepared by the method comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate fetal support tissue powder. Disclosed herein, in certain embodiments, are fetal support tissue powder products prepared by the method comprising (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder. Disclosed herein, in certain embodiments, are fetal support tissue powder products prepared by the method comprising (a) lyophilizing frozen fetal support tissue to produce a lyophilized fetal support tissue, and (c) grinding the lyophilized fetal support tissue to produce a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

In some embodiments, a fetal support tissue powder product disclosed herein is stored for later use. In some embodiments, a fetal support tissue powder product disclosed herein is stored in 50% DMEM+50% Glycerol. In some embodiments, a fetal support tissue powder product disclosed herein is stored in 10%, 20%, 30%, 40%, 50%, 60%, 70%, 80%, 90% or 100% glycerol. In some embodiments, a fetal support tissue powder product disclosed herein is stored in 10%, 20%, 30%, 40%, 50%, 60%, 70%, 80%, 90% or 100% propylene glycol.

In some embodiments, a fetal support tissue powder product disclosed herein is optionally contacted with a substrate (e.g., a wound dressing or bandage). In some embodiments, a fetal support tissue powder product disclosed herein is optionally reconstituted and contacted with a substrate (e.g., a wound dressing or bandage). In some embodiments, a fetal support tissue powder product disclosed herein is not contacted with a substrate.

Cryopreservation

In some embodiments, a fetal support tissue powder product disclosed herein is frozen for cryopreservation. In some embodiments, a fetal support tissue powder product disclosed herein is exposed to a liquid gas (e.g., liquid nitrogen or liquid hydrogen). In some embodiments, a fetal support tissue powder product disclosed herein is exposed to liquid nitrogen. In some embodiments, a fetal support tissue powder product disclosed herein does not contact the liquid gas. In some embodiments, a fetal support tissue powder product disclosed herein is placed in a container and the container is contacted with liquid gas. In some embodiments, a fetal support tissue powder product disclosed herein is exposed to the liquid gas until the fetal support tissue powder product disclosed herein is frozen.

Sterilization

In some embodiments, a fetal support tissue powder product disclosed herein is subject to terminal sterilization by any suitable (e.g., medically acceptable) method. In some embodiments, a fetal support tissue powder product is disclosed herein is exposed to gamma radiation for a period of time sufficient to sterilize the fetal support tissue powder product disclosed herein. In some embodiments, a fetal support tissue powder product disclosed herein is exposed to gamma radiation at about 10 to about 75 kGy for a period of time sufficient to sterilize the fetal support tissue powder product. In some embodiments, a fetal support tissue powder product disclosed herein is exposed to gamma radiation at about 10 to about 30 kGy for a period of time sufficient to sterilize the fetal support tissue powder product. In some embodiments, a fetal support tissue powder product disclosed herein is exposed to gamma radiation at about 15 to about 30 kGy for a period of time sufficient to sterilize the fetal support tissue powder product. In some embodiments, a fetal support tissue powder product disclosed herein is exposed to gamma radiation at about 25 kGy for a period of time sufficient to sterilize the fetal support tissue powder product. In some embodiments, a fetal support tissue powder product disclosed herein is exposed to gamma radiation at about 17.5 kGy for a period of time sufficient to sterilize the fetal support tissue powder product. In some embodiments, a fetal support tissue powder product disclosed herein is exposed to an electron beam for a period of time sufficient to sterilize the fetal support tissue powder product. In some embodiments, a fetal support tissue powder product disclosed herein is exposed to X-ray radiation for a period of time sufficient to sterilize the fetal support tissue powder product. In some embodiments, a fetal support tissue powder product disclosed herein is exposed to UV radiation for a period of time sufficient to sterilize the fetal support tissue powder product.

Fetal Support Tissue Powder Product Formulations

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal support tissue powder. Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to generate a fetal support tissue powder. Disclosed herein, in certain embodiments, are methods of preparing a fetal support tissue powder product comprising grinding a lyophilized fetal support tissue to generate a fetal support tissue powder. Disclosed herein, in certain embodiments, are methods of preparing a fetal support tissue powder product, comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate a fetal support tissue powder. Disclosed herein, in certain embodiments, are methods of preparing a fetal support tissue powder product comprising (a) freezing fetal support tissue to produce frozen fetal support tissue, (b) lyophilizing the frozen fetal support tissue to produce a lyophilized fetal support tissue, and (c) grinding the lyophilized fetal support tissue to generate a fetal support tissue powder. Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to generate a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Disclosed herein, in certain embodiments, are fetal support tissue powder products prepared by the method comprising: (a) obtaining fetal support tissue; (b) lyophilizing the fetal support tissue to produce a lyophilized fetal support tissue; and (c) grinding the lyophilized fetal support tissue to generate fetal support tissue powder. Disclosed herein, in certain embodiments, are fetal support tissue powder products prepared by the method comprising (a) lyophilizing a fetal support tissue to produce a lyophilized fetal support tissue, and (b) grinding the lyophilized fetal support tissue to produce a fetal support tissue powder. Disclosed herein, in certain embodiments, are fetal support tissue powder products prepared by the method comprising grinding a lyophilized fetal support tissue. Disclosed herein, in certain embodiments, are fetal support tissue powder products prepared by the method comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate fetal support tissue powder. Disclosed herein, in certain embodiments, are fetal support tissue powder products prepared by the method comprising (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder. Disclosed herein, in certain embodiments, are fetal support tissue powder products prepared by the method comprising (a) lyophilizing frozen fetal support tissue to produce a lyophilized fetal support tissue, and (c) grinding the lyophilized fetal support tissue to produce a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Disclosed herein, in certain embodiments, are compositions comprising a fetal support tissue powder product and a biologically compatible aqueous solution that are syringeable through a 20 gauge needle. In some embodiments, the composition is syringeable through a 21 gauge needle. In some embodiments, the composition is syringeable through a 23 gauge needle.

In some embodiments, a fetal support tissue powder product disclosed herein is formulated as a solution, suspension or emulsion. In some embodiments, a fetal support tissue powder product disclosed herein is formulated for topical administration.

Pharmaceutical formulations disclosed herein are formulated in any suitable manner. Any suitable technique, carrier, and/or excipient is contemplated for use with a fetal support tissue powder product disclosed herein.

Creams and Lotions

Disclosed herein, in certain embodiments, is a topical formulation of a fetal support tissue powder product disclosed herein wherein the topical formulation is in the form of a cream. In certain instances, creams are semisolid (e.g., soft solid or thick liquid) formulations that include a fetal support tissue powder product disclosed herein dispersed in an oil-in-water emulsion or a water-in-oil emulsion.

Disclosed herein, in certain embodiments, is a topical formulation of a fetal support tissue powder product disclosed herein wherein the topical formulation is in the form of a lotion. In certain instances, lotions are fluid emulsions (e.g., oil-in-water emulsions or a water-in-oil emulsion). In some embodiments, the hydrophobic component of a lotion and/or cream is derived from an animal (e.g., lanolin, cod liver oil, and ambergris), plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), or petroleum (e.g., mineral oil, or petroleum jelly).

Ointments

Disclosed herein, in certain embodiments, is a topical formulation of a fetal support tissue powder product disclosed herein wherein the topical formulation is in the form of an ointment. In certain instances, ointments are semisolid preparations that soften or melt at body temperature.

Pastes

Disclosed herein, in certain embodiments, is a topical formulation of a fetal support tissue powder product disclosed herein wherein the topical formulation is in the form of a paste. In certain instances, pastes contain at least 20% solids. In certain instances, pastes are ointments that do not flow at body temperature.

Gels and Films

Disclosed herein, in certain embodiments, is a topical formulation of a fetal support tissue powder product disclosed herein wherein the topical formulation is in the form of a gel. In certain instances, gels are semisolid (or semi-rigid) systems consisting of dispersions of large organic molecules dispersed in a liquid. In certain instances, gels are water-soluble and are removed using warm water or saline.

In certain instances, in the treatment of dermal lesions, contacting lesions with a dressing can often disturb injured tissues. The removal of many dressings for wounds such as burns surface lesions that involve a significant area of the skin can cause significant pain and often can re-open at least portions of partially healed wounds. In some instances, a topical formulation of a fetal support tissue powder product disclosed herein is applied as a liquid to the affected area and the liquid gels as a film on the affected area. In some instances the film is a water soluble film and can be removed with water or a mild aqueous detergent, avoiding pain and discomfort associated with the removal of wound dressings. In certain instances, the topical formulation described herein is a dermal film comprising a flexible film made of a polyalkyloxazoline. In some instances, the film has a structural layer made of a polyalkyloxazoline and a pressure sensitive adhesive layer that keeps the film in place.

Sticks

Disclosed herein, in certain embodiments, is a topical formulation of a fetal support tissue powder product disclosed herein wherein the topical formulation is in the form of a stick. In certain instances, sticks are solid dosage forms that melt at body temperature. In some embodiments, a stick comprises a wax, a polymer, a resin, dry solids fused into a firm mass, and/or fused crystals. In some embodiments, a topical formulation of a fetal support tissue powder product disclosed herein is in the form of a styptic pencil (i.e., a stick prepared by (1) heating crystals until they lose their water of crystallization and become molten, and (2) pouring the molten crystals into molds and allowing them to harden). In some embodiments, a topical formulation of a fetal support tissue powder product disclosed herein is in the form of stick wherein the stick comprises a wax (e.g., the wax is melted and poured into appropriate molds in which they solidify in stick form).

In some embodiments, a topical formulation of a fetal support tissue powder product disclosed herein is in the form of stick wherein the stick comprises a melting base (i.e., a base that softens at body temperature). Examples of melting bases include, but are not limited to, waxes, oils, polymers and gels. In some embodiments, a topical formulation of a fetal support tissue powder product disclosed herein is in the form of stick wherein the stick comprises a moisten base (i.e., a base that is activated by the addition of moisture).

Patches

Disclosed herein, in certain embodiments, is a topical formulation of a fetal support tissue powder product disclosed herein wherein the topical formulation is administered via a patch. In some embodiments, a topical formulation of a fetal support tissue powder product disclosed herein is dissolved and/or dispersed in a polymer or an adhesive. In some embodiments, a film, a patch disclosed herein is constructed for continuous, pulsatile, or on demand delivery of a fetal support tissue powder product.

Wound Dressings

Disclosed herein, in certain embodiments, is a topical formulation of a fetal support tissue powder product disclosed herein wherein the topical formulation is administered with (or via) a wound dressing. Wound dressings include, but are not limited to gauzes, transparent film dressings, hydrogels, polyurethane foam dressings, hydrocolloids and alginates. In certain instances, wound dressings promote wound healing. In some instances, wound dressings reduce or inhibit aberrant wound healing.

Implants/Prosthesis

Disclosed herein, in certain embodiments, is an implant or prosthesis comprising a fetal support tissue powder product disclosed herein. In some embodiments, a fetal support tissue powder product disclosed herein is coated onto a medical implant (e.g., a stent). In some embodiments, a medical implant/fetal support tissue powder product disclosed herein is implanted into an individual in need thereof, wherein the fetal support tissue powder product is partially or fully released into the individual. In some embodiments, the prosthesis is an artificial joint. In some embodiments, the implant is a stent.

In some embodiments, the prosthesis is an artificial hip joint. In some embodiments, the fetal support tissue powder product is coated onto the outside of the artificial hip joint. In some embodiments, the fetal support tissue powder product elutes from the artificial hip into the surrounding tissue.

In some embodiments, the prosthesis is an artificial knee. In some embodiments, the fetal support tissue powder product is coated onto the outside of the artificial knee. In some embodiments, the fetal support tissue powder product elutes from the artificial knee into the surrounding tissue.

In some embodiments, the prosthesis is an artificial glenohumeral joint. In some embodiments, the fetal support tissue powder product is coated onto the outside of the artificial glenohumeral joint. In some embodiments, the fetal support tissue powder product elutes from the artificial glenohumeral joint into the surrounding tissue.

In some embodiments, the prosthesis is an artificial ankle. In some embodiments, the fetal support tissue powder product is coated onto the outside of the artificial ankle. In some embodiments, the fetal support tissue powder product elutes from the artificial ankle into the surrounding tissue.

In some embodiments, the implant is a coronary stent. In some embodiments, the fetal support tissue powder product is coated onto the outside of the stent. In some embodiments, the fetal support tissue powder product elutes from the stent into the surrounding cardiac tissue. In some embodiments, the stent is expandable or contractible.

In some embodiments, the implant is a ureteral stent. In some embodiments, the fetal support tissue powder product is coated onto the outside of the stent. In some embodiments, the fetal support tissue powder product elutes from the stent into the surrounding tissue. In some embodiments, the stent is expandable or contractible. In some embodiments, the implant is a urethral or prostatic stent. In some embodiments, the fetal support tissue powder product is coated onto the outside of the stent. In some embodiments, the fetal support tissue powder product elutes from the stent into the surrounding tissue. In some embodiments, the stent is expandable or contractible.

In some embodiments, the implant is an esophageal stent. In some embodiments, the fetal support tissue powder product is coated onto the outside of the stent. In some embodiments, the fetal support tissue powder product elutes from the stent into the surrounding tissue. In some embodiments, the stent is expandable or contractible.

In some embodiments, the implant is a bone implant. In some embodiments, the bone implant is an osseointegrated implant. As used herein, an "osseointegrated implant" means a three dimensional implant containing pores into which osteoblasts and supporting connective tissue can migrate. In some embodiments, the bone implant comprises a composition described herein. In some embodiments, the bone implant is a dental implant. In some embodiments, the bone implant is used for knee or joint replacement. In some embodiments, the bone implant is a craniofacial prosthesis (e.g., an artificial ear, orbital prosthesis, nose prosthesis).

In some embodiments, the implant is a bone stent. In some embodiments, the fetal support tissue powder product is coated onto the outside of the stent. In some embodiments, the fetal support tissue powder product elutes from the stent into the surrounding bone. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, the implant is a K-wire or Denham pin. In some embodiments, the fetal support tissue powder product is coated onto the outside of the K-wire or Denham pin. In some embodiments, the fetal support tissue powder product elutes from the K-wire or Denham pin into the surrounding bone.

Miscellaneous Formulations

In some embodiments, a fetal support tissue powder product disclosed herein is administered as a dermal paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the affected area of the skin of an individual. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers.

In certain embodiments, a fetal support tissue powder product described herein is optionally incorporated within controlled release particles, lipid complexes, liposomes, nanoparticles, microspheres, microparticles, nanocapsules or other agents which enhance or facilitate localized delivery to the skin. An example of a conventional microencapsulation process for pharmaceutical preparations is shown in U.S. Pat. No. 3,737,337, incorporated herein by reference for such disclosure.

In some instances, a fetal support tissue powder product described herein is a liposomal formulation. Liposomes are prepared by introducing an aqueous buffer into a mixture of phospholipid and organic solvent and the organic solvent is subsequently removed by evaporation under reduced pressure. An example of a liposomal preparation is described in *Proc. Natl. Acad. Sci.* 1978, 75, 4194-98, incorporated herein by reference for such disclosure. Liposomes are fractionated according to their particle sizes by size exclusion chromatography (SEC). The subfractions of liposomes are further sized by photon correlation spectroscopy (PCS) for their particle sizes. Enzymatic assays (e.g., phosphatidylcholine (PC) assay) are used to analyze lipid contents of liposomes.

Excipients

Disclosed herein, in certain embodiments, are formulations of a fetal support tissue powder product disclosed herein wherein the formulations comprise at least one component of a basement membrane matrix. Further disclosed herein, in certain embodiments, are formulations of a fetal support tissue powder product disclosed herein wherein the formulations comprise collagen, fibrin, hyaluronic acid, or any combinations thereof. In some embodiments, the formulations comprise collagen. In some embodiments, the compositions comprise fibrin. In some embodiments, the compositions comprise hyaluronic acid.

Carriers

Disclosed herein, in certain embodiments, are formulations of a fetal support tissue powder product disclosed herein wherein the formulations comprise a carrier. Suitable carriers include, but are not limited to, carbomer, cellulose, collagen, ethanol, glycerin, hexylene glycol, hyaluronic acid, hydroxypropyl cellulose, phosphoric acid, polyols (propyleneglycol, polyethylene-glycol, glycerol, cremophor and the like), polysorbate 80, saline, sodium hydroxide, sodium phosphate, sorbital, water, xanthan gum vegetable oils (such as olive oil), injectable organic esters (e.g., ethyl oleate), fatty oils (e.g., sesame oil), and synthetic fatty acid esters (e.g., ethyl oleate or triglycerides).

Penetration Enhancers

Disclosed herein, in certain embodiments, are formulations of a fetal support tissue powder product disclosed herein wherein the formulations comprise a penetration enhancer. Penetration enhancers include, but are not limited to, sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates, sodium glycocholate, sodium deoxycholate, sodium taurocholate, sodium taurodihydrofusidate, sodium glycodihydrofusidate, oleic acid, caprylic acid, mono- and di-glycerides, lauric acids, acylcholines, caprylic acids, acylcarnitines, sodium caprates, EDTA, citric acid, salicylates, DMSO, decylmethyl sulfoxide, ethanol, isopropanol, propylene glycol, polyethylene glycol, glycerol, propanediol, and diethylene glycol monoethyl ether. In certain embodiments, the topical formulations described herein are designed for minimal systemic exposure and include, for example, low amounts of penetration enhancers.

Gelling Agents

Disclosed herein, in certain embodiments, are formulations of a fetal support tissue powder product disclosed herein wherein the formulations comprise a gelling (or thickening) agent. In some embodiments, a formulation disclosed herein further comprises from about 0.1% to about 5%, from about 0.1% to about 3%, or from about 0.25% to about 2%, of a gelling agent. In certain embodiments, the viscosity of a formulation disclosed herein is in the range from about 100 to about 500,000 cP, about 100 cP to about 1,000 cP, about 500 cP to about 1500 cP, about 1000 cP to about 3000 cP, about 2000 cP to about 8,000 cP, about 4,000 cP to about 10,000 cP, about 10,000 cP to about 50,000 cP. Any suitable gelling agent may be used with the formulations disclosed herein. Suitable gelling agents include components of a basement membrane matrix. More particularly, suitable gelling agents for use in preparation of the gel formulation include, but are not limited to, collagen, fibrin, hyaluronic acid, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, mannitol, sorbitol, honey, maize starch, wheat starch, rice starch, potato starch, gelatin, sterculia gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof.

Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates).

Suitable agents for use in formulations that are applied as liquids and gel upon application to the skin into a film include but are not limited to polymers composed of polyoxypropylene and polyoxyethylene that are known to form thermoreversible gels when incorporated into aqueous solutions. These polymers have the ability to change from the liquid state to the gel state at temperatures close to body temperature, therefore allowing useful formulations that are applied as gels and/or films to the affected area. Examples of polymers that gel at body temperature and are used in gels and/or films described herein include and are not limited to poloxamers (e.g., PLURONICS F68®, F88®, F108®, and F127®, which are block copolymers of ethylene oxide and propylene oxide). The liquid state-to-gel state phase transition is dependent on the polymer concentration and the ingredients in the solution.

Adhesives

In some instances, a formulation described herein comprises pressure sensitive adhesives (e.g., polyalkyloxazoline polymers) and allows for application of an adhesive film to an affected area of skin.

Emollients

Disclosed herein, in certain embodiments, are formulations of a fetal support tissue powder product disclosed herein wherein the formulations comprise an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

Miscellaneous Excipients

In certain embodiments, a formulation comprising a fetal support tissue powder product disclosed herein comprises additional excipients such as, by way of example, abrasives, absorbents, anticaking agents, astringents, essential oils, fragrances, skin-conditioning agents, skin healing agents, skin protectants (e.g., sunscreens, or ultraviolet light absorbers or scattering agents), skin soothing agents, or combinations thereof.

Methods of Use

Disclosed herein, in certain embodiments, are methods of preparing a fetal support tissue powder product, comprising: (a) obtaining fetal support tissue; (b) lyophilizing the fetal support tissue to produce a lyophilized fetal support tissue; and (c) grinding the lyophilized fetal support tissue to generate a fetal support tissue powder. Disclosed herein, in certain embodiments, are methods of preparing a fetal support tissue powder product comprising (a) lyophilizing a fetal support tissue to produce a lyophilized fetal support tissue, and (b) grinding the lyophilized fetal support tissue to generate a fetal support tissue powder. Disclosed herein, in certain embodiments, are methods of preparing a fetal support tissue powder product comprising grinding a lyophilized fetal support tissue to generate a fetal support tissue powder. Disclosed herein, in certain embodiments, are methods of preparing a fetal support tissue powder product, comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate a fetal support tissue powder. Disclosed herein, in certain embodiments, are methods of preparing a fetal support tissue powder product comprising (a) freezing fetal support tissue to produce frozen fetal support tissue, (b) lyophilizing the frozen fetal support tissue to produce a lyophilized fetal support tissue, and (c) grinding the lyophilized fetal support tissue to generate a fetal support tissue powder. Disclosed herein, in certain embodiments, are methods of preparing a fetal support tissue powder product comprising (a) lyophilizing frozen fetal support tissue to produce a lyophilized fetal support tissue, and (b) grinding the lyophilized fetal support tissue to generate a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

Disclosed herein, in certain embodiments, are fetal support tissue powder products prepared by the method comprising: (a) obtaining fetal support tissue; (b) lyophilizing the fetal support tissue to produce a lyophilized fetal support tissue; and (c) grinding the lyophilized fetal support tissue to generate fetal support tissue powder. Disclosed herein, in certain embodiments, are fetal support tissue powder products prepared by the method comprising (a) lyophilizing a fetal support tissue to produce a lyophilized fetal support tissue, and (b) grinding the lyophilized fetal support tissue to produce a fetal support tissue powder. Disclosed herein, in certain embodiments, are fetal support tissue powder products prepared by the method comprising grinding a lyophilized fetal support tissue. Disclosed herein, in certain embodiments, are fetal support tissue powder products prepared by the method comprising: (a) obtaining fetal support tissue; (b) freezing fetal support tissue to produce frozen fetal support tissue, (c) lyophilizing the frozen fetal support tissue to produce a lyophilized fetal support tissue; and (d) grinding the lyophilized fetal support tissue to generate fetal support tissue powder. Disclosed herein, in certain embodiments, are fetal support tissue powder products prepared by the method comprising (a) freezing fetal support tissue to produce frozen fetal support tissue, (b) lyophilizing the frozen fetal support tissue to produce a lyophilized fetal support tissue, and (c) grinding the lyophilized fetal support tissue to produce a fetal support tissue powder. Disclosed herein, in certain embodiments, are fetal support tissue powder products prepared by the method comprising (a) lyophilizing frozen fetal support tissue to produce a lyophilized fetal support tissue, and (c) grinding the lyophilized fetal support tissue to produce a fetal support tissue powder. In some embodiments, the fetal support tissue is (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof.

In some embodiments, a fetal support tissue powder product disclosed herein is used to inhibit at least one of the following: scarring, inflammation, adhesion and angiogenesis. In some embodiments, a fetal support tissue powder product disclosed herein is used to promote wound healing. In some embodiments, the use is a homologous use. In some embodiments, a fetal support tissue powder product disclosed herein is minimally manipulated. In some embodiments, a fetal support tissue powder product disclosed herein does not comprise another article, except for water, crystalloids, or a sterilizing, preserving, or storage agent. In some embodiments, a fetal support tissue powder product disclosed herein does not have a systemic effect and is not dependent upon the metabolic activity of living cells for its primary function.

In some embodiments, a fetal support tissue powder product disclosed herein is used as a covering (e.g., a wound covering). In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein is used to promote wound repair. In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein is used as a barrier to adhesion. In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein comprises proteins, glycans, protein-glycan complexes (e.g., a complex of hyaluronic acid and a heavy chain of IαI and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in a fetal support tissue powder product disclosed herein diffuse out of the fetal support tissue powder product and into the surrounding tissue.

In some embodiments, a fetal support tissue powder product disclosed herein is used to treat inflammation. In some embodiments, a fetal support tissue powder product disclosed herein is used to treat inflammation associated with an autoimmune disorder. In some embodiments, a fetal support tissue powder product disclosed herein is used to treat inflammation associated with Acute coronary syndrome; Acute disseminated encephalomyelitis; Acute respiratory distress syndrome (ARDS); Addison's disease; AIDS dementia; Allergic rhinitis; Alzheimer's disorder; Ankylosing spondylitis; Antiphospholipid antibody syndrome; Asthma; Atherosclerosis; Atopic dermatitis; Autoimmune hemolytic anemia; Autoimmune hepatitis; Autoimmune inner ear disease; Behcet's syndrome; Bronchitis; Bullous pemphigoid; Cardiac-allograft vasculopathy; Chagas disease; Chronic obstructive pulmonary disease; Coagulative Necrosis; Coeliac disease; Collagenous colitis; Conjunctivitis; Crohn's disorder; Cystic fibrosis; Dermatomyositis; Dermatitis; Diabetes mellitus type 1; Diabetes mellitus type 2; Distal proctitis; Diversion colitis; Dry eye; Eczema; Encephalitis; Endometriosis; Endotoxic shock; Epilepsy; Fibrinoid Necrosis; Fibromyalgia; Gastroenteritis; Goodpasture's syndrome; Gouty arthritis; Graft-versus-host disease; Graves' disease; Guillain-Barré syndrome; Hashimoto's disease; Idiopathic thrombocytopenic purpura; Indeterminate colitis; Infective colitis; Inflammatory liver disorder; Interstitial cystitis; Ischaemic colitis; Liquefactive Necrosis; Lymphocytic colitis; Meningitis; Metabolic syndrome; Moyamoya disease; Multiple sclerosis; Myasthenia gravis; Myocarditis; Myocardial infarction; Narcolepsy; Nasal polyps; Neointimal hyperplasia; Nephritis; Obesity; Parkinson's disorder; Pemphigus Vulgaris; Pancreatitis; Periodontal gingivitis; Pernicious anaemia; Polymyositis; Polymyalgia rheumatica; Primary biliary cirrhosis; Psoriasis; Pulmonary fibrosis; Pulmonary inflammation; Rheumatoid arthritis; Rheumatoid spondylitis; Retinitis; Schizophrenia; Scleroderma; Septic shock; Shingles; Sjögren's syndrome; Stroke; Systemic lupus erythematosus (SLE); Takayasu disease; Tuberculosis; Ulcerative colitis; Uveitis; Vasculitis; Vitiligo; Wegener's granulomatosis; Prostate cancer; Non-small cell lung carcinoma; Ovarian cancer; Breast cancer; Melanoma; Gastric cancer; Colorectal cancer; Brain cancer; Metastatic bone disorder; Pancreatic cancer; a Lymphoma; Gastrointestinal cancer; or combinations thereof. In some embodiments, a fetal support tissue powder product disclosed herein is used to treat inflammation associated with dry eye, graft-versus-host disease, Crohn's disease, myocardial infarction, type I diabetes, or gastroenteritis.

In some embodiments, a fetal support tissue powder product disclosed herein is used to treat inflammation associated with Acute coronary syndrome; Atopic dermatitis; Crohn's disorder; Dermatitis; Diabetes mellitus type 1; Dry eye; Endotoxic shock; Graft-versus-host disease; Psoriasis; Rheumatoid arthritis; Rheumatoid spondylitis; Periodontitis; or any combination thereof. In some embodiments, a fetal support tissue powder product disclosed herein is used to treat inflammation associated with Acute coronary syndrome. In some embodiments, a fetal support tissue powder product disclosed herein is used to treat inflammation associated with Atopic dermatitis. In some embodiments, a fetal support tissue powder product disclosed herein is used to treat inflammation associated with Crohn's disorder. In some embodiments, a fetal support tissue powder product disclosed herein is used to treat inflammation associated with Dermatitis. In some embodiments, a fetal support tissue powder product disclosed herein is used to treat inflammation associated with Diabetes mellitus type 1. In some embodiments, a fetal support tissue powder product disclosed herein is used to treat inflammation associated with Dry eye. In some embodiments, a fetal support tissue powder product disclosed herein is used to treat inflammation associated with Endotoxic shock. In some embodiments, a fetal support tissue powder product disclosed herein is used to treat inflammation associated with Graft-versus-host disease. In some embodiments, a fetal support tissue powder product disclosed herein is used to treat inflammation associated with Psoriasis. In some embodiments, a fetal support tissue powder product disclosed herein is used to treat inflammation associated with Rheumatoid arthritis. In some embodiments, a fetal support tissue powder product disclosed herein is used to treat inflammation associated with Rheumatoid spondylitis. In some embodiments, a fetal support tissue powder product disclosed herein is used to treat inflammation associated with Periodontitis.

Injured Tissue Repair and Supplementation

In some embodiments, a fetal support tissue powder product disclosed herein is used as a wound covering or is used to facilitate wound repair. In some embodiments, the use is a homologous use (e.g., a functional homologous use or a structural homologous use). In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, the tissue was damaged, compromised, or lost due to an injury (e.g., a burn; a surgical incision; an area of necrosis resulting from an infection, trauma, or a toxin; a laceration). In some embodiments, the tissue was damaged, compromised, or lost due to a burn. In some embodiments, the tissue was damaged, compromised, or lost due to a wound (e.g., an incision, laceration, abrasion). In some embodiments, the tissue was damaged, compromised, or lost due to necrosis. In some embodiments, the tissue was damaged, compromised, or lost due to ulceration.

In some embodiments, a fetal support tissue powder product disclosed herein comprises proteins, glycans, protein-glycan complexes (e.g., a complex of hyaluronic acid and a heavy chain of IαI and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in a fetal support tissue powder product disclosed herein diffuse out of the fetal support tissue powder product and into the surrounding tissue.

Burns

In some embodiments, a fetal support tissue powder product disclosed herein is applied to a burn. In some embodiments, a fetal support tissue powder product disclosed herein is applied to a first degree burn. In some embodiments, a fetal support tissue powder product disclosed herein is applied to a second degree burn. In some embodiments, a fetal support tissue powder product disclosed herein is applied to a third degree burn. In some embodiments, the fetal support tissue powder product is applied to a substrate prior to be placed on the burn.

Wounds

In some embodiments, a fetal support tissue powder product disclosed herein is applied to a wound in the skin (e.g., an incision, laceration, abrasion, ulcer, puncture, or penetration). In some embodiments, the fetal support tissue powder product is applied to a substrate prior to being placed on the wound.

In some embodiments, a fetal support tissue powder product disclosed herein is applied to an incision in an organ (e.g., the skin, brain, stomach, kidneys, liver, intestines, lungs, bladder, trachea, esophagus, vagina, ureter, and blood vessel walls). In some embodiments, a fetal support tissue powder product disclosed herein is applied to a surgical incision. In some embodiments, a fetal support tissue powder product disclosed herein is applied to the site of a colon resection. In some embodiments, a fetal support tissue powder product disclosed herein is applied to the site of a gastrectomy. In some embodiments, a fetal support tissue powder product disclosed herein is applied to the site of a breast surgery (e.g., breast reduction surgery, breast augmentation surgery, and mastectomy). In some embodiments, the fetal support tissue powder product is applied to a substrate prior to being placed on the wound.

In some embodiments, a fetal support tissue powder product disclosed herein is used as a covering over an incision in the skin (e.g., an incision to the epidermis, dermis, and/or hypodermis). In some embodiments, a fetal support tissue powder product disclosed herein is used to repair or supplement the skin following hemorrhoid surgery. In some embodiments, the fetal support tissue powder product is applied to a substrate prior to being placed on the wound.

Necrosis

In some embodiments, a fetal support tissue powder product disclosed herein is used as a protective graft over an area of necrotic tissue (e.g., from an infection). In some embodiments, a fetal support tissue powder product disclosed herein is used as a protective graft over an area of necrotic skin. In some embodiments, a fetal support tissue powder product disclosed herein is placed on an area of necrotic tissue. In some embodiments, the fetal support tissue powder product is applied to a substrate prior to being placed on the necrotic tissue.

Ulcer

In some embodiments, a fetal support tissue powder product disclosed herein is used as a protective covering over an ulcer. In some embodiments, the fetal support tissue powder product is applied to a substrate prior to being placed on the ulcer.

In some embodiments, the ulcer is a foot ulcer (e.g., a diabetic foot ulcer or an arterial insufficiency ulcer). In some embodiments, treating a foot ulcer comprises (a) preparing the wound (e.g., debriding the wound); and (b) placing a fetal support tissue powder product disclosed herein on the wound. In some embodiments, treating a foot ulcer comprises (a) preparing the wound (e.g., debriding the wound); (b) placing a fetal support tissue powder product disclosed herein on the wound; and (c) covering the fetal support tissue powder product with a protective barrier (e.g., a silvercell dressing, metipel, gauze, or a bandage). In some embodiments, the fetal support tissue powder product is applied to a substrate prior to be placed on the ulcer.

In some embodiments, the ulcer is a venous stasis (VS) ulcer. In some embodiments, treating a VS ulcer comprises (a) preparing the wound (e.g., debriding the wound); and (b) placing A fetal support tissue powder product disclosed herein on the wound. In some embodiments, treating a VS ulcer comprises (a) preparing the wound (e.g., debriding the wound); (b) placing a fetal support tissue powder product disclosed herein on the wound; and (c) covering the fetal support tissue powder product with a protective barrier (e.g., a wound veil, antimicrobial dressing, gauze, or a bandage). In some embodiments, the fetal support tissue powder product is applied to a substrate prior to being placed on the wound.

In some embodiments, the ulcer is a corneal ulcer (i.e., ulcerative keratitis). In some embodiments, treating a corneal ulcer comprises (a) preparing the wound (e.g., debriding the wound); and (b) placing a fetal support tissue powder product disclosed herein on the wound. In some embodiments, treating a corneal ulcer comprises (a) preparing the wound (e.g., debriding the wound); (b) placing a fetal support tissue powder product disclosed herein on the wound; and (c) covering the fetal support tissue powder product or fetal support tissue powder product with a protective barrier (e.g., a contact lens or a bandage). In some embodiments, the fetal support tissue powder product is applied to a substrate prior to being placed on the wound.

Soft Tissue Uses

Disclosed herein, in certain embodiments, is the use of a fetal support tissue powder product disclosed herein for repairing, reconstructing, replacing, or supplementing a recipient's damaged, compromised, or missing soft tissue (e.g., tendons).

In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein comprises proteins, glycans, protein-glycan complexes (e.g., a complex of hyaluronic acid and a heavy chain of IαI and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in a fetal support tissue powder product disclosed herein diffuse out of the fetal support tissue powder product and into the surrounding tissue.

In some embodiments, a fetal support tissue powder product disclosed herein described herein is used as a covering over an incision in soft tissue (e.g., eyelids form the tissue plane between different layers of soft tissue). In some embodiments, the fetal support tissue powder product is applied to a substrate and then used as a covering over an incision in soft tissue (e.g., eyelids form the tissue plane between different layers of soft tissue).

In some embodiments, a fetal support tissue powder product disclosed herein is used as structural (tectonic) support for soft tissue.

In some embodiments, a fetal support tissue powder product disclosed herein prevents adhesion in joint or tendon repairs.

In some embodiments, a fetal support tissue powder product disclosed herein is used in the repair of a tendon or joint (such as rotator cuff repairs, hand tendon repairs). In some embodiments, a fetal support tissue powder product disclosed herein is used to reinforce a tendon or joint. In some embodiments, a fetal support tissue powder product disclosed herein is used to prevent adhesion of a healing tendon to surrounding tissue, tendons or joints. In some embodiments, a fetal support tissue powder product disclosed herein is used to prevent the formation of scar tissue on a tendon.

In some embodiments, a fetal support tissue powder product disclosed herein is applied to a substrate and the substrate/fetal support tissue powder product is used to augment smaller tendons and ligaments of the foot and ankle, including the posterior tibial tendon, the personneal tendons, the flexor and extensor tendons, and the ligaments of the lateral ankle complex. In some embodiments, a fetal support tissue powder product disclosed herein is applied to a substrate and the substrate/fetal support tissue powder product is used to reinforce primary repair of the quadriceps and patellar tendons surrounding the knee. In some embodiments, a fetal support tissue powder product disclosed herein is applied to a substrate and the substrate/fetal support tissue powder product is used as a periosteal patch for bone graft in joint replacement. In some embodiments, a fetal support tissue powder product disclosed herein is applied to a substrate and the substrate/fetal support tissue powder product is used to augment deficient hip and knee capsular tissue following total joint revision surgery.

In some embodiments, a fetal support tissue powder product disclosed herein is applied to a substrate and the substrate/fetal support tissue powder product is used in the repair of a torn rotator cuff In some embodiments, a fetal support tissue powder product disclosed herein is applied to a substrate and the substrate/fetal support tissue powder product is used as a patch over a rotator cuff muscle or tendon (e.g., the supraspinatus tendon). In some embodiments, a fetal support tissue powder product disclosed herein is applied to a substrate and the substrate/fetal support tissue powder product is used to reconstruct a rotator cuff muscle or tendon (e.g., the supraspinatus tendon). In some embodiments, a fetal support tissue powder product disclosed herein is applied to a substrate and the substrate/fetal support tissue powder product is used to augment a rotator cuff muscle or tendon (e.g., the supraspinatus tendon). In some embodiments, a fetal support tissue powder product disclosed herein is applied to a substrate and the substrate/fetal support tissue powder product is used to reinforce a rotator cuff muscle or tendon (e.g., the supraspinatus tendon). In some embodiments, a fetal support tissue powder product disclosed herein is applied to a substrate and the substrate/fetal support tissue powder product is used to prevent adhesion of soft tissue to a rotator cuff muscle or tendon (e.g., the supraspinatus tendon).

In some embodiments, a fetal support tissue powder product disclosed herein is used in the repair gingiva. In some embodiments, a fetal support tissue powder product disclosed herein is used in the repair gingival recession. In some embodiments, a fetal support tissue powder product disclosed herein is applied to a substrate and used as a patch over gingiva. In some embodiments, a fetal support tissue powder product disclosed herein is applied to substrate and used as a patch over an exposed tooth root surface. In some embodiments, a fetal support tissue powder product disclosed herein is used to reconstruct gingiva. In some embodiments, a fetal support tissue powder product disclosed herein is used to augment gingiva. In some embodiments, a fetal support tissue powder product disclosed herein is used to reinforce gingiva. In some embodiments, a fetal support tissue powder product disclosed herein is used to prevent adhesion of soft tissue to gingiva.

In some embodiments, a fetal support tissue powder product described herein is applied to a substrate and the substrate/fetal support tissue powder product is used as a protective graft over an incision or tear in the fascia. In some embodiments, a fetal support tissue powder product disclosed herein is applied to a substrate and the substrate/fetal support tissue powder product is used as structural (tectonic) support the fascia. In some embodiments, a fetal support tissue powder product disclosed herein is applied to a substrate and the substrate/fetal support tissue powder product is used as a replacement or supplement for the fascia. In some embodiments, a fetal support tissue powder product disclosed herein is applied to a substrate and the substrate/fetal support tissue powder product is used to repair a hernia (e.g., to repair the fascia). In some embodiments, a fetal support tissue powder product disclosed herein is applied to a substrate and the substrate/fetal support tissue powder product is used to repair an inguinal hernia. In some embodiments, a fetal support tissue powder product disclosed herein is applied to a substrate and the substrate/fetal support tissue powder product is used to repair a femoral hernia. In some embodiments, a fetal support tissue powder product disclosed herein is applied to a substrate and the substrate/fetal support tissue powder product is used to repair an umbilical hernia. In some embodiments, a fetal support tissue powder product disclosed herein is applied to a substrate and the substrate/fetal support tissue powder product is used to repair an incisional hernia. In some embodiments, a fetal support tissue powder product disclosed herein is applied to a substrate and the substrate/fetal support tissue powder product is used to repair a diaphragmatic hernia. In some embodiments, a fetal support tissue powder product disclosed herein is applied to a substrate and the substrate/fetal support tissue powder product is used to repair a Cooper's hernia, an epigastric hernia, an hiatal hernia, a Littre's hernia, a lumbar hernia, a maydl hernia, an obturator hernia, a pantaloon hernia, a paraesophageal hernia, a paraumbilical hernia, a perineal hernia, a properitoneal hernia, a Richter's hernia, a sliding hernia, a sciatic hernia, a spigelian hernia, a sports hernia, a Velpeau hernia, or a Amyand's hernia.

In some embodiments, a fetal support tissue powder product disclosed herein is applied to a substrate and the substrate/fetal support tissue powder product is used to repair a spinal disc herniation. In some embodiments, a fetal support tissue powder product disclosed herein is applied to a substrate and the substrate/fetal support tissue powder product is used as a protective graft over an incision or tear in a spinal disc. In some embodiments, a fetal support tissue powder product disclosed herein is applied to a substrate and the substrate/fetal support tissue powder product is used as a protective graft over an incision or tear in an annulus fibrosis. In some embodiments, a fetal support tissue powder product disclosed herein is applied to a substrate and the substrate/fetal support tissue powder product is used as structural (tectonic) support a spinal disc. In some embodiments, a fetal support tissue powder product disclosed herein is applied to a substrate and the substrate/fetal support tissue powder product is used as structural (tectonic) support an annulus fibrosis. In some embodiments, a fetal support tissue powder product disclosed herein is applied to a substrate and the substrate/fetal support tissue powder product is used as a replacement or supplement for a spinal disc. In some embodiments, a fetal support tissue powder product disclosed herein is applied to a substrate and the substrate/fetal support tissue powder product is used as structural (tectonic) support a spinal disc. In some embodiments, a fetal support tissue powder product disclosed herein is applied to a substrate and the substrate/fetal support tissue powder product is used as a replacement or supplement for an annulus fibrosis.

In some embodiments, a fetal support tissue powder product disclosed herein is applied to a substrate and the substrate/fetal support tissue powder product is used over an incision in the brain, or in one (or all) of the meninges (i.e., the dura mater, the pia mater, and/or the arachnoid mater). In some embodiments, a fetal support tissue powder product disclosed herein is applied to a substrate and the substrate/fetal support tissue powder product is used as structural (tectonic) support for one (or all) of the meninges (i.e., the dura mater, the pia mater, and/or the arachnoid mater). In some embodiments, a fetal support tissue powder product disclosed herein is applied to a substrate and the substrate/fetal support tissue powder product is used as a replacement for one (or all) of the meninges (i.e., the dura mater, the pia mater, and/or the arachnoid mater).

In some embodiments, a fetal support tissue powder product disclosed herein is applied to a substrate and the substrate/fetal support tissue powder product is used over an incision in a lung or in the pleura. In some embodiments, a fetal support tissue powder product disclosed herein is applied to a substrate and the substrate/fetal support tissue powder product is used as structural (tectonic) support for the pleura. In some embodiments, a fetal support tissue powder product disclosed herein is applied to a substrate and the substrate/fetal support tissue powder product is used as a replacement for the pleura.

In some embodiments, a fetal support tissue powder product disclosed herein is applied to a substrate and the substrate/fetal support tissue powder product is used over an incision in a tympanic membrane. In some embodiments, a fetal support tissue powder product disclosed herein is applied to a substrate and the substrate/fetal support tissue powder product is used as structural (tectonic) support for a tympanic membrane. In some embodiments, a fetal support tissue powder product disclosed herein is applied to a substrate and the substrate/fetal support tissue powder product is used as a replacement for a tympanic membrane.

In some embodiments, a fetal support tissue powder product disclosed herein is applied to a substrate and the substrate/fetal support tissue powder product is used as a protective graft over an incision in the heart or the pericardium. In some embodiments, a fetal support tissue powder product disclosed herein is applied to a substrate and the substrate/fetal support tissue powder product is used as structural (tectonic) support for the pericardium. In some embodiments, a fetal support tissue powder product disclosed herein is applied to a substrate and the substrate/fetal support tissue powder product is used as a replacement for the pericardium.

In some embodiments, a fetal support tissue powder product disclosed herein is applied to a substrate and the substrate/fetal support tissue powder product is used as a protective graft over an incision in the peritoneum. In some embodiments, a fetal support tissue powder product disclosed herein is applied to a substrate and the substrate/fetal support tissue powder product is used as structural (tectonic) support for the peritoneum. In some embodiments, a fetal support tissue powder product disclosed herein is applied to a substrate and the substrate/fetal support tissue powder product is used as a replacement for the peritoneum.

Ophthalmic Uses

Disclosed herein, in certain embodiments, is the use of a fetal support tissue powder product disclosed herein for repairing, reconstructing, replacing, or supplementing a recipient's damaged, compromised, or missing ocular tissue.

In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product disclosed herein does not have a systemic effect and is not dependent upon the metabolic activity of living cells for its primary function.

In some embodiments, a fetal support tissue powder product disclosed herein comprises proteins, glycans, protein-glycan complexes (e.g., a complex of hyaluronic acid and a heavy chain of I$\alpha$I and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in a fetal support tissue powder product disclosed herein diffuse out of the fetal support tissue powder product and into the surrounding tissue.

Treatment of Glaucoma

As used herein, "Glaucoma" means a disorder characterized by the loss of retinal ganglion cells in the optic nerve. In certain instances, glaucoma partially or fully results from an increase in intraocular pressure in the anterior chamber (AC). Intraocular pressure varies depending on the production of liquid aqueous humor by the ciliary processes of the eye and the drainage of the aqueous humor through the trabecular meshwork.

Glaucoma Drainage Devices (GDD) are medical devices that are implanted into an eye to relieve intraocular pressure by providing an alternative pathway for the aqueous humor to drain. If left uncovered, a GDD tube will erode and leave the eye susceptible to intraocular infection. Thus, the GDD tube needs to be covered. Currently, patches used to cover GDD tubes are made from pericardium, sclera and cornea. These patches are about 400-550 microns thick. The thinness of these patches results in their melting by 25% in 2 years potentially leaving the shunt tube exposed again.

In some embodiments, a fetal support tissue powder product disclosed herein is applied to a substrate and the substrate/fetal support tissue powder product is used to cover GDD tubes. In some embodiments, the substrate/fetal support tissue powder product is 300-600 microns thick. In some embodiments, the substrate/fetal support tissue powder product does not melt by 25% in 2 years.

Treatment of Ocular Ulcers

In some embodiments, a fetal support tissue powder product disclosed herein is applied to a substrate and the substrate/fetal support tissue powder product is used to cover persistent epithelial defects and/or ulcers in eyes.

In some embodiments, the base of the ulcer is debrided with surgical sponges and the poorly adherent epithelium adjacent to the edge of the ulcer is removed (e.g., to the section of the eye where the epithelium becomes quite adherent). In some embodiments, a fetal support tissue powder product disclosed herein is applied to a substrate and the substrate/fetal support tissue powder product is transferred to the recipient eye. In some embodiments, a fetal support tissue powder product disclosed herein is applied to a substrate and the substrate/fetal support tissue powder product is then secured to the eye by sutures (e.g., interrupted 10-0 nylon sutures or running 10-0 nylon sutures) with the suture knots being buried. In some embodiments, a fetal support tissue powder product disclosed herein is applied to a substrate and the substrate/fetal support tissue powder product is secured to the eye by use of fibrin glue. In some embodiments, a protective layer is applied over the fetal support tissue powder product/substrate or the entire eye (e.g., a contact lens). In some embodiments, the substrate/fetal support tissue powder product further comprises an antibiotic (e.g., neomycin, polymyxin b sulfate and dexamethasone).

Conjunctival, Scleral, Lid, and Orbital Rim Surface Reconstruction

In some embodiments, a fetal support tissue powder product disclosed herein is applied to a substrate and the substrate/fetal support tissue powder product is used in conjunctival, scleral, lid, and orbital rim surface reconstruction. In some embodiments, damage to the conjunctival surface results from symblepharon lysis; surgical removal of tumor, lesion, and/or scar tissue; excimer laser photorefractive keratectomy and therapeutic keratectomy; or combinations thereof.

Coronary Uses

Disclosed herein, in certain embodiments, is the use of a fetal support tissue powder product disclosed herein for repairing, reconstructing, replacing, or supplementing a recipient's damaged, compromised, or missing coronary tissue In some embodiments, the use is a homologous use. In some embodiments, the fetal support tissue powder product is minimally manipulated. In some embodiments, the AM does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein comprises proteins, glycans, protein-glycan complexes (e.g., a complex of hyaluronic acid and a heavy chain of IαI and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in the fetal support tissue powder product diffuse out of the fetal support tissue powder product and into the surrounding tissue.

Coronary Artery Bypass

Disclosed herein, is the use of a fetal support tissue powder product described herein in coronary artery bypass surgery. In some embodiments, a fetal support tissue powder product disclosed herein is applied to a substrate and the substrate/fetal support tissue powder product is grafted onto a coronary artery to bypass a section of the artery that is characterized by atherosclerosis.

Heart Valves

In some embodiments, a fetal support tissue powder product disclosed herein is applied to a substrate and the substrate/fetal support tissue powder product is applied over a heart valve. In some embodiments, a fetal support tissue powder product disclosed herein is applied to a substrate and the substrate/fetal support tissue powder product is used as structural (tectonic) support for a heart valve. In some embodiments, a fetal support tissue powder product disclosed herein is applied to a substrate and the substrate/fetal support tissue powder product is used as a replacement for a heart valve.

Veins and Arteries

In some embodiments, a fetal support tissue powder product disclosed herein is applied to a substrate and the substrate/fetal support tissue powder product is applied to a vein or artery. In some embodiments, a fetal support tissue powder product disclosed herein is applied to a substrate and the substrate/fetal support tissue powder product is used as structural (tectonic) support for a vein or artery.

Nerve Uses

Disclosed herein, in certain embodiments, is the use of a fetal support tissue powder product disclosed herein for repairing, reconstructing, replacing, or supplementing a recipient's damaged, compromised, or missing nerve tissue.

In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein comprises proteins, glycans, protein-glycan complexes (e.g., a complex of hyaluronic acid and a heavy chain of IαI and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in a fetal support tissue powder product disclosed herein diffuse out of the fetal support tissue powder product and into the surrounding tissue.

In some embodiments, a fetal support tissue powder product disclosed herein is applied to a substrate and the substrate/fetal support tissue powder product is used as a covering over a nerve (e.g., a peripheral nerve). In some embodiments, a fetal support tissue powder product disclosed herein is applied to a substrate and the substrate/fetal support tissue powder product is used as a covering over a nerve graft, nerve transfer, or a repaired nerve. In some embodiments, a fetal support tissue powder product disclosed herein is applied to a substrate and the substrate/fetal support tissue powder product is used as a covering over an incision in a nerve (e.g., a peripheral nerve). In some embodiments, a fetal support tissue powder product disclosed herein is applied to a substrate and the substrate/fetal support tissue powder product is used as structural (tectonic) support for a nerve (e.g., a peripheral nerve). In some embodiments, a fetal support tissue powder product disclosed herein prevents adhesion in nerve repair.

In some embodiments, a fetal support tissue powder product disclosed herein is applied to a substrate and the substrate/fetal support tissue powder product is used as a non-constricting encasement for injured nerves. In some embodiments, a fetal support tissue powder product described herein prevents or minimizes scar formation, encapsulation, chronic compression, tethering of a nerve, and nerve entrapment. In some embodiments, a fetal support tissue powder product described herein prevents or minimizes neuroma formation. In some embodiments, a fetal support tissue powder product described herein prevents or minimizes the migration of endogenous growth factors (i.e. Nerve Growth Factor) present during nerve repair.

Spinal Uses

Disclosed herein, in certain embodiments, is the use of a fetal support tissue powder product described herein during spinal surgery.

In some embodiments, a fetal support tissue powder product described herein is used during a laminectomy. In some embodiments, the use is a homologous use. In some embodiments, the fetal support tissue powder product is minimally manipulated. In some embodiments, the fetal support tissue powder product does not comprise another article, except for water, crystalloids, or a sterilizing, preserving, or storage agent. In some embodiments, the fetal support tissue powder product does not have a systemic effect and is not dependent upon the metabolic activity of living cells for its primary function.

In some embodiments, a fetal support tissue powder product disclosed herein comprises proteins, glycans, protein-glycan complexes (e.g., a complex of hyaluronic acid and a heavy chain of IαI and PTX3) and enzymes that promote tissue repair. For example, the stroma of AM contains growth factors, anti-angiogenic and anti-inflammatory proteins, as well as natural inhibitors to various proteases. In some embodiments, proteins and enzymes found in a fetal support tissue powder product disclosed herein diffuse out of the fetal support tissue powder product and into the surrounding tissue.

In some embodiments, a fetal support tissue powder product described herein is used to reduce or prevent epidural fibrosis and/or scar adhesions following spinal surgery (e.g., laminectomy). In some embodiments, a fetal support tissue powder product described herein is implanted between dura mater and overlying tissue following spinal surgery (e.g., laminectomy). In some embodiments, implanting a fetal support tissue powder product described herein between dura mater and overlying tissue following spinal surgery (e.g., laminectomy) reduces or prevents migration of fibroblasts to the dura mater and collagen deposition on the dura mater.

In some embodiments, a fetal support tissue powder product described herein is used to reduce or prevent the development of proliferative scarring following spinal surgery (e.g., laminectomy). In some embodiments, a fetal support tissue powder product described herein is used to reduce or prevent the development of a postoperative (e.g., postlaminectomy) epidural/peridural/perineural scar. In some embodiments, a fetal support tissue powder product described herein is used to reduce or prevent the development of proliferative scarring following spinal surgery (e.g., laminectomy). In some embodiments, a fetal support tissue powder product disclosed herein is used to reduce or prevent the development of a postlaminectomy membrane.

In some embodiments, a fetal support tissue powder product described herein is used to reduce or prevent the development of extradural compression or dural tethering following spinal surgery (e.g., laminectomy). In some embodiments, a fetal support tissue powder product described herein is used to reduce or prevent the development of tethered nerve roots following spinal surgery (e.g., laminectomy). In some embodiments, a fetal support tissue powder product described herein is used to reduce or prevent the development of arachnoiditis following spinal surgery (e.g., laminectomy).

In some embodiments, a fetal support tissue powder product disclosed herein further comprises morcelized bone tissue. In some embodiments, a fetal support tissue powder product disclosed herein comprising morcelized bone tissue is used during a spinal fusion procedure. In some embodiments, a fetal support tissue powder product disclosed herein comprising morcelized bone tissue is implanted between adjacent vertebrae. In some embodiments, implantation of a fetal support tissue powder product disclosed herein comprising morcelized bone tissue between two adjacent vertebrae promotes fusion of the vertebrae.

In some embodiments, a fetal support tissue powder product disclosed herein is used as a protective graft over an incision in the dura mater. In some embodiments, a fetal support tissue powder product disclosed herein is applied to a substrate and the substrate/fetal support tissue powder product is used as structural (tectonic) support for the dura mater. In some embodiments, a fetal support tissue powder product disclosed herein is applied to a substrate and the substrate/fetal support tissue powder product is used as a replacement for the dura mater.

Bone Uses

In some embodiments, a fetal support tissue powder product disclosed herein is used to inhibit bone resorption in an individual in need thereof. In some embodiments, the individual has arthritis, osteoporosis, alveolar bone degradation, Paget's disease, or a bone tumor. In some embodiments, the fetal support tissue powder product is injected into a joint. In some embodiments, the fetal support tissue powder product is contacted with a bone (e.g., by use of a wound dressing or bandage). In some embodiments, the fetal support tissue powder product coats a bone stent, bone implant, or bone prosthesis (e.g., an osseointegrated implant). As used herein, an "osseointegrated implant" means a three dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a fetal support tissue powder product disclosed herein is used to promote or induce bone formation in an individual in need thereof in an individual in need thereof. In some embodiments, the individual has arthritis, osteoporosis, alveolar bone degradation, Paget's disease, or a bone tumor. In some embodiments, the fetal support tissue powder product is injected into a joint. In some embodiments, the fetal support tissue powder product is contacted with a bone (e.g., by use of a wound dressing or bandage). In some embodiments, the fetal support tissue powder product coats a bone stent, bone implant, or bone prosthesis (e.g., an osseointegrated implant). As used herein, an "osseointegrated implant" means a three dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a fetal support tissue powder product disclosed herein is used to inhibit osteoclast differentiation. In some embodiments, the individual has arthritis, osteoporosis, alveolar bone degradation, Paget's disease, or a bone tumor. In some embodiments, the fetal support tissue powder product is injected into a joint. In some embodiments, the fetal support tissue powder product is contacted with a bone (e.g., by use of a wound dressing or bandage). In some embodiments, the fetal support tissue powder product coats a bone stent, bone implant, or bone prosthesis (e.g., an osseointegrated implant). As used herein, an "osseointegrated implant" means a three dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a fetal support tissue powder product disclosed herein is used to promote mineralization by osteoblasts in an individual in need thereof. In some embodiments, the individual has arthritis, osteoporosis, alveolar bone degradation, Paget's disease, or a bone tumor. In some embodiments, the fetal support tissue powder product is injected into a joint. In some embodiments, the fetal support tissue powder product is contacted with a bone (e.g., by use of a wound dressing or bandage). In some embodiments, the fetal support tissue powder product coats a bone stent, bone implant, or bone prosthesis (e.g., an osseointegrated implant). As used herein, an "osseointegrated implant" means a three dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a fetal support tissue powder product disclosed herein is used to balance bone resorption and bone formation in an individual in need thereof. In some embodiments, the individual has arthritis, osteoporosis, alveolar bone degradation, Paget's disease, or a bone tumor. In some embodiments, the fetal support tissue powder product is injected into a joint. In some embodiments, the fetal support tissue powder product is contacted with a bone (e.g., by use of a wound dressing or bandage). In some embodiments, the fetal support tissue powder product coats a bone stent, bone implant, or bone prosthesis (e.g., an osseointegrated implant). As used herein, an "osseointegrated implant" means a three dimensional implant containing pores into which osteoblasts and supporting connective tissue can migrate. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractible.

In some embodiments, a fetal support tissue powder product disclosed herein is used to treat arthritis (e.g., osteoarthritis, rheumatoid arthritis, septic arthritis, ankylosing spondylitis, spondylosis). In some embodiments, a fetal support tissue powder product disclosed herein is injected into an arthritic joint (e.g., a knee).

Miscellaneous Uses of a Fetal Support Tissue Powder Product

In some embodiments, a fetal support tissue powder product disclosed herein is used to augment soft tissue (e.g., as a dermal filler). In some embodiments, a fetal support tissue powder product disclosed herein is injected into subdermal facial tissues. In some embodiments, a fetal support tissue powder product disclosed herein is injected under wrinkles and aging lines of the face (e.g., nasolabial folds, melomental folds, "crow's feet" and forehead wrinkles). In some embodiments, a fetal support tissue powder product disclosed herein is used for lip augmentation. In some embodiments, a fetal support tissue powder product disclosed herein is injected into the lips. In some embodiments, a fetal support tissue powder product formulation disclosed herein for use as a dermal filler further comprises collagen, fibrin, or glycosaminoglycans. In some embodiments, a fetal support tissue powder product formulation disclosed herein for use as a dermal filler further comprises collagen, fibrin, or hyaluronic acid.

In some embodiments, a fetal support tissue powder product disclosed herein is used to prevent transplant rejection. In some embodiments, a transplant recipient is administered a fetal support tissue powder product systemically before, during, or after a transplant procedure. In some embodiments, a transplanted organ is contacted with a fetal support tissue powder product.

In some embodiments, a fetal support tissue powder product disclosed herein to treat hoarseness or voice disorders. In some embodiments, a fetal support tissue powder product disclosed herein is used for injection laryngoplasty to repair vocal cords.

EXAMPLES

Example 1

Processing Method

Placental tissue is harvested from placenta and rinsed with PBS. The placental tissue is then placed into a tube and lyophilized overnight. The lyophilized placental tissue is transferred into a grinding jar. A grinding ball is dropped in the grinding jar and the grinding jar is sealed. The grinding jar is immersed into liquid nitrogen for 5 min and then placed in a mill and ground at a 30 Hz grinding cycle for 4 min. The ground powder is transferred from the grinding jar and the surface of the grinding ball into a tube and reconstituted.

Example 2

Lyophilization, Protocol 1

Placental tissue is harvested from placenta and rinsed with PBS. The placental tissue is then placed in gas permeable pouches and lyophilized as follows:
Tissue samples are frozen at −40° C. for 3 hours;
Temperature is gradually increased from −40.0 to −5.0 and the pressure is set to 100 millitorr;
Primary drying occurs at −5.0 for 21 h;
Temperature is gradually increased from −5.0 to 25° C. to end lyophilization cycle.

Example 3

Lyophilization, Protocol 2

Placental tissue is harvested from placenta and rinsed with PBS. The placental tissue is then placed in gas permeable pouches and lyophilized as follows:
Tissue samples are frozen at −40.0 for 3 hours;
Temperature is gradually increased from −40.0 to −5° C. and the pressure is set to 100 millitorr;
Primary drying occurs at −5.0 for 21 h;
Temperature is gradually increased from −5.0 to 25.0 to end lyophilization cycle;
Secondary Drying occurs at 25.0 at a pressure of 100 millitorr for a maximum period of 16 h.

Example 4

Grinding

Placental tissue is harvested from placenta and rinsed with PBS. The placental tissue is then lyophilized. Next, the lyophilized placental tissue is ground as follows:
Lyophilized placental tissue and one grinding ball (e.g., a 25 mm grinding ball) are placed into a grinding jar (e.g., a 50 mL grinding jar);
The grinding jar is placed in a grinding machine;
The grinding parameters are set at 25 Hz and grinding occurs for 6 minutes.

Example 5

Preparation of Amniotic Membrane Powder

A placenta is removed from a pregnant woman undergoing a C-section. The amniotic membrane along with the chorionic membrane are isolated. The amniotic membrane is separated from the chorionic membrane. The amniotic membrane is cut into pieces and placed into a container with phosphate-buffered saline (PBS) containing 1.25 µg/ml Amphotericin B and 20 µg/ml Ciproflaxin. The amniotic membrane pieces are divided into several conical centrifuge tubes with each tube containing approximately 10 ml of amniotic membrane tissue. The amniotic membrane tissues in the tubes are frozen at −80.0 for at least 4 hours.

The caps of the tubes are replaced with Parafilm and several holes are made onto the Parafilm to allow for lyophilization to take place. Alternatively, commercially available filter tubes with filter and holes in the caps can be used. The tubes are placed in a lyophilizing flask, connected to a lyophilizing machine and lyophilized overnight at −50° C. and 0.280 mB, thereby producing a lyophilized placental amniotic membrane. The lyophilized placental amniotic membrane is transferred into a grinding jar. A grinding ball is placed into the grinding jar and the grinding jar is sealed. The grinding jar is immersed into liquid nitrogen for 5 min, and then placed in a grinding mill and ground at 30 Hz for 4 min, thereby producing a ground amniotic membrane powder. Alternatively, use of a grinding mill with an automated liquid nitrogen cooling feature would eliminate the need for manual immersion of the grinding jar into liquid nitrogen.

The ground amniotic membrane powder is transferred from the grinding jar and from the surface of the grinding ball into a tube and stored at −20° C. until dispensing and packaging. The amniotic membrane powder is reconstituted with water.

Example 6

Preparation of the Chorion Powder

A placenta is removed from a pregnant woman in the operating room during a C-section. The amniotic membrane along with the chorionic membrane are isolated. The chorion is subsequently isolated from the amniotic membrane.

The chorionic membrane is cut into pieces and placed into a container with phosphate-buffered saline (PBS) containing 1.25 µg/ml Amphotericin B and 20 µg/ml Ciproflaxin. The chorionic membrane pieces are divided into several conical centrifuge tubes with each tube containing approximately 10 ml of chorionic membrane tissue. The chorionic membrane tissues in the tubes are frozen at −80.0 for at least 4 hours.

The caps of the tubes are replaced with Parafilm and several holes are made onto the Parafilm to allow for lyophilization to take place. Alternatively, commercially available filter tubes with filter and holes in the caps can be used. The tubes are placed in a lyophilizing flask, connected to a lyophilizing machine and lyophilized overnight at −50° C. and 0.280 mB, thereby producing a lyophilized chorion tissue.

The lyophilized chorion tissue is transferred into a grinding jar. A grinding ball is placed into the grinding jar and the grinding jar is sealed. The grinding jar is immersed into liquid nitrogen for 5 min, and then placed in a grinding mill and ground at 30 Hz for 4 min, thereby producing a ground chorionic membrane powder. Alternatively, use of a grinding mill with an automated liquid nitrogen cooling feature would eliminate the need for manual immersion of the grinding jar into liquid nitrogen.

The ground chorionic membrane powder is transferred from the grinding jar and from the surface of the grinding ball into a tube and stored at −20° C. until dispensing and packaging. The chorionic membrane powder is reconstituted with water.

Example 7

Preparation of the Umbilical Cord Powder

A placenta is removed from a pregnant woman in the operating room during a C-section. The umbilical cord is isolated from the placenta. The umbilical cord is cut into pieces and placed into a container with phosphate-buffered saline (PBS) containing 1.25 µg/ml Amphotericin B and 20 µg/ml Ciproflaxin. The umbilical cord pieces are divided into several conical centrifuge tubes with each tube containing approximately 10 ml of umbilical cord tissue. The umbilical cord tissues in the tubes are frozen at −80° C. for at least 4 hours.

The caps of the tubes are replaced with Parafilm and several holes are made onto the Parafilm to allow for lyophilization to take place. Alternatively, commercially available filter tubes with filter and holes in the caps can be used. The tubes are placed in a lyophilizing flask, connected to a lyophilizing machine and lyophilized overnight at −50° C. and 0.280 mB, thereby producing a lyophilized umbilical cord tissue.

The lyophilized umbilical cord tissue is transferred into a grinding jar. A grinding ball is placed into the grinding jar and the grinding jar is sealed. The grinding jar is immersed into liquid nitrogen for 5 min, and then placed in a grinding mill and ground at 30 Hz for 4 min, thereby producing a ground umbilical cord powder. Alternatively, use of a grinding mill with an automated liquid nitrogen cooling feature would eliminate the need for manual immersion of the grinding jar into liquid nitrogen.

The ground umbilical cord powder is transferred from the grinding jar and from the surface of the grinding ball into a tube and stored at −20° C. until dispensing and packaging. The umbilical cord powder is reconstituted with water.

Example 8

Preparation of the Placental Powder

A placenta is removed from a pregnant woman in the operating room during a C-section. The placental is cut into pieces and placed into a container with phosphate-buffered saline (PBS) containing 1.25 µg/ml Amphotericin B and 20 µg/ml Ciproflaxin. The placenta pieces are divided into several conical centrifuge tubes with each tube containing approximately 10 ml of placental tissue. The placental tissues in the tubes are frozen at −80° C. for at least 4 hours.

The caps of the tubes are replaced with Parafilm and several holes are made onto the Parafilm to allow for lyophilization to take place. Alternatively, commercially available filter tubes with filter and holes in the caps can be used. The tubes are placed in a lyophilizing flask, connected to a lyophilizing machine and lyophilized overnight at −50° C. and 0.280 mB, thereby producing a lyophilized placenta.

The lyophilized placental is transferred into a grinding jar. A grinding ball is placed into the grinding jar and the grinding jar is sealed. The grinding jar is immersed into liquid nitrogen for 5 min, and then placed in a grinding mill and ground at 30 Hz for 4 min, thereby producing a placental powder. Alternatively, use of a grinding mill with an automated liquid nitrogen cooling feature would eliminate the need for manual immersion of the grinding jar into liquid nitrogen.

The placental powder is transferred from the grinding jar and from the surface of the grinding ball into a tube and stored at −20.0 until dispensing and packaging. The placental powder is reconstituted with water.

Example 9

Comparison of AM Tissue Processing Methods

| Protocol | Results |
| --- | --- |
| 1$^{st}$ Run: 5 ml of 2 × 2 cm AM were placed in the mortar. A 15 mm chrome steel grinding ball was dropped into the mortar and the lid was screwed on tight. The mortar was immersed horizontally in LN for 5 minutes and was run on the mill for a 4 min 30 Hz cycle. | Frozen AM pieces were wrapped around the ball and stuck to one side of the mortar. No grinding occurred. |
| 2$^{nd}$ Run: The 5 ml of AM from 1$^{st}$ Run was removed from the mortar and frozen at −80° C. for 15 minutes in a 15 ml tube. The tissue was then transferred into the mortar. A 15 mm chrome steel grinding ball was dropped into the mortar and the lid was screwed on tight. The mortar was immersed horizontally in LN for 5 minutes and was run on the mill for a 4 min 30 Hz cycle. | Frozen AM pieces were wrapped around the ball frozen and stuck to one side of the mortar. No grinding occurred. |
| 3$^{rd}$ Run: When the temperature of the mortar from the 2$^{nd}$ run had increased enough for the lid to be unscrewed, the contained tissue (still semi-frozen) was separated using a spatula from the grinding ball and the lid was screwed on tight. The mortar was immersed horizontally in LN for 5 minutes and was run on the mill for a 4 min 30 Hz cycle. | AM pieces were homogenized. Upon addition of PBS (1:1 v/v), the lysate could be drawn/injected via 18 gauge syringe but not the higher gauge syringes. |
| 4th Run: 5 ml of 2 × 2 cm AM were placed in a 30 mm dish and frozen at −20° C. for 2 hrs. The tissue was then transferred into the mortar. A 15 mm chrome steel grinding ball was dropped into the mortar and the lid was screwed on tight. No LN cooling performed. The mortar was run on the mill for a 4 min 30 Hz cycle. | AM pieces were homogenized but could not drawn/injected by an 18 gauge syringe. |
| 5$^{th}$ Run: 5 ml of 2 × 2 cm AM were placed in the mortar. A 15 mm chrome steel grinding ball was dropped into the mortar and the lid was screwed on tight. The mortar was immersed horizontally in LN for 1 minute and was run on the mill for a 4 minute 30 Hz cycle. | Frozen AM pieces were wrapped around the ball and stuck to one side of the mortar. No grinding occurred. |

| Protocol | Results |
|---|---|
| 6th Run: 5 ml of 2 × 2 cm AM from the 5th run were transferred into a 100 mm dish and soaked in DMEM:glycerol for 1 hour. The tissue is transferred into the mortar. A 15 mm chrome steel grinding ball is dropped into the mortar and the lid is screwed on tight. The mortar is immersed horizontally in LN for 5 minutes and was run on the mill for a 4 minute 30 Hz cycle. | Frozen AM pieces were wrapped around the ball and stuck to one side of the mortar. No grinding occurred. |
| 7th Run: 5 ml of 2 × 2 cm AM from the 5th run were lyophilized overnight in a 50 ml tube and transferred into the mortar. A 15 mm chrome steel grinding ball was dropped into the mortar and the lid was screwed on tight. The mortar was immersed horizontally in LN for 5 minutes and was run on the mill for a 4 minute 30 Hz cycle. | AM was well homogenized. Upon reconstitution of 4 ml distilled water, the homogenate could be easily aliquoted using a 1000 ul pipet and smoothly drawn/inject by 18, 20 and 21 and 23 gauge syringes. |

These experiments demonstrate importance of lyophilizing the fetal support tissue prior to grinding in the processing of fetal support tissues.

| | | | |
|---|---|---|---|
| 1. | Fresh AM is used | 1. | Frozen (−80° C.) AM is used |
| 2. | Dividing amniotic membrane into small pieces | 2. | Cutting amniotic membrane into adequately sized pieces to fit into lyophilization tubes and grinding jar |
| 3. | Homogenization by sonication | 3. | Grinding using grinding mill (grinding jar and ball) |
| 4. | Centrifugation & Filtration | 4. | No centrifugation & No Filtration |
| 5. | Order of Processing Steps: | 5. | Order of Processing Steps: |
| | i) Divide into pieces | | i) Dividing into pieces (if necessary) |
| | ii) Homogenization by sonication | | ii) Freezing |
| | iii) Centrifugation | | iii) Lyophilization |
| | iv) Aliquot | | iv) Grinding using grinding mill (grinding jar and ball) |
| | v) Freezing | | v) Aliquot |
| | vi) Lyophilizing | | |

Example 10

Figure 2:
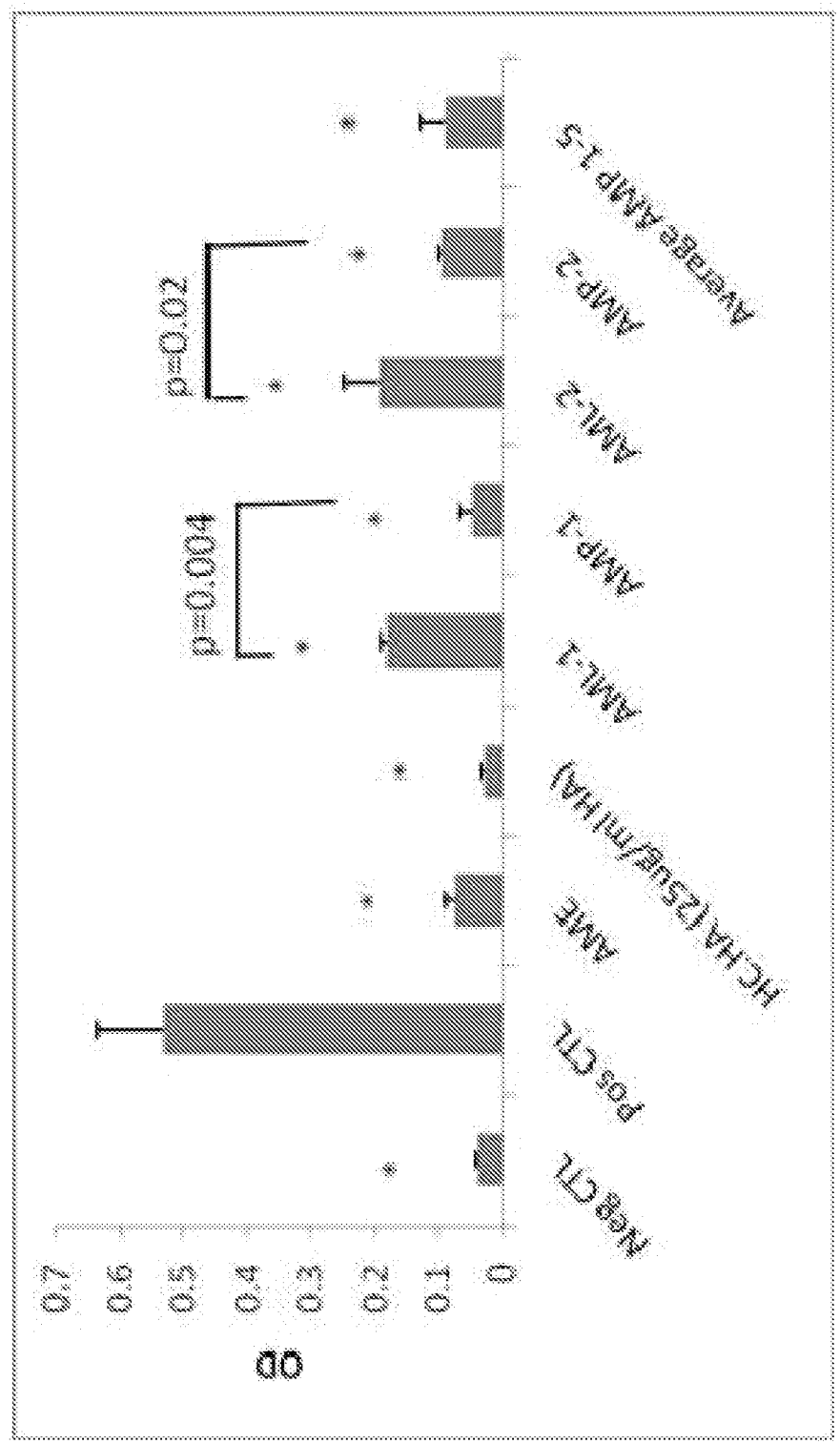
FIG. 2 exemplifies the performance of several tissue products (AME, HC-HA, AML, AMP) in inhibiting osteoclast formation. All AM derivates significantly inhibit osteoclast formation, and AMP prepared from different donors (AMP 1-5) consistently showed inhibitory activity that was more potent than AML.
Figure 3:
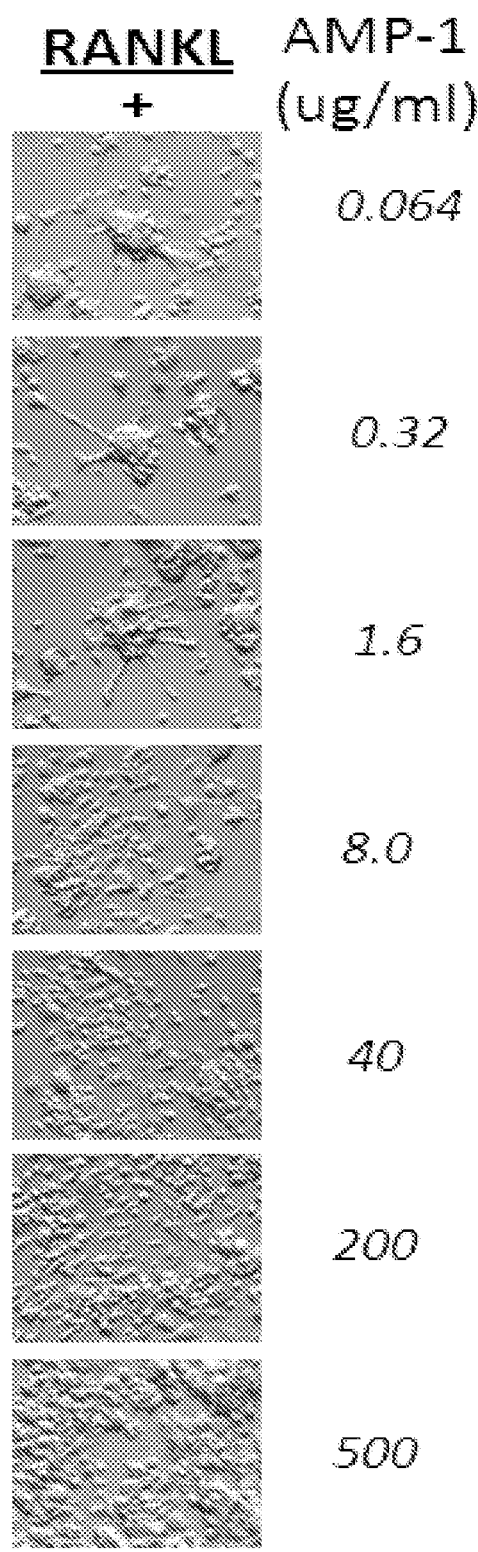
FIG. 3 exemplifies the effects of AMP (amniotic membrane powder) on osteoclastogenesis. AMP dose (0-500 µg/ml protein) dependently inhibits the osteoclast formation.
Figure 4:
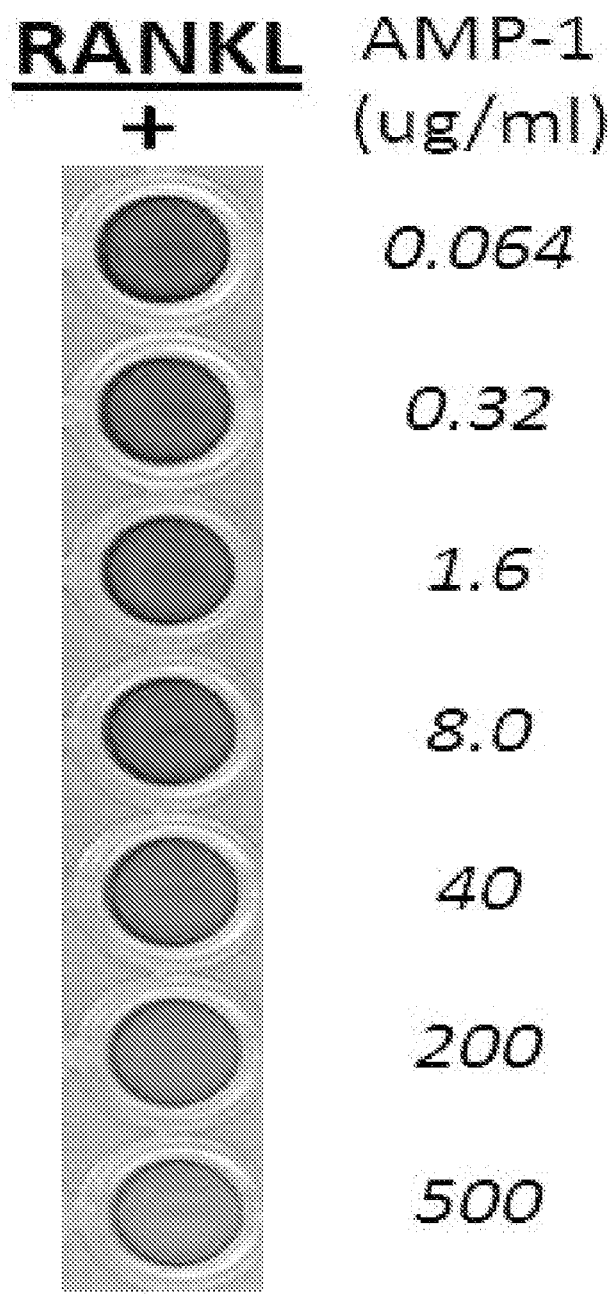
FIG. 4 exemplifies the effects of AMP (amniotic membrane powder) on osteoclastogenesis. The color picture of TRAP colorimetric assay is provided.
Figure 5:
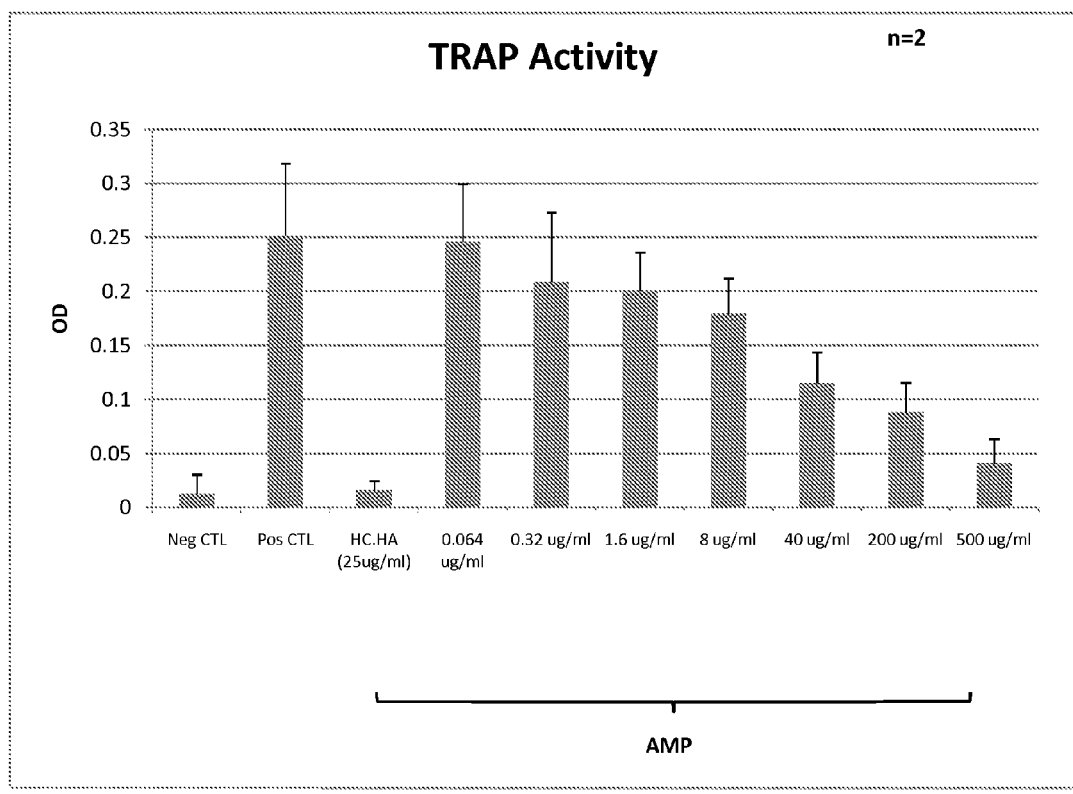
FIG. 5 exemplifies the effects of AMP (amniotic membrane powder) on osteoclastogenesis. Osteoclast inhibition by AMP is measured by TRAP Colorimetric assay.
Figure 6:
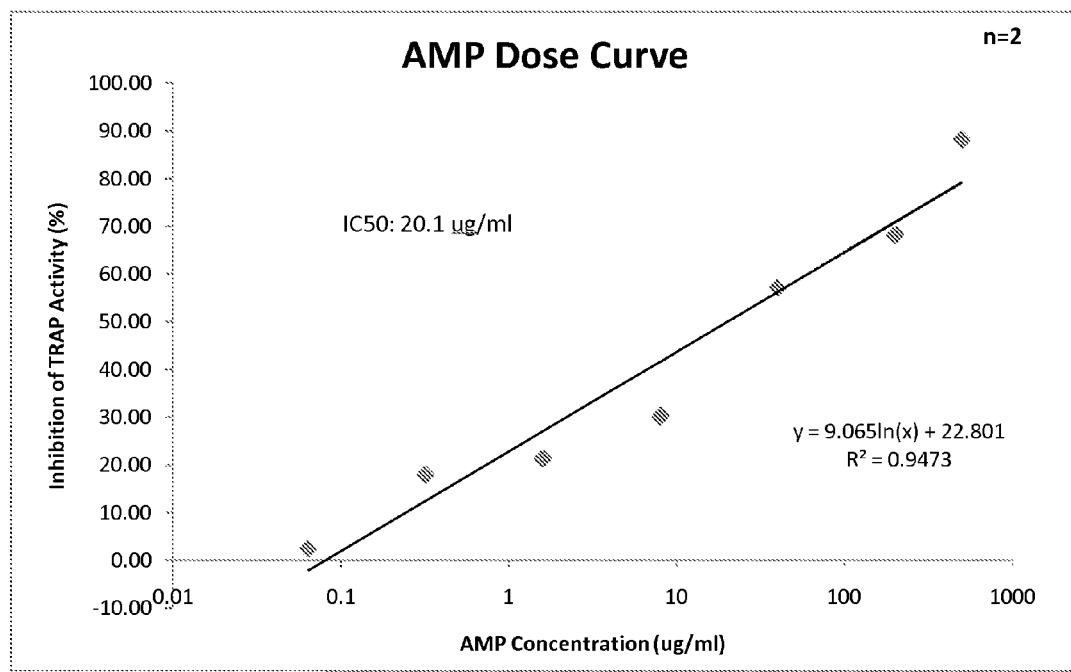
FIG. 6 exemplifies the effects of AMP (amniotic membrane powder) on osteoclastogenesis. $IC_{50}$ of AMP on the osteoclast formation is calculated to be about 20.1 µg/ml.
Figure 7:
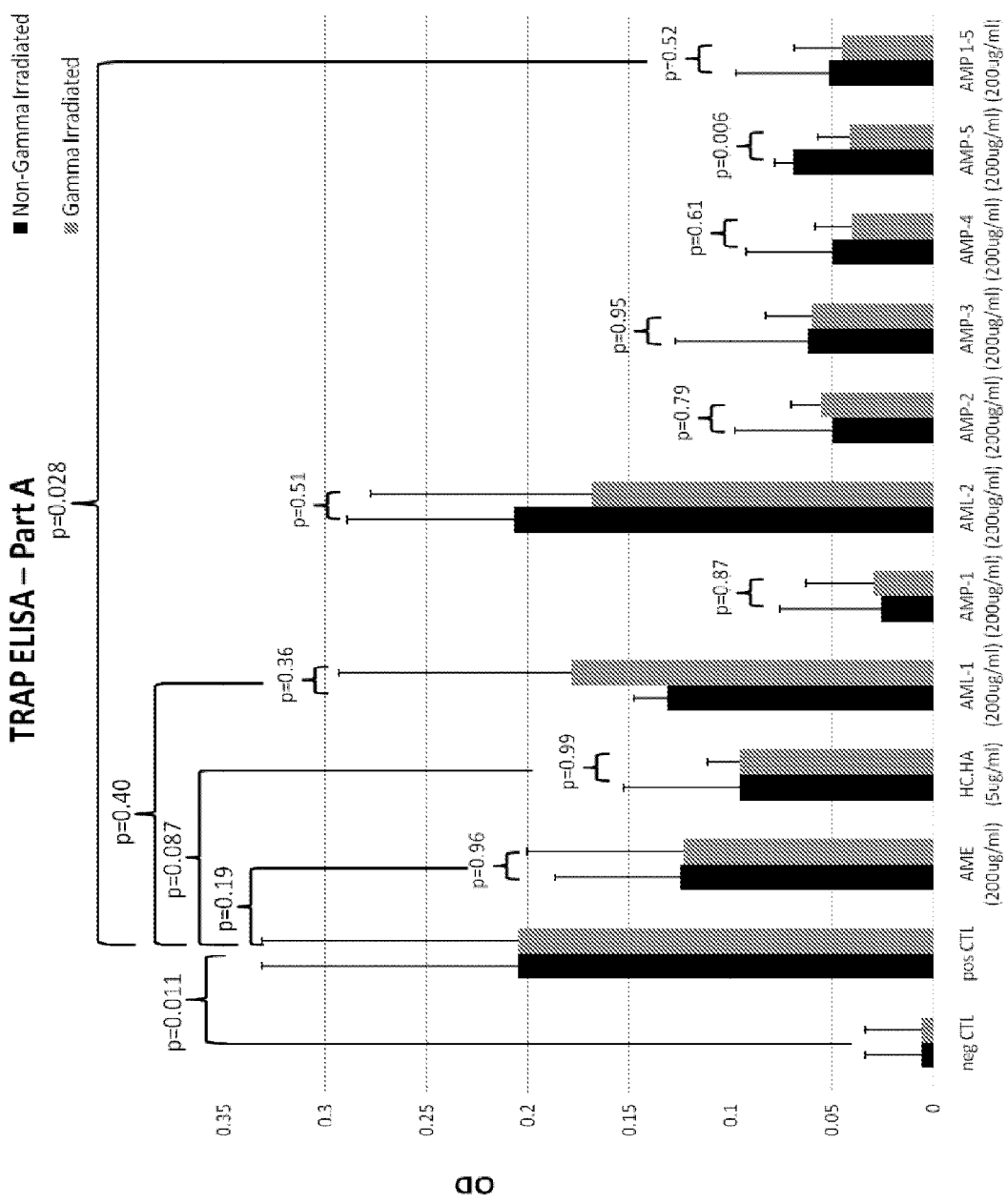
FIG. 7 exemplifies the effects of γ-irradiation on AMP. No significant difference in inhibition of TRAP activity was seen in gamma-irradiated AMP versus non gamma-irradiated AMP.

AMP Inhibits Osteoclast Formation from RANKL Stimulated RAW 264.7 Macrophage Cells Murine RAW 264.7 macrophage cells were seeded at a density of $4.0 \times 10^3$ cells/96 well (30-40% confluent), cultured in a-MEM media without Phenol Red and supplemented with 10% FBS, 100 μg/ml penicillin & streptomycin. 24 hours after seeding, cells were treated with or without 50 ng/ml RANKL stimulation. Experimental groups were simultaneously treated with AMP, AML or AME with protein concentration of 200 ug/ml. On Day 5, the culture was terminated and analyzed by TRAP staining and TRAP ELISA. The result from TRAP staining shows that osteoclasts (multi-nucleated cells) were not found on the negative control while large multi-nucleated cells were found on the positive control. AME inhibited osteoclast formation but did not inhibit RAW macrophage cell proliferation. Osteoclast formation and RAW macrophage cell proliferation were also inhibited by AML-1 and AML-2 (2 different donors), but such inhibition was not complete because small multi-nucleated cells could be seen after TRAP staining Osteoclast formation and RAW macrophage cell proliferation were also inhibited by AMP from 5 different donors at the same protein concentration of 200 ug/ml as AML. The result from TRAP staining shows that inhibitory action for osteoclast formation was seen on all AM derivatives. There was no significant difference between the TRAP ELISA reading between AMP and AME. For two donors, the TRAP ELISA reading for AMP is significantly lower than AML from the same donor (p=004 and p=0.02) at the same protein concentration 200 ug protein/ml. These data suggest that AMP performs better at inhibiting osteoclast formation compared to AML at the same protein concentration of 200 ug/ml (FIGS. 1-2 and Tables 1-3).

TABLE 1

| p-values | | |
|---|---|---|
| Comparison | | p = value |
| AMP 1-5 | AME | 0.24 |
| AMP 1-2 | AML 1-2 | 1.02E−05 |

TABLE 2

OD readings and p-values

| Conditions | OD ± standard deviation | p-value (compared to Pos CTL) |
|---|---|---|
| Neg CTL | 0.037 ± 0.0035 | 0.0013 |
| Pos CTL | 0.53 ± 0.11 | |
| AME | 0.073 ± 0.015 | 0.0028 |
| HC.HA (25 ug/ml HA) | 0.023 ± 0.0081 | 0.0023 |
| AML-1 | 0.18 ± 0.0097 | 0.0067 |
| AMP-1 | 0.046 ± 0.018 | 0.0022 |
| AML-2 | 0.19 ± 0.052 | 0.0034 |
| AMP-2 | 0.093 ± 0.0055 | 0.0036 |
| Mean AMP 1-5 | 0.087 ± 0.041 | 0.0017 |

TABLE 3

Protein Content of AMP from 5 different donors

| | BCA Reading (μg/ml) | Powder used/ml (mg/ml) | Protein (μg)/mg Powder | Total Powder Weight (mg) | Total Protein (mg) from 1 whole AM |
|---|---|---|---|---|---|
| AMP-1 | 13933 | 44.6 | 312 | 1340 | 419 |
| AMP-2 | 8777 | 30 | 293 | 880 | 257 |
| AMP-3 | 14527 | 42 | 346 | 1250 | 432 |
| AMP-4 | 16516 | 49 | 337 | 1836 | 619 |
| AMP-5 | 22727 | 51.2 | 444 | 1408 | 625 |

Example 11

Method of Treating a Wound

The amniotic membrane powder of Example 2 is applied to a patch. The patch is applied directly to the wound for a period of time sufficient to treat the wound.

Example 12

Method of Treating a Herniated Disc

The amniotic membrane powder of Example 2 is formulated as an injection. The formulation is injected at the site of the herniated disc. Treatment is continued until a therapeutic effect is observed.

Example 13

Method of Treating Osteoarthritis

The chorion powder of Example 3 is formulated as an injection. The formulation is injected into an arthritic joint. Treatment is continued until a therapeutic effect is observed.

Example 14

Clinical Trial for Osteoarthritis of the Knee

Subjects will receive 6 mL of an injectable formulation of AMP every week for six weeks at the target knee.
Study Type: Interventional
Study Design:
Allocation: Randomized
Endpoint Classification: Safety/Efficacy Study
Intervention Model: Parallel Assignment
Masking: Double Blind (Subject, Outcomes Assessor)
Primary Purpose: Treatment
Primary Outcome Measures:
Change from baseline in knee pain over the course of the six week treatment, as measured by participants using the Western Ontario and Macmaster Universities Osteoarthritis Index Liker Scale Version 3.1 (WOMAC LK 3.1). The WOMAC Pain Subscale has a score range of 0-4, where 0=no pain and 4=extreme pain.
Secondary Outcome Measures:
Change in baseline in knee pain at week 7 as measured by WOMAC LK 3.1
Participants level of Pain while walking at week 6 as measured by WOMAC LK 3.1.
Change from baseline over the course of the 6 week treatment in physical function measured by participants using WOMAC LK 3.1.
Change in baseline at week 6 in physical function as measured by participants using WOMAC LK Version 3.1.
Participant Global Assessment (PTGA) of the target knee osteoarthritis condition at week 6. PTGA is used by participants to rate their osteoarthritis from 0-4: very well=0; well=1; fair=2; poor=3; very poor=4.
Clinical Observer Global Assessment (COGA) of the target knee osteoarthritis condition at week 6. COGA is used by a blinded clinical observer to rate a participant's osteoarthritis from 0-4: very well=0; well=1; fair=2; poor=3; very poor=4.
Participants classified as responders per the Outcome Measures in Rheumatology-Osteoarthritis Research Society International (OMERACT-OARSI) criteria at week 6 [Time Frame: Week 26] [Designated as safety issue: No]. Participants are classified as a positive response if at least one of the following two conditions are met:

1. A significant improvement in either the pain (WOMAC A) or physical function (WOMAC C) subscales, defined as both a ≥50% improvement from baseline and an absolute change from baseline of ≥20 normalized units (NU), or 2. Improvement in at least 2 of 3 subscales-pain (WOMC A), physical function (WOMAC C) or Participant Global Assessment (PTGA). Improvement for all three scales is defined as ≥20% improvement from baseline and an absolute change from baseline of ≥10 NU.

Eligibility
40 years and older
Genders Eligible for Study: Both
Inclusion Criteria:
Patients with documented diagnosis of primary osteoarthritis (OA) of the target knee made at least 3 months prior to screening.
Has radiographic evidence of OA in the tibio-femoral compartment of the target knee with at least 1 definite osteophyte and a measureable joint space, as diagnosed by standard X-rays taken not longer than 3 months prior to screening, and before any baseline assessment.
Has continued target knee pain despite conservative treatment (e.g., weight reduction, physical therapy, and analgesics).
Has pain in the target knee as demonstrated by a score of 2 or 3 on the WOMAC LK 3.1 A1 (Walking Pain) Subscale.
Has a mean score of 1.5 to 3.5 on the WOMAC LK 3.1 A (Pain) Subscale.
Signed informed consent
Exclusion Criteria:
Has modified Kellgren-Lawrence Numerical Grading System of grade IV in the patella-femoral compartment of the target knee confirmed by standard X-rays taken not longer than 3 months prior to screening, and before any baseline assessment.
Has clinically apparent tense effusion of the target knee.
Has had viscosupplementation in any joint including the target knee within 9 months prior to screening
Has concomitant inflammatory disease or other condition that affects the joints (e.g., rheumatoid arthritis, metabolic bone disease, psoriasis, gout, symptomatic chondrocalcinosis and active infection, etc.)
Symptomatic OA of the contralateral knee or of either hip that is not responsive to paracetamol and requires other therapy.

Example 15

Clinical Trial for a Herniated Disc

Subjects will receive 6 mL of an injectable formulation of AMP every week for six weeks at the site of the herniated disc [better dosing schedule?].
Study Type: Interventional
Study Design:
Allocation: Randomized
Endpoint Classification: Safety/Efficacy Study
Intervention Model: Parallel Assignment
Masking: Double Blind (Subject, Investigator, Outcomes Assessor)
Primary Purpose: Treatment
Primary Outcome Measures:
Pain [time frame: 6 weeks] As primary endpoint, the functionality of the patients is measured by Oswestry Disability Score and VAS (leg and back pain) will be evaluated and the proportion of patients in each group for the need of surgery at week 6.

Secondary Outcome Measures:

Need for operative treatment and function status=proportion of patients operated after one year. As secondary endpoints, functionality of the patient (i.e., need for operative treatment, sick leave days and pain killer consumption)

Eligibility 18 to 75 years

Genders Eligible For Study: Both

Inclusion Criteria:

Acute of subacute (no more than 2 months) clinical sciatica symptoms caused by herniated disc confirmed by Magnetic Resonance Imaging (MRI).

Oswestry Disability Score at least 16% at entry.

VAS (leg and back pain) at least 40 mm at entry.

Exclusion Criteria:

History of chronic back pain.

Previously operated herniated disc or other spinal column operation.

Example 16

Clinical Trial for Wound Healing

Subjects will receive treatment with a topical formulation containing AMP. The topical treatment is applied once daily during a 12-day treatment.

Study Type: Interventional
Study Design:
Allocation: Randomized
Endpoint Classification: Efficacy Study
Intervention Model: Single Group Assignment
Masking: Single Blind
Primary Purpose: Treatment
Primary Outcome Measures:

Clinical assessment of the wound healing efficacy of AMP compared to untreated using a score for wound healing rates [Time Frame: 12 days]

Secondary Outcome Measures:

Clinical assessment of the wound healing efficacy based on photo documentation [Time Frame: 12 days]

Eligibility 18 years and older

Genders Eligible For Study: Both

Inclusion Criteria:

Healthy skin in the test area

Physical examination must be without disease findings unless the investigator considers an abnormality to be irrelevant for the outcome of the clinical trial Signed informed consent Exclusion Criteria:

Acne, suntan, eczema, hyperpigmentation or tattoos in the test fields

Dark-skinned persons whose skin color prevents ready assessment of skin reactions Subjects with diabetes, psoriasis or lichen ruber planus;

History of wound-healing complications, or keloid and hypertrophic scarring;

Treatment with systemic or locally acting medications which might counter or influence the trial aim within two weeks before the baseline visit (e.g. antihistamines or glucocorticosteroids)

Example 17

Clinical Trial for Bone Regeneration at Tooth Extraction Site

Subjects will receive treatment with an AMP containing dressing at teeth extraction sockets in the maintenance of alveolar ridge.

Study Type: Interventional
Study Design:
Allocation: Randomized
Endpoint Classification: Safety/Efficacy Study
Intervention Model: Single Group Assignment
Masking: Open Label
Primary Purpose: Treatment
Primary Outcome Measures:

Height and density of the alveolar ride at 1 week and 3 weeks after tooth extraction as measured by MSCT scans.

Eligibility 18 years and older

Genders Eligible For Study: Both

Inclusion Criteria:

Systemically healthy female or male subjects

Non-smoking

Does not take any medications

Signed informed consent

Exclusion Criteria:

Under 18 years of age

Current Alcohol or drug abuse

Systemic-local conditions that would interfere with wound healing or osseointegration A history of chemotherapy and radiotherapy in the head and neck region Example 18

Clinical Trial for Treatment of Hypertrophic and Keloid Scars

Subjects will receive a topical formulation of AMP, which will be applied on a scar, rubbing in different directions for 2 minutes, three times a day, for 12 weeks.

Study Type: Interventional
Study Design:
Allocation: Randomized
Endpoint Classification: Efficacy Study
Intervention Model: Parallel Assignment
Masking: Double Blind (Subject, Caregiver, Investigator)
Primary Purpose: Treatment
Primary Outcome Measures:

Length of hypertrophic scar(s) and keloids measured by a millimetric ruler at week 12 (end of treatment)

Secondary Outcome Measures:

Occurrence of adverse effects at week 12

Photographs of lesions at week 12

Eligibility:

18 years to 55 years

Genders Eligible For Study: Both

Inclusion Criteria:

Hypertrophic wound or keloid with no treatment for more than 1 month

Exclusion Criteria:

Usage of steroids within 30 days

Malignant neoplastic conditions

Alcoholism

Handicap and/or psychiatric condition preventing treatment accomplishment

Example 19

Clinical Trial for Spinal Adhesions

AMP, which is incorporated into an adhesion barrier is tested for its effectiveness at reducing pedirual fibrosis formation and radicular pain in comparison to a control group receiving standard care.
  Study Type: Interventional
  Study Design:
  Allocation: Randomized
  Endpoint Classification: Safety/Efficacy Study
  Intervention Model: Parallel Assignment
  Masking: Double Blind (Subject, Outcomes Assessor)
  Primary Purpose: Treatment
  Primary Outcome Measures:
  Radiological, pain, and functional outcome assessments
  Secondary Outcome Measures:
  Radiological, pain, and functional outcome assessments
  Eligibility:
  Ages Eligible for Study: 18 years to 70 years
  Genders Eligible for Study: Both
  Inclusion Criteria:
  Patients with radicular pain requiring single-level lumbar hemi-laminectomy or hemilaminotomy procedures with disectomy in the lower lumbar sping
  Require initial open lumbar surgery for extruded, prolapses or bulging intervertebral discs
  Requires removal of herniated disc fragment
  Exclusion Criteria:
  Current or historic open traumatic surgery to spine
  Any previous surgery to the lumbar spine or percutaneous tissue destruction or ablation procedures
  Women who are nursing, pregnant, or planning to become pregnant
  Known positive for HIV
  Insulin-dependent Diabetes Mellitus
  Clinically significant structural disorders
  Morbid obesity
  History of alcohol or drug abuse within 2 years of trial

Example 20

Clinical Trial for Rheumatoid Arthritis

Ten healthy subjects and 10 subjects with rheumatoid arthritis will receive an infection of AMP every two weeks for 24 weeks.
  Study Type:
  Interventional
  Study Design:
  Allocation: Randomized
  Endpoint Classification: Safety/Efficacy Study
  Intervention Model: Parallel Assignment
  Masking: Double Blind (Subject, Investigator, Outcomes Assessor)
  Primary Purpose: Treatment
  Primary Outcome Measures:
  Evaluate the effect of bi-weekly AMP injection to standard-of-care DMARD therapy in subjects with moderately active rheumatoid arthritis based on disease activity measures
  Secondary Outcome Measures:
  Quality of life in patients treated with bi-weekly AMP injection compared to standard-of-care DMARD therapy.
  Eligibility:
  Ages Eligible for Study: 18 years to 80 years
  Genders Eligible for Study: Both
  Inclusion Criteria:
  Subject is diagnosed with rheumatoid arthritis as determined by meeting 1987 American College of Rheumatology (ACR) classification criteria and has had rheumatoid arthritis for at least 6 months
  Subject has moderate rheumatoid arthritis during screening, as defined by a DAS28-CRP>3.2 and <5.1
  Subject has active rheumatoid arthritis defined as $\geq 3$ swollen joints (out of 28 joints examined) and $\geq 3$ tender/painful joints (out of 28 joints examined) at screening and baseline. (A full 66/68 count joint count will be performed at baseline, but only joints in the 28-count joint count will be considered for eligibility. The 28-joint count consists of the finger joints excluding the distal interphalangeal joints, the wrists, elbows, shoulders, and knees)
  Subject must be currently taking a DMARD such as methotrexate, sulfasalazine, leflunomide, minocycline, and/or hydroxychloroquine
  Exclusion Criteria:
  Subject had prosthetic joint infection within 5 years of screening or native joint infection within 1 year of screening
  Subject has Class IV rheumatoid arthritis according to ACR revised response criteria
  Subject has any active infection (including chronic or localized infections) for which anti-infectives were indicated within 28 days prior to first investigational product dose
  Subject has previously used more than one experimental biologic DMARD. Subject with prior use of no more than one experimental biologic is permitted if the subject received no more than 8 weeks of treatment. The use of the experimental biologic must not have occurred within 2 months of the first dose of investigational product
  Subject has previously used more than one commercially available biologic DMARD. Subject with prior use of no more than one commercially available biologic is permitted if the subject received no more than 8 weeks of treatment and did not discontinue because of lack of effect. The use of the biologic must not have occurred within 2 months of the first dose of investigational product.

Example 21

Clinical Trial for Atopic Dermatitis

A topical formulation comprising AMP is applied to adults patients with moderate atopic dermatitis using the Eczema Area Severity Index (EASI) assessment of disease severity.
  Study Type:
  Interventional
  Study Design:
  Allocation: Randomized
  Endpoint Classification: Safety/Efficacy Study
  Intervention Model: Parallel Assignment
  Masking: Double-Blind
  Primary Purpose: Treatment
  Primary Outcome Measures:
  Clinical efficacy of 3% GW842470X cream applied to involved skin of adult patients with moderate atopic dermatitis using the Eczema Area Severity Index (EASI).

Secondary Outcome Measures:
Safety and tolerability of topical AMP formulation
Clinical efficacy using SCORing Atopic Dermatitis score & Investigators Global Assessment Scale
Symptoms: pruritus & sleep loss
Eligibility:
Ages Eligible for Study: 18 years to 80 years
Genders Eligible for Study: Both
Inclusion Criteria:
Moderate atopic dermatitis patients (IGA=3).
The disease involvement must be >5% of body surface area.
Exclusion Criteria:
Patients with any active skin disease other than atopic dermatitis
Patients who have had systemic treatment for atopic dermatitis or other topical or transdermal treatments (such as nicotine, hormone replacement therapies) within 14 days prior to first application of study medication and/or topical treatment with tar, any corticosteroid, topical immunomodulators or oral treatment with any corticosteroids within 10 days prior to first application and/or oral anti-histamines within 5 days of the first dose.

Example 22

Clinical Trial for Crohn's Disorder

Study Type:
Interventional
Study Design:
Allocation: Randomized
Endpoint Classification: Efficacy Study
Intervention Model: Parallel Assignment
Masking: Open Label
Primary Purpose: Treatment
Primary Outcome Measures:
Crohn's Disease Histologic Index of Severity (CDHIS) [Time Frame: Baseline and 12 weeks] The CDHIS contains eight items which reflect epithelial injury, mucosal inflammation, and the extent of involvement. Scores range from 0-16, with patients with moderate to severely active CD typically having scores of 6-12. It was computed by a GI pathologist. The higher the score indicates worsening of disease, the lowest score is 0 and highest possible is 16
Secondary Outcome Measures:
IMPACT III Score [Time Frame: Baseline, 12 weeks, 24 weeks]. Health-related quality of life (QOL) was assessed using the IMPACT 111 questionnnaire. It is a self-administered 35 item questionnaire which typically takes 10-15 minutes to complete. Scores range from 0-350, with higher scores reflecting better perceived quality of life.
Total Corticosteroid Use [Time Frame: 12 weeks, 24 weeks]
Crohn's Disease Endoscopic Index of Severity (CDEIS) [Time Frame: Baseline and 12 weeks] Measure of mucosal disease at baseline and week 12 obtained during colonoscopy. The CDEIS score generally ranges from 0-30. A higher score indicates more severe mucosal inflammation.
Fecal Calprotectin [Time Frame: At 24 and 64 weeks]. Fecal calprotectin is a previously validated stool marker of intestinal inflammation in Crohn's Disease.

Eligibility:
Ages Eligible for Study: 18 years to 80 years
Genders Eligible for Study: Both
Inclusion Criteria:
Diagnosis of Crohn's disease (CD) with ileo-colonic involvement as determined by standard clinical, radiological, and pathological criteria.
Moderate to severely active CD as defined by a PCDAI (Pediatric Crohn's Disease Activity Index)≥30.
Currently taking Prednisone or Budesonide at starting dose (not tapering) May continue stable doses of AZA/6-MP, methotrexate, and/or mesalamine at entry.
Exclusion Criteria:
Acute critical illness
Active neoplasia
Diabetes mellitus
History of intracranial lesion and/or neoplasia
Severe disease requiring hospitalization for treatment
Current therapy with infliximab as this may independently rapidly reduce clinical disease activity and promote mucosal healing
Use of prednisone or budesonide and in tapering phase
Family history of colorectal cancer before age 50
Personal or familial history of familial polyposis syndrome Example 23

Clinical Trial for Diabetes Mellitus Type I

Study Type:
Interventional
Study Design:
Endpoint Classification: Safety Study
Intervention Model: Single Group Assignment
Masking: Open Label
Primary Purpose: Treatment
Primary Outcome Measures:
Incidence and severity of adverse events and laboratory anomalies [Time Frame: through day 364]
Secondary Outcome Measures:
AUC for c-peptide responses following MMTT
Frequency of severe hypoglycemia
Insulin dose in units per kilogram
HbAlc levels
Eligibility:
Ages Eligible for Study: 18 years to 45 years
Genders Eligible for Study: Both
Inclusion Criteria:
Diagnosed with type 1 diabetes (per ADA criteria) more than 3 but less than 48 months prior to enrollment
Positive for at least one islet cell autoantibody (GAD65-antibody, CA512-antibody and/or ICA)Exclusion Criteria:
chronic use of glucocorticoids or other immunosuppressive ages 4 weeks before enrollment
History of recurrent infections, other autoimmune diseases, cardiac disease, cataracts or other chronic medical conditions that investigators believe could compromise participant safety Example 24

Method of Treating Dry Eve

The amniotic membrane powder of Example 2 is formulated as ophthalmic eye drop formulation. The formulation is administered to an affected eye. Treatment is continued until a therapeutic effect is observed.

Example 25

Method of Treating Psoriasis

The amniotic membrane powder of Example 2 is formulated as a topical cream formulation. The formulation is administered to a psoriasis-affected area of the skin. Treatment is continued until a therapeutic effect is observed.

Example 26

Method of Treating Endotoxic Shock

The amniotic membrane powder of Example 2 is formulated as an intravenous injection. The formulation is administered to a patient affected by endotoxic shock. Treatment is continued until a therapeutic effect is observed.

Example 27

Method of Treating Graft Versus Host Disease

The amniotic membrane powder of Example 2 is formulated as an intravenous injection. The formulation is administered to a patient concurrent with or following a transplantation of tissue or cells. Treatment is continued either for the life of the transplantation within the host, or until the patient is definitively diagnosed as lacking graft versus host disease.

Example 28

Method of Treating Cancer by Inhibiting Angiogenesis

The amniotic membrane powder of Example 2 is formulated as an intravenous injection. The formulation is administered to a patient at a tumor site. Treatment is continued until a decrease in tumor size is observed.

Example 29

Method of Treating Ankylosing Spondylitis

The amniotic membrane powder of Example 2 is formulated as an intravenous injection. The formulation is administered to a patient at sites of inflammation and pain. Treatment is continued until a therapeutic effect is observed.

Example 30

Method of Treating Rheumatoid Spondylitis

The amniotic membrane powder of Example 2 is formulated as an intravenous injection. The formulation is administered to a patient at sites of inflammation and pain. Treatment is continued until a therapeutic effect is observed.

Example 31

Method of Treating Periodontitis

The amniotic membrane powder of Example 2 is formulated as a topical formulation (i.e., a tooth paste). The formulation is administered to the patient's gums. Treatment is continued until a therapeutic effect is observed.

Example 32

TRAP Assay

Murine RAW 264.7 macrophage cells were seeded at a density of $4.0 \times 10^3$ cells/96 well (30-40% confluent), cultured in α-MEM media without Phenol Red and supplemented with 10% FBS, 100 µg/ml penicillin & streptomycin. 24 hours after seeding, cells were treated with or without 50 ng/ml RANKL stimulation. Experimental groups were simultaneously treated with AMP, AML or AME with protein concentration of 200 µg/ml. On Day 5, the culture was terminated and analyzed by TRAP staining and TRAP Colorimetric Assay.

Osteoclast formation and RAW macrophage cell proliferation were also inhibited by AMP from 5 different donors (FIG. 2) at the same protein concentration of 200 µg/ml as AML.

The result from TRAP staining shows that the inhibitory action for osteoclast formation was seen with all AM derivatives.

Example 33

Powder Derived from Amniotic Membrane (AMP), Chorion (CHP), Amnio-Chorion (ACP), Placenta (PCP), Whole Umbilical Cord (UCP), or Umbilical Cord AM (UCAP) Inhibits Osteoclast Formation from RANKL Stimulated RAW 264.7 Macrophage Cells Murine RAW 264.7 macrophage cells were seeded at a density of $4.0 \times 10^3$ cells/96 well (30-40% confluent), cultured in α-MEM media without Phenol Red and supplemented with 10% FBS, 100 µg/ml penicillin & streptomycin. 24 hours after seeding, cells were treated with or without 50 ng/ml RANKL stimulation. Experimental groups were simultaneously treated with AMP, CHP, ACP, PLP, UCP, and UCAP with protein concentration of 100 µg/ml. On Day 5, the culture was terminated and analyzed by TRAP Colorimetric Assay.

Figure 8:
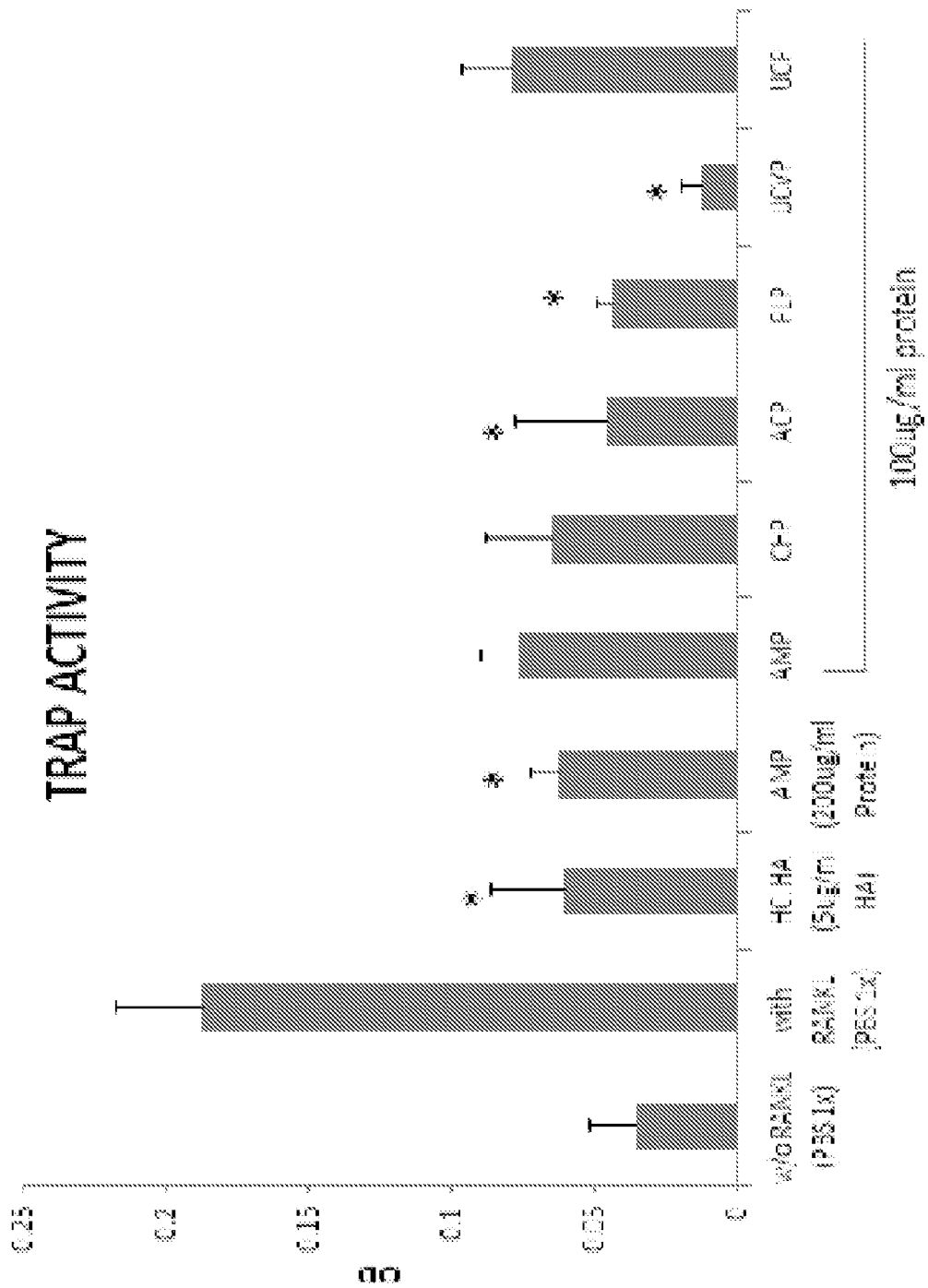
FIG. 8 exemplifies the performance of AMP in inhibiting osteoclast formation. Powders were made from amniotic membrane (AMP), chorion (CHP), amnio-chorion (ACP), whole placenta (PLP), whole umbilical cord (UCP), and umbilical cord amniotic membrane (UAMP). Like HC-HA (5 µg/ml), AMP (200 µg/ml), ACP (100 µg/ml), PLP (100 µg/ml), and WUC (100 µg/ml) significantly inhibit osteoclast formation.

Osteoclast formation was inhibited by all powder derived from amniotic membrane (AMP), chorion (CHP), amnio-chorion (ACP), placenta (PCP), whole umbilical cord (UCP), and umbilical cord AM (UCAP) (FIG. 8).

Example 34

AMP Promotes the Mineralization of Osteoblasts

Osteoblast precursor MC3T3-E1 cells were maintained in DMEM/10% FBS but were re-suspended into a-MEM/10% FBS and seeded at $1 \times 10^5$/ml on 24 well plastic (2 ml per well, and designated as Day 1 from here onwards) for 2 days.

The culture medium was replaced with either PBS (Neg. Ctrl), osteoblast-inducing reagents (0.2 mM ascorbic acid 2-phosphate and 10 mM glycerol 2-phosphate, Pos. Ctrl), or osteoblast-inducing reagents plus 0.1 µg/ml HC-HA or 125 µg/ml AMP. The cell culture medium was changed every 3 days until on Day 18. From Day 8 onwards, the osteoblast-inducing reagents was additionally supplemented with melatonin (50 ng/ml).

Figure 9:
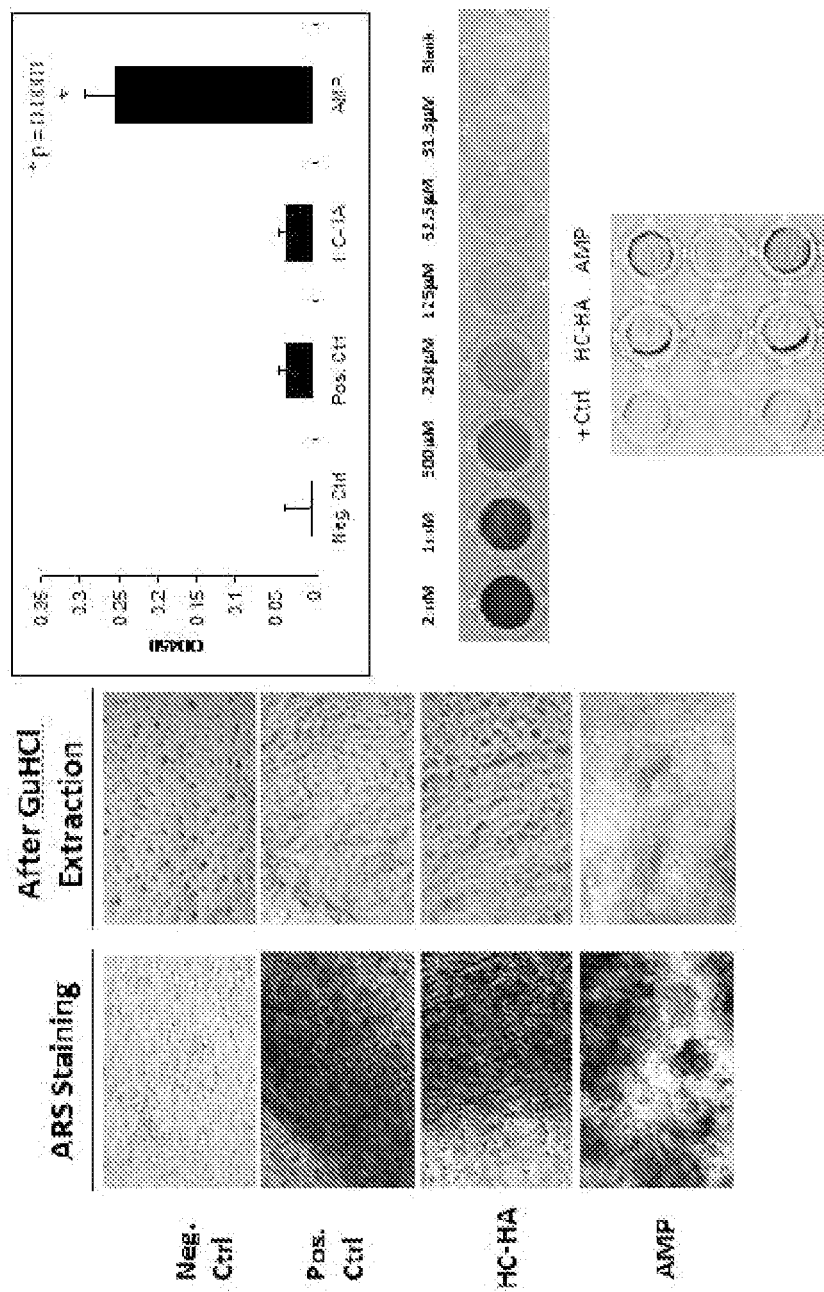
FIG. 9 exemplifies the effects of AMP on bone matrix mineralization. When ARS is measured quantitatively, cell treated with AMP (125 µg/ml) significantly promotes mineralization (p=0.0001).
Figure 10:
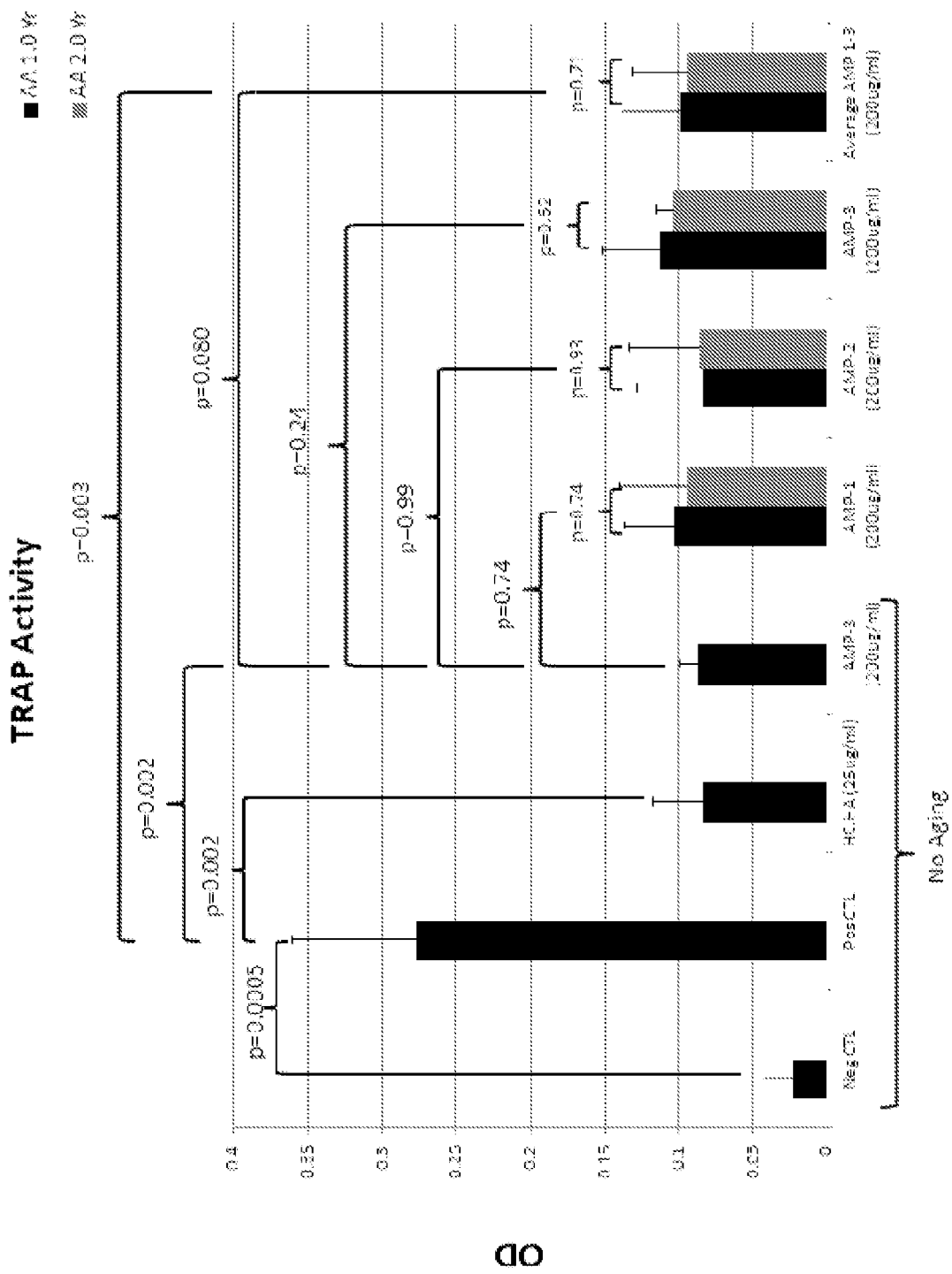
FIG. 10 exemplifies the effects of AMP on macrophages. Macrophages were treated with AMP-1 to AMP-3 after one and two years in storage, no significant change was observed in inhibition of TRAP activity with increased storage time. TRAP activity was measured in macrophages by ELISA staining.
Figure 11:
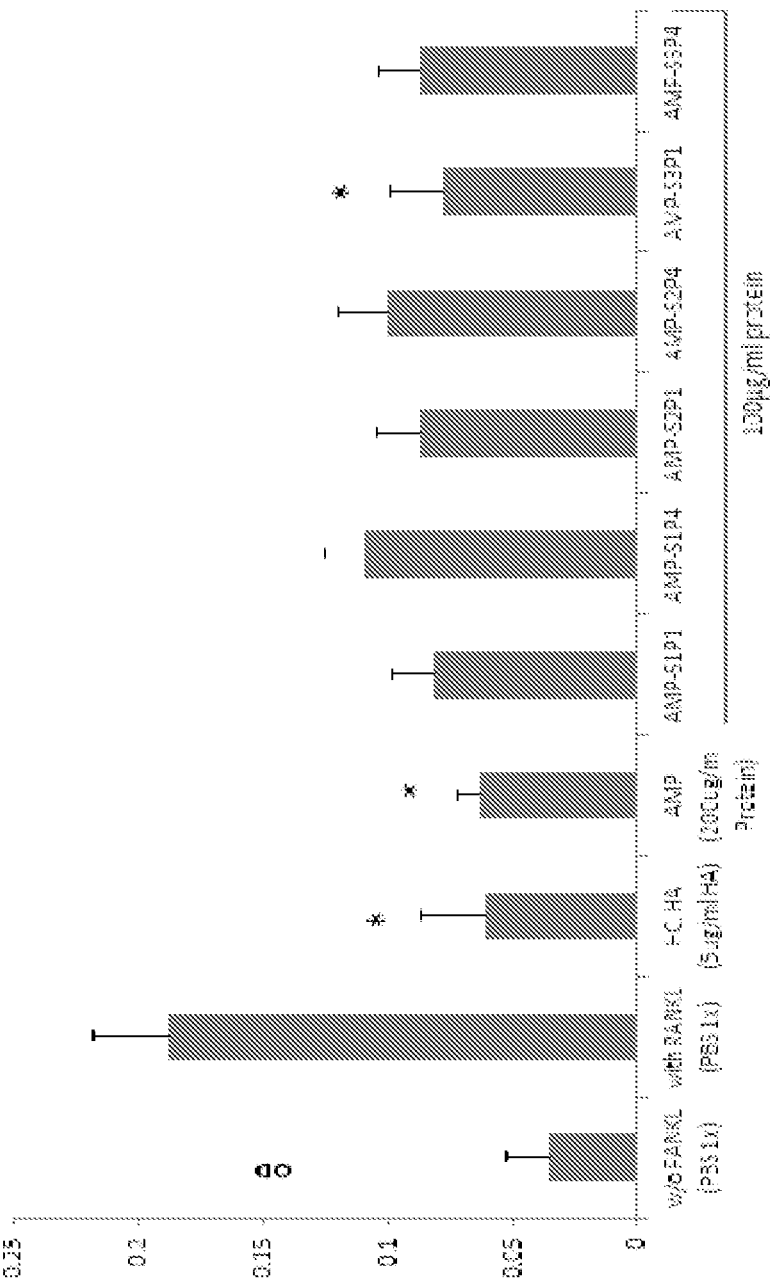
FIG. 11 exemplifies the effects of lyophilization on AMP. AM potency is not affected by placing AM at different locations in a lyophilizer. A total of 12 plates (each plate containing AM tissue from 1 donor) were lyophilized. Six samples were selected (1 inner plate and 1 outer plate for each of the 3 shelves: S1P1, S1P4, S2P1, S2P4, S3P1, S3P4) and were assayed for osteoclast potency.
Figure 12:
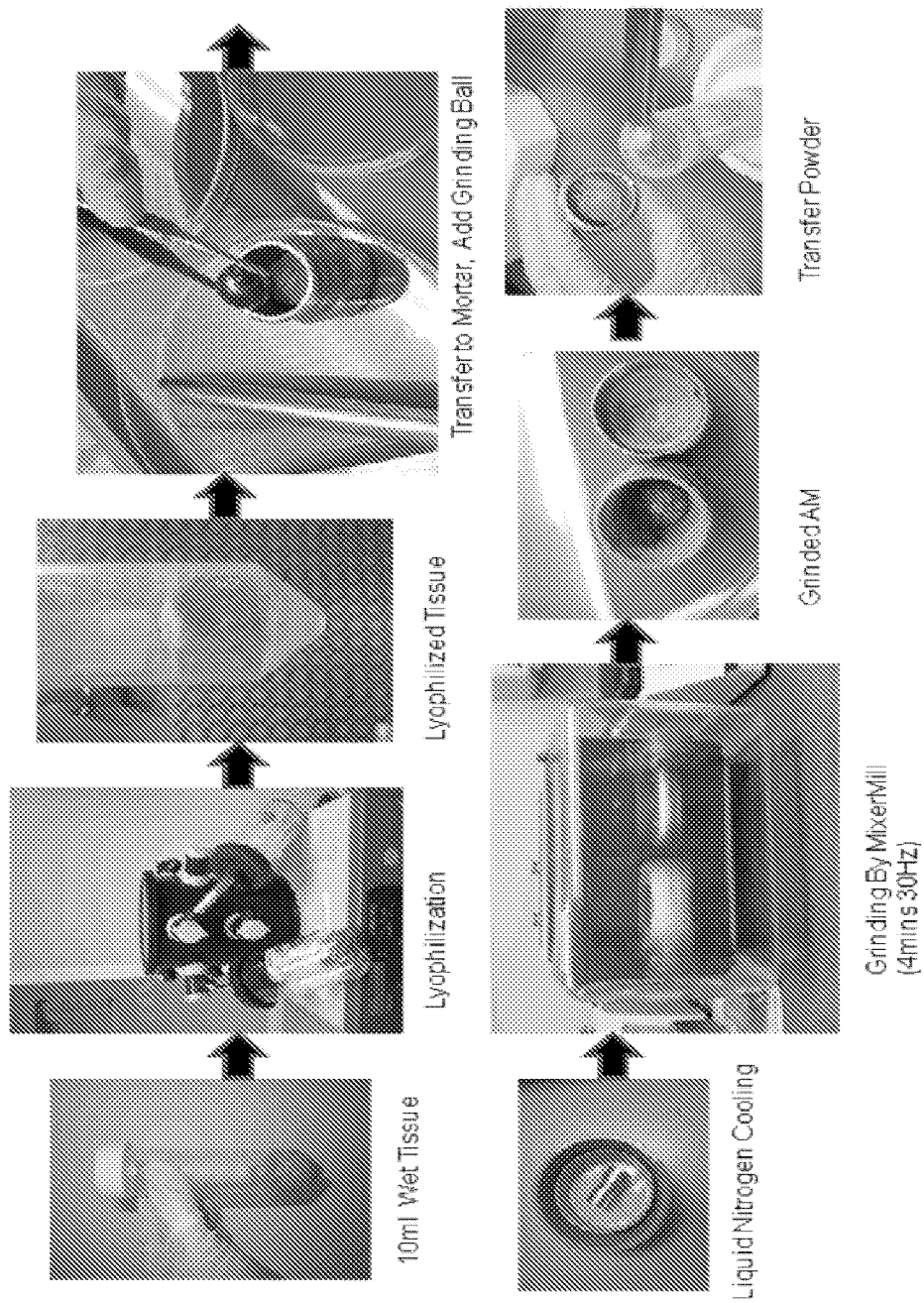
FIG. 12 exemplifies a method of producing AMP. Wet AM is placed into a tube with a porous cap and is frozen. The tube containing the frozen AM is then placed into a flask and lyophilized overnight using a benchtop lyophilizer. The lyophilized AM tissue is then transferred into the jar. A grinding ball is dropped into the jar and the jar is sealed with a screw fit lid. The entire jar is immersed into liquid nitrogen and placed in the grinding mill. The grinded powder is transferred from the jar. Using a spatula, the powder is then transferred from the jar and surface of the grinding ball to be stored.
Figure 13:
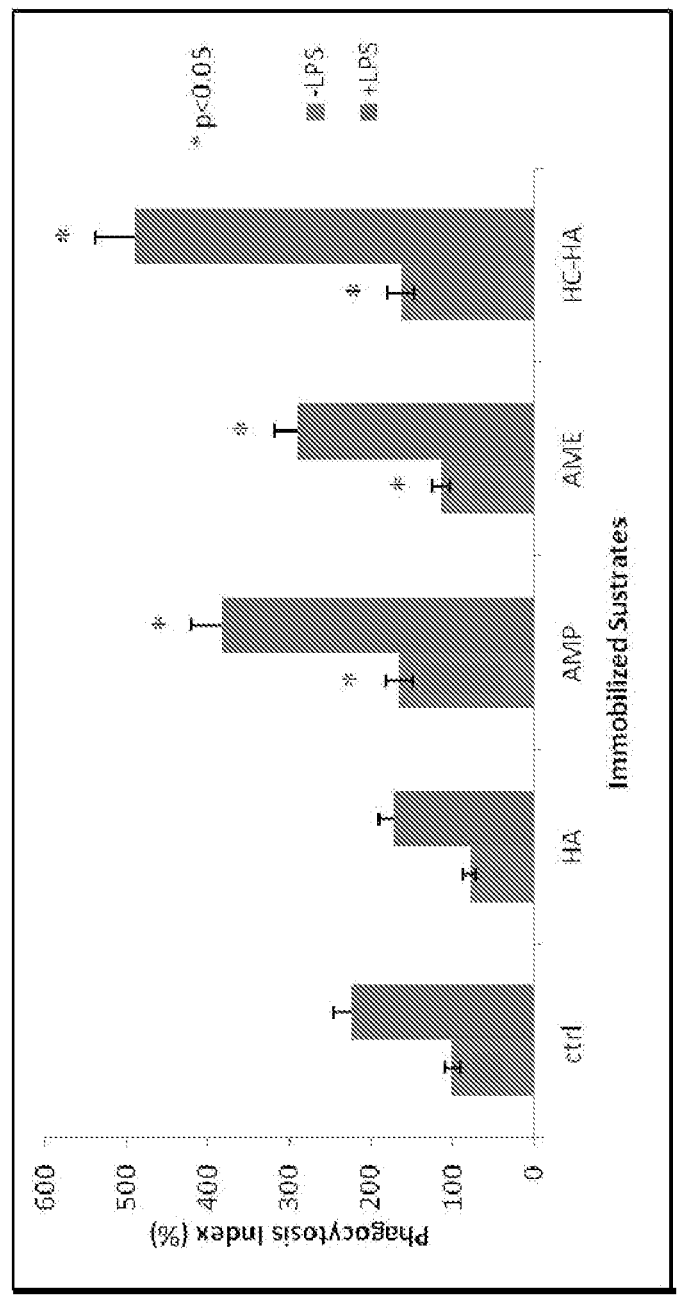
FIG. 13 exemplifies the effect of AMP on phagocytosis of apoptotic neutrophils by resting or LPS-stimulated macrophages. RAW264.7 cells ($1\times10^5$/ml) were cultivated on the immobilized PBS control, HA (2 µg/well), AMP (10 µg protein/well), AME (2 µg HA/well), or HC-HA (2 µg HA/well) without or with LPS (1 µg/ml) stimulation for 6 days (n=3). The cell culture medium was then removed, and 100 µl of $2\times10^6$/ml of apoptotic neutrophils in IMDM (Iscove's Modified Dulbecco's Medium) [prepared by treatment of resting neutrophils isolated from the normal human peripheral blood with roscovitine (20 µM) for 8 h] were added to each well containing resting or LPS-stimulated macrophages. After incubation for 30 min at 37° C., each well was washed three times with the cold PBS, and cell lysates (including macrophages and phagocytosed neutrophils) were collected to determine human myeloperoxidase (MPO) by ELISA to measure phagocytosed neutrophils by macrophages. The relative phagocytosis index was derived from the amount of MPO in each cell lysate normalized with its total proteins. The phagocytosis index of the control without LPS (−LPS) is defined as 100%. An asterisk (*) indicates p value <0.05 when compared with PBS control in the same group (−LPS or +LPS).
Figure 14:
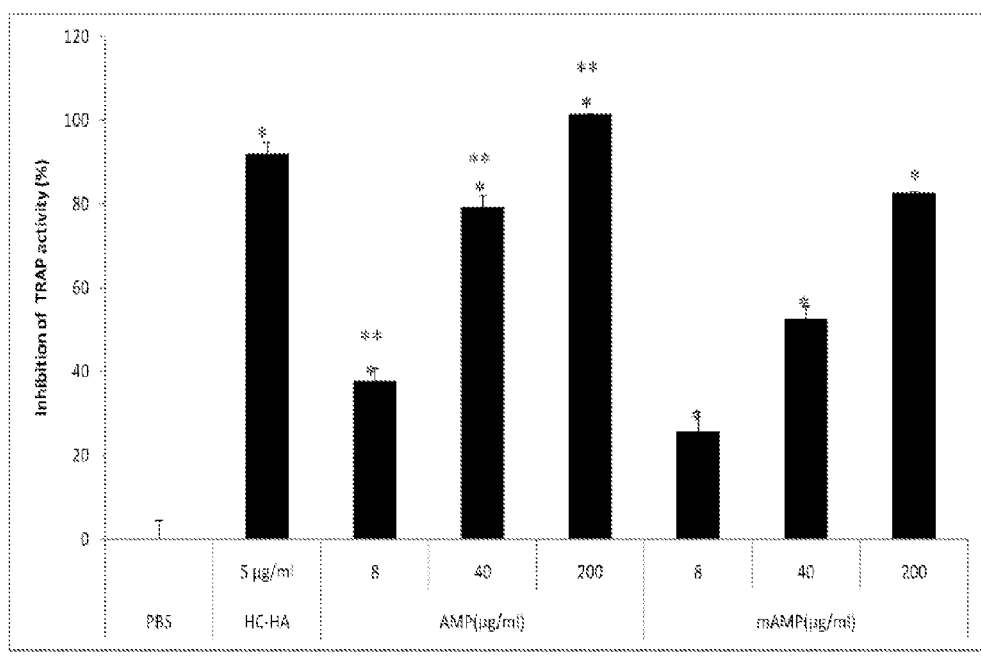
FIG. 14 exemplifies the difference in potency of cryopreserved AMP (CryoTek Method) and dehydrated AMP (Purion® Process) at inhibiting giant cell (osteoclast) formation. RAW 264.7 cells were induced to form giant cells using RANKL and then treated with cryopreserved AM powder (AMP) and dehydrated AmnioFix Injectable (mAMP). Both powders demonstrated a dose-dependent inhibition of giant cell formation, however, the inhibition was significantly more potent with the cryopreserved AMP (p>0.05).
Figure 15A:
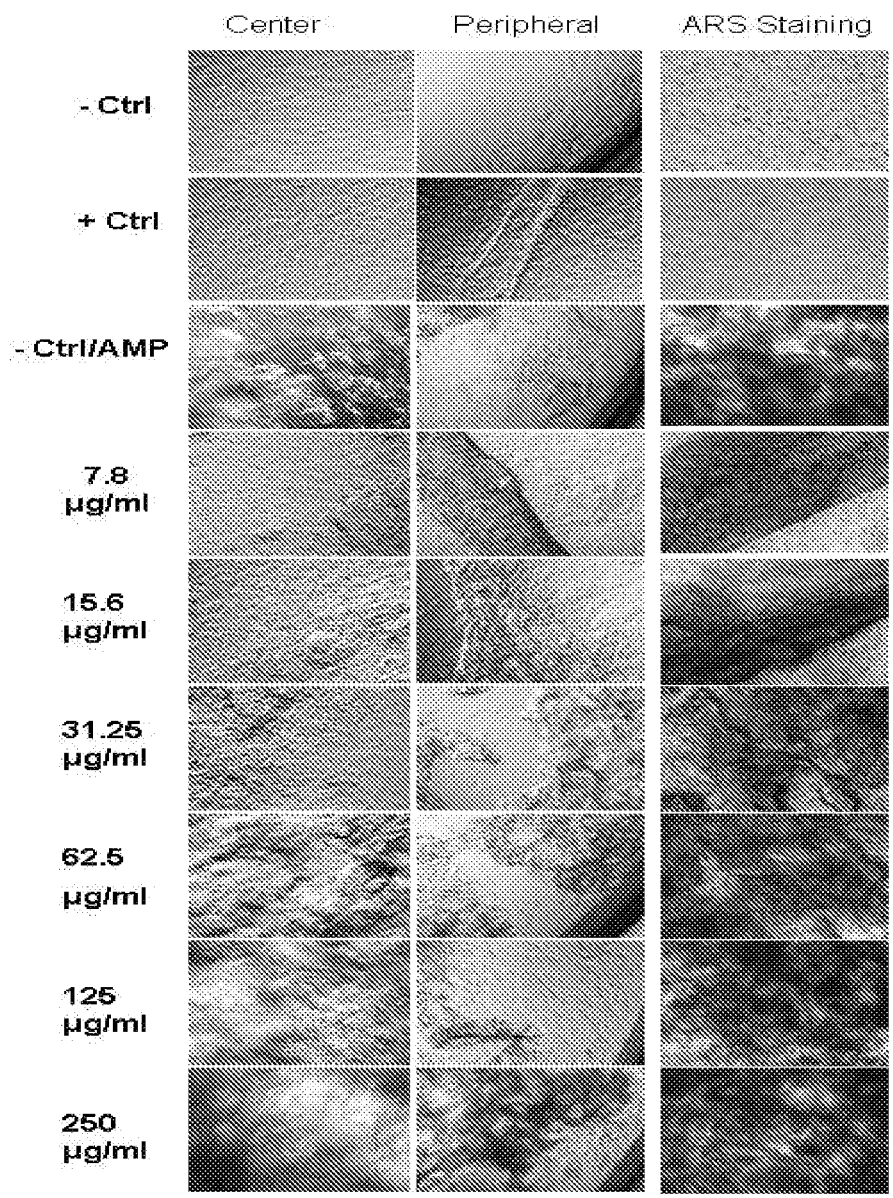
FIG. 15A. The negative control, i.e., without induction, did not develop spindle-like shapes or spindle rings throughout the entire period of culturing. The monolayer center and periphery stained a beige color. The positive control, i.e., with induction, developed fusiform and spindle-like cells and appearance of spindle rings around D5 of culturing (D4 of induction). ARS staining showed a light maroon color in the center of the monolayer. In contrast, AMP treatment from concentration 62.5 µg/ml upwards left AMP particles that settled on top of the cell monolayer and obscured observation of the monolayer. MC3T3-E1 cells treated with only AMP but no induction showed no spindle ring along the edge and ARS staining showed a dark crimson with a light pink background. From 7.8 µg/ml to 31.25 µg/ml, the AMP particles did not completely cover the monolayer and cells showed fusiform and spindle shapes. Along the edge, spindle rings could be seen. ARS staining showed a light maroon staining in the center of the monolayer and a dark crimson color along the spindle ring similar to the positive control.
Figure 15B:
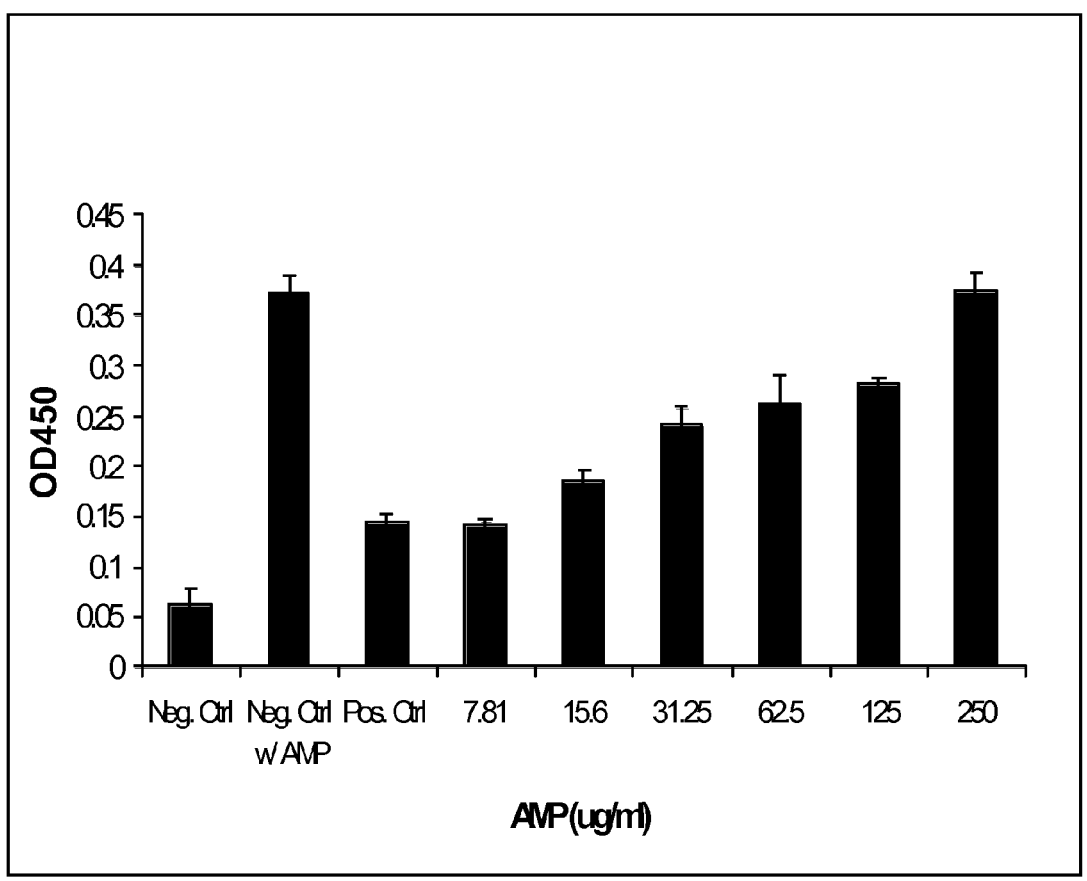
FIG. 15B. ARS staining measured after 4M GnHCl extraction and measured at $OD_{450}$ gave coefficient of variation ranging from 3% to 10%. The * symbol denotes statistical significance of p<0.05 when compared to the negative control without induction. The results showed that AMP dose-dependently promoted mineralization without inductive agents. As a matter of fact, addition of inductive agents with 250 µg/ml AMP as "the AMP negative control" was less than the same concentration with inductive agents, indicating that inductive agents dampened AMP's effect in promoting mineralization.

Treatment with AMP (125 µg/ml) yields dark staining (AMP), indicating that minerals are generated (FIG. 9).

After ARS stained cells were removed by 4 M GnCl, few cells were left in AMP treated wells (FIG. 9). Some cells migrate from the monolayer into the AMP particles and use it as a scaffold for differentiation and mineralization.

Quantitative measurement of ARS (FIG. 9) shows cells treated with AMP (125 µg/ml) significantly promote the mineralization compared to either the positive control or HC-HA (p=0.0001). The color changes related to the concentrations of alizarin red or in samples are shown in FIG. 9.

Example 35

AMP Dose-Dependently Increases Mineralization in Pre-Osteoblastic MC3T3-E1 Cells M3T3-E1 cells were seeded at $3 \times 10^4$ cells/cm$^2$/well in 96 well in αMEM medium containing 10% FBS. Upon confluence, cells were induced to differentiation by adding ascorbic acid, β-glycerolphosphate, and melatonin. After confluence (Day 0=seeding), AMP was added at 1 µg/ml, 5 µg/ml, 25 µg/ml, and 125 µg/ml (N=3 for each group), and cultured for 19 days, i.e., 18 days of induction. Cell monolayers were stained with ARS and extracted by 4M guanidine hydrochloride for 18 h; extracts were then read at 450 nm.

Figure 16A:
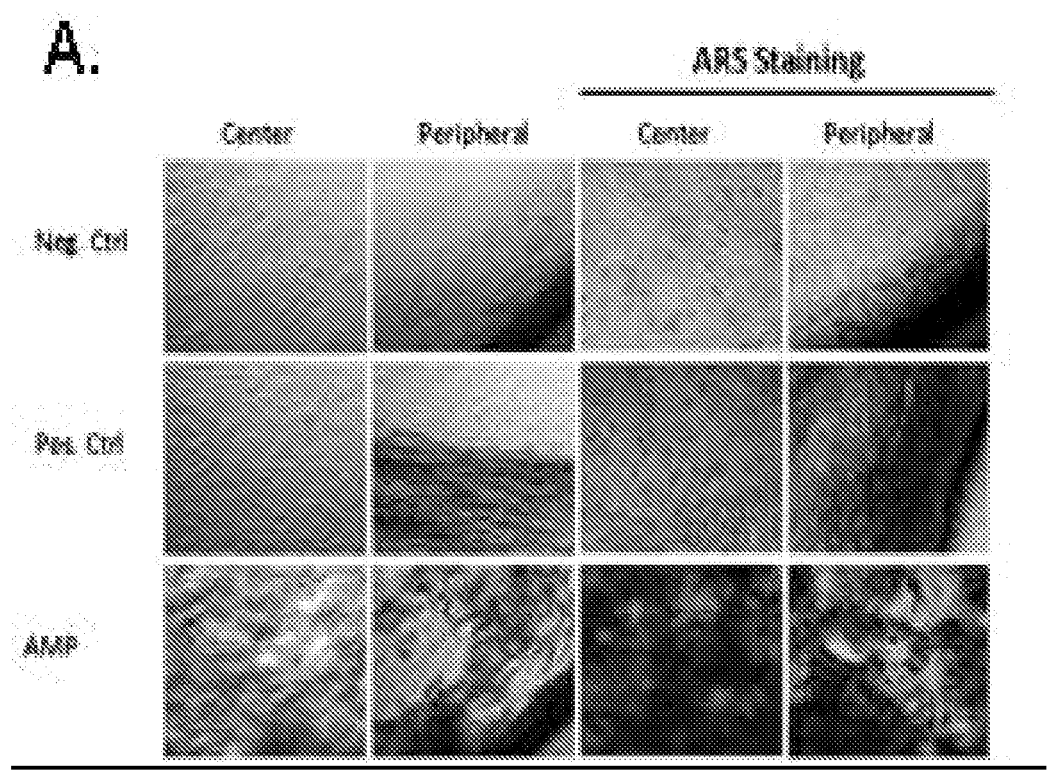
FIG. 16A. Phase contrast micrographs with or without ARS staining taken on Day 21 culturing (Day 20 of induction). Without induction medium, the negative control cells maintained a hexagonal shape with some fusiform shapes. Spindle-like shapes were not observed, and no spindle ring formed along the periphery. ARS stained the monolayer a light pink. With induction, the positive control cells attained spindle like shapes. Cell borders were more prominent and raised; a spindle ring formed along the periphery near the well edge. The monolayer center stained a maroon color, and the ARS stain concentrated in the spindle ring with an intense crimson red color. Treatment with AMP directly caused AMP particles to settle on the monolayer and obscured the morphology of the cells. However, near the culture well edge, gaps between the AMP particles showed lack of a prominent monolayer underneath in both groups. There was no difference in cell morphology between AMP treatment alone and AMP treatment with induction. The cells that were visible were spindle like in shape. No spindle ring like the positive control was observed. ARS staining showed a crimson red staining in the center with reddish-brown staining along the periphery. Staining color and patterns were indistinguishable between the induction and no-induction groups.
Figure 16B:
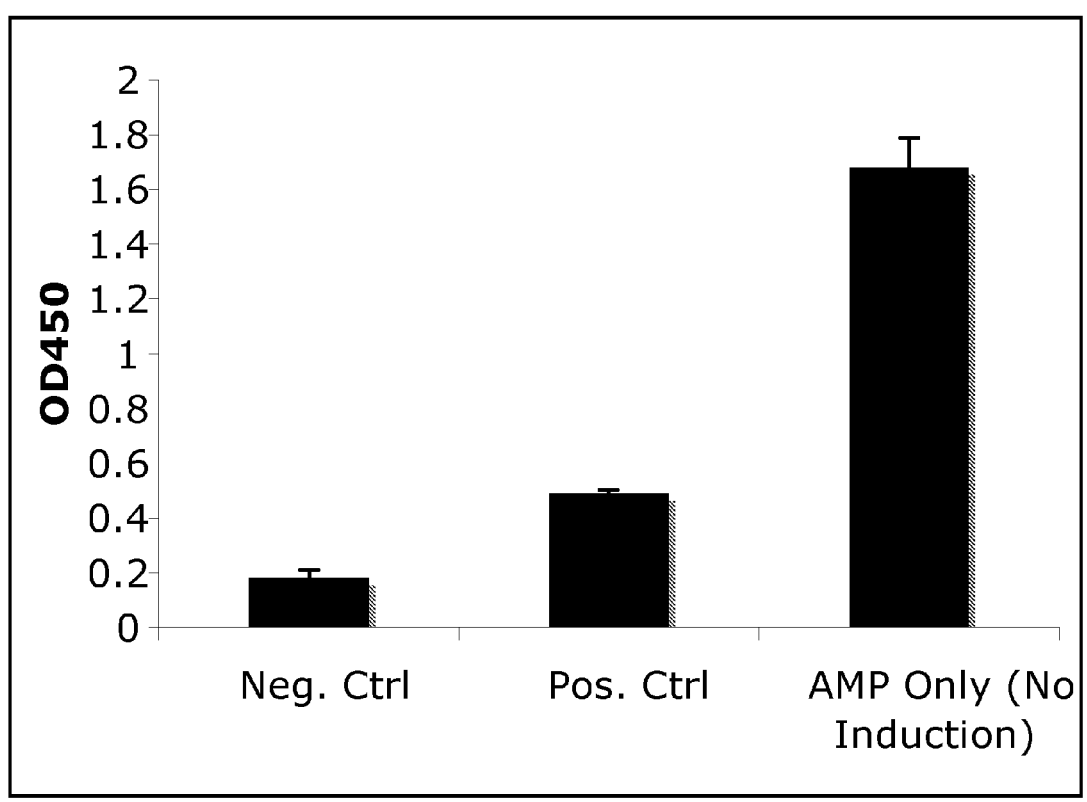
FIG. 16B. ARS staining was quantified on Day 21 of culture (Day 20 of induction). GnHCl successfully extracted the ARS dye and the coefficient of variation in $OD_{450}$ values ranged from 2% to 15%. The * symbol denotes statistical significance of p<0.05 from the positive control. This result indicated that AMP alone was more effective in promoting mineralization than the inductive agent.

Results are presented in FIGS. 16A and 16B.

Example 36

AMP Alone Induces Mineralization and Promotes More Mineralization than

Conventional Inductive Agents such as a Combination of Ascorbic Acid, β-glycerophosphate, and Melatonin.

MC3T3-E1 cells were seeded at $3 \times 10^4$ cells/cm$^2$/well in 24-well with αMEM medium plus 10% FBS. Upon confluence, cells in the positive control were induced to differentiation by adding the inductive agent containing a combination of ascorbic acid, β-glycerolphosphate, and melatonin. The AMP only group was treated with 125 µg/ml AMP, while the AMP+Induction group was added with AMP (125 µg/ml) and the above inductive agent. N=3 for each group. Cell monolayers were stained with ARS and extracted by 4M guanidine hydrochloride for 18 hours. Extracts were then read at 450 nm.

Figure 17A:
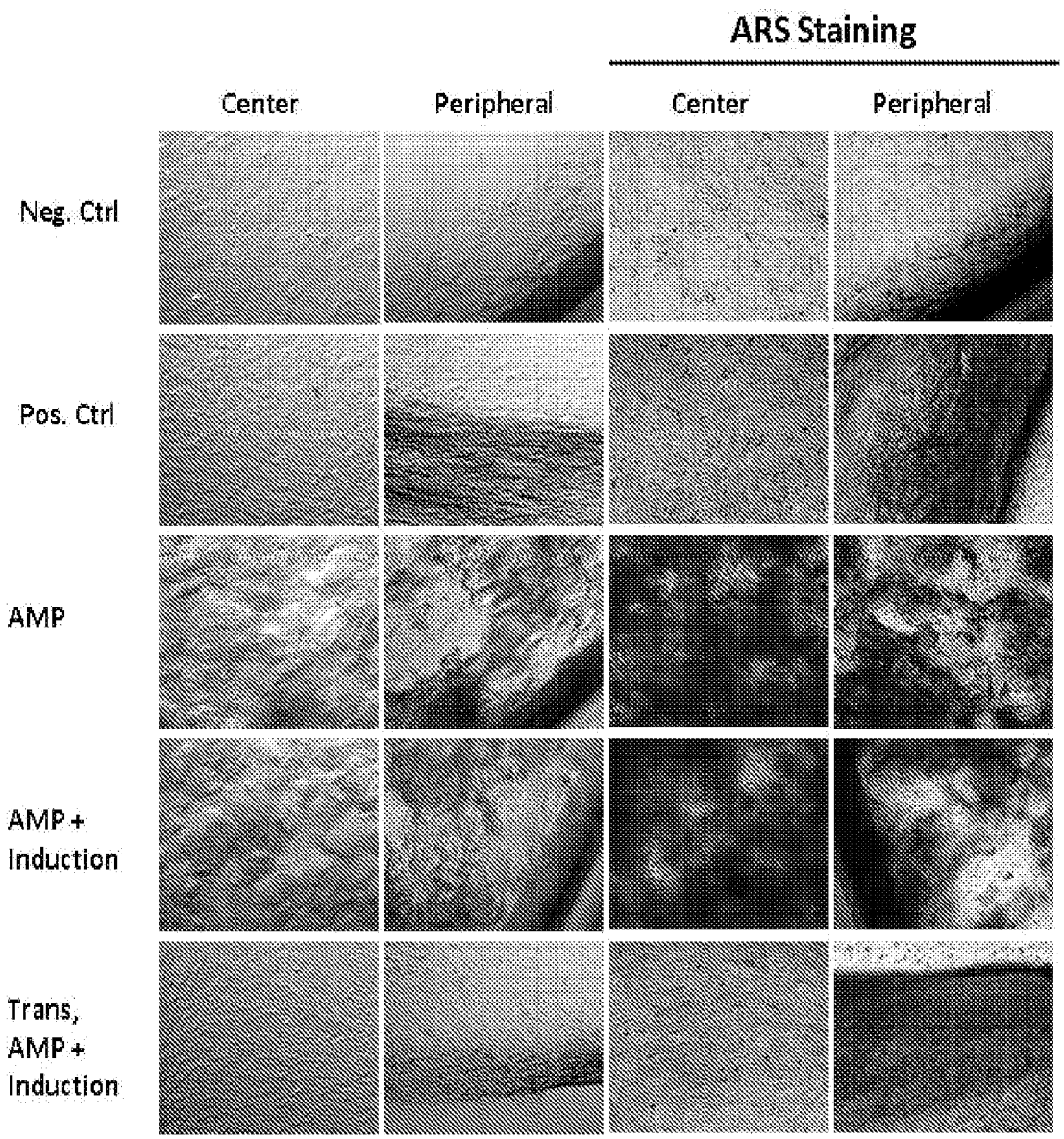
FIG. 17A. Phase contrast micrographs with or without ARS staining taken on Day 21 of culturing (Day 20 of induction). Without the induction medium, the negative control cells maintained a hexagonal shape with some fusiform shapes. Spindle-like shapes were not observed, and no spindle ring formed along the periphery. ARS stained the monolayer a light pink. With induction, the positive control cells attained spindle like shapes. Cell borders were more prominent and raised; a spindle ring formed along the periphery near the well edge. The monolayer center stained a maroon color, and the ARS stain concentrated in the spindle ring with an intense crimson red color. Treatment with AMP through a transwell (without direct contact with cells) did not produce AMP particle settlement on the monolayer. Cells were elongated and spindle-like, with spindle ring formation along the well edge. Like the positive control, the monolayer center stained a maroon color, and ARS dye concentrated in the spindle ring with an intense crimson red color.
Figure 17B:
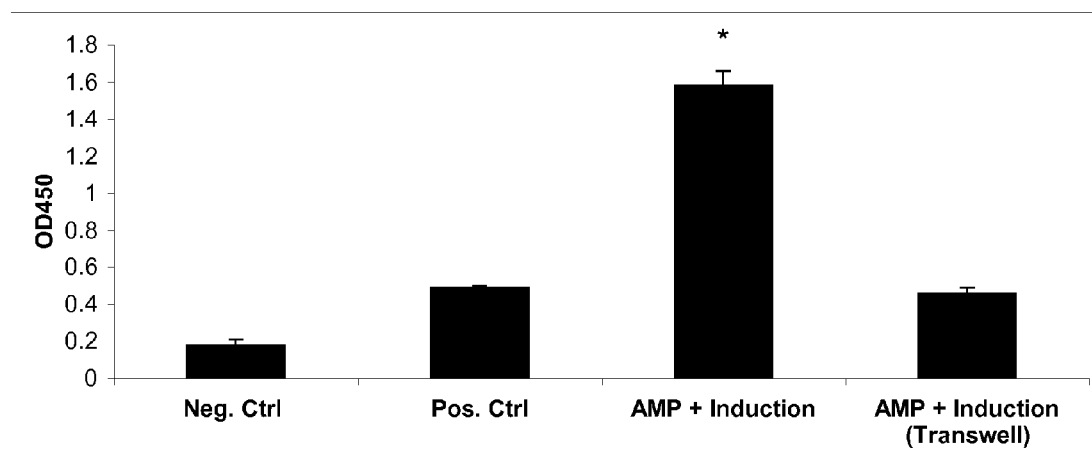
FIG. 17B. ARS staining was quantified on Day 21 of culture (Day 20 of induction). GnHCl successfully extracted the ARS dye and the coefficient of variation in $OD_{450}$ values ranged from 2% to 15%. The * symbol denotes statistical significance of p<0.05 when compared to the positive control. The results showed that AMP alone without induction caused a significant more mineralization than the positive control containing the inductive agent if AMP was in direct contact with cells, but not if AMP was not in direct contact with cells.

Results are presented in FIGS. 17A and 17B.

Example 37

AMP Requires Direct Contact with MC3T3-E1 Cells to Enhance Mineralization

MC3T3-E1 cells were seeded at $3 \times 10^4$ cells/cm$^2$/well in 24-well with αMEM medium plus 10% FBS. Upon confluence, positive control cells were induced to differentiation by adding the inductive agent containing a combination of ascorbic acid, β-glycerolphosphate, and melatonin. The AMP only group was treated with 125 µg/ml AMP, and the AMP+Induction group was treated with AMP (125 µg/ml) and the induction medium. N=3 for each group. Cell monolayers were stained with ARS and extracted with 4M guanidine hydrochloride for 18 hours. Extracts were then read at 450 nm.

Figure 18A:
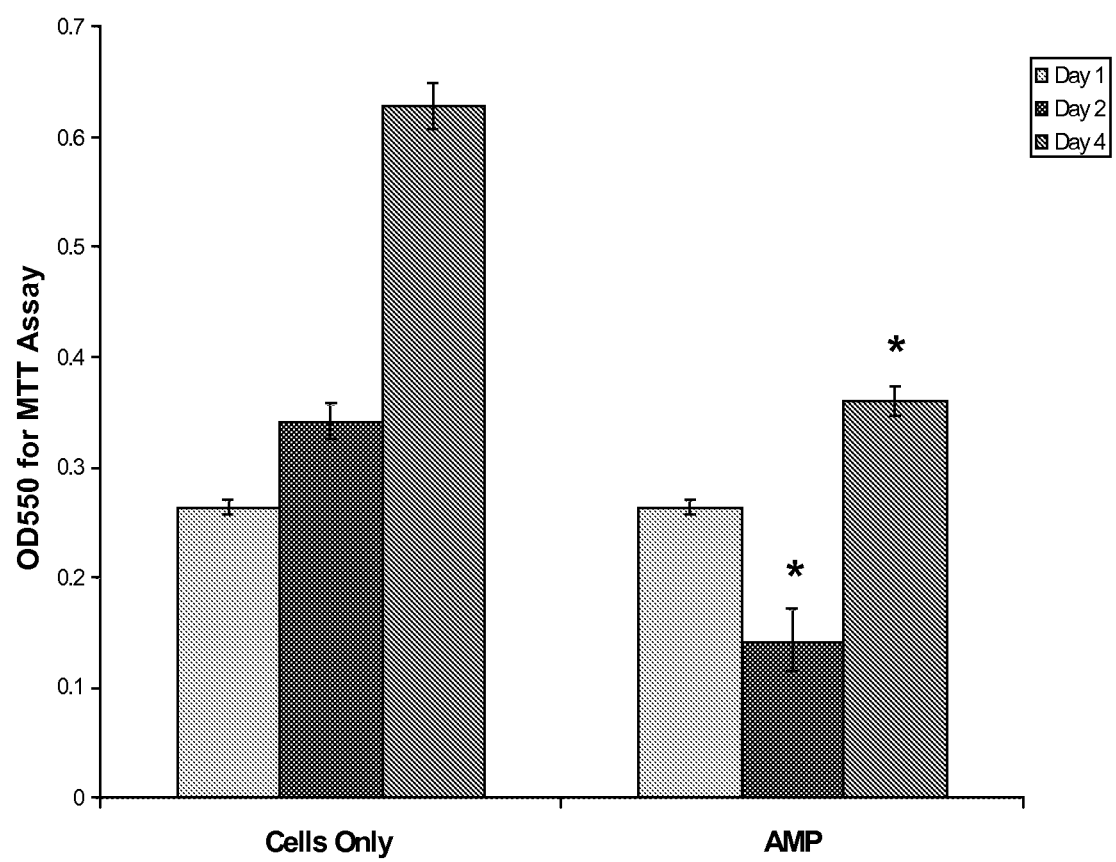
FIG. 18A. MTT Assay of MC3T3-E1 cell viability and metabolic activity on Day 1, 2, and 4. In untreated MC3T3-E1 cells, cell viability increases from Day 1 to Day 4. In AMP-treated cells, cell viability decreased on Day 2 and then more than doubled on Day 4, following the trend of the cells only group. The * symbol denotes statistical significance of p<0.05 from Day 1.
Figure 18B:
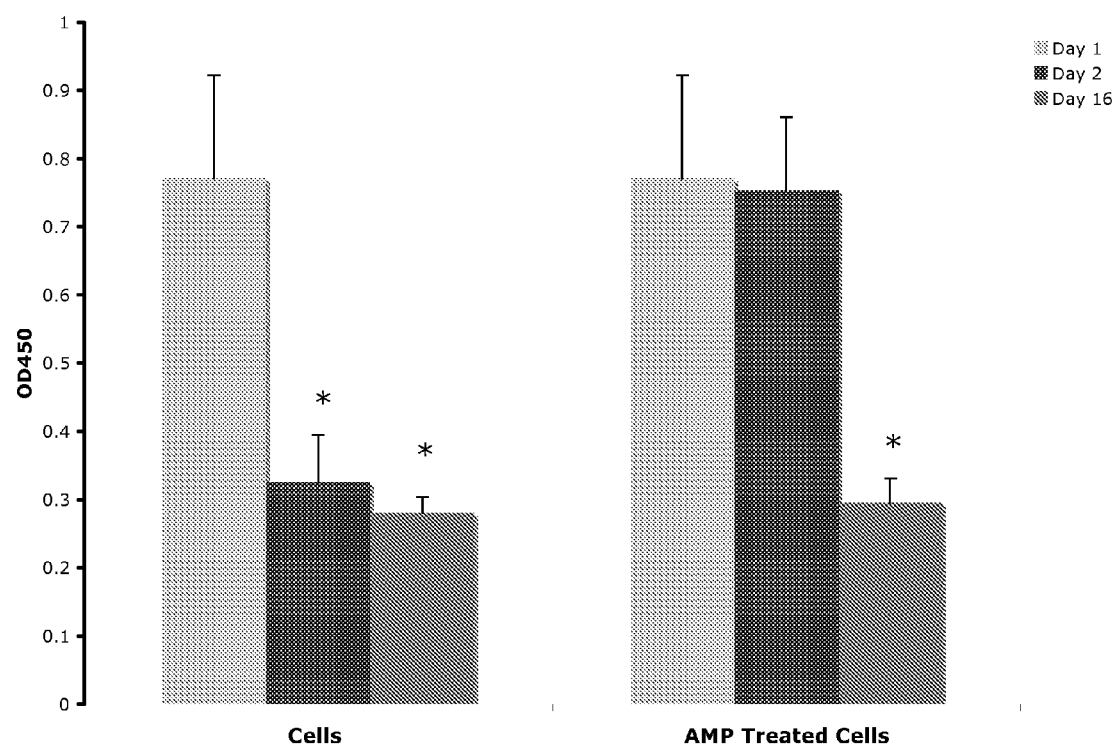
FIG. 18B. BrdU Assay of MC3T3-E1 cell proliferation on Day 1, 2, and 16. BrdU assay showed decrease in cell proliferation following Day 1 in both the cells only group and AMP-treated cell group. Cell proliferation in the cells only group decreased by more than half by Day 2 and continued to decrease on Day 16. In AMP-treated cells, cell proliferation showed a statistically significant decrease only by Day 16. The * symbol denotes statistical significance of p<0.05 from Day 1.

Results are presented in FIGS. 18A and 18B.

Example 38

AMP Treatment Does Not Increase Cell Proliferation in MC3T3-E1 Cells

To determine whether AMP promoted mineralization via promoting cell proliferation, MC3T3-E1 cells were seeded at $3 \times 10^4$ cells/cm$^2$/well in 96-well with αMEM medium plus 10% FBS. Upon confluence, the AMP group was treated with fresh 125 µg/ml AMP added every 3 days in the culture medium. The MTT assay was conducted on Day 1, 2 and 4, while the BrdU assay was conducted on Day 1, 2, and 16.

Figure 19A:
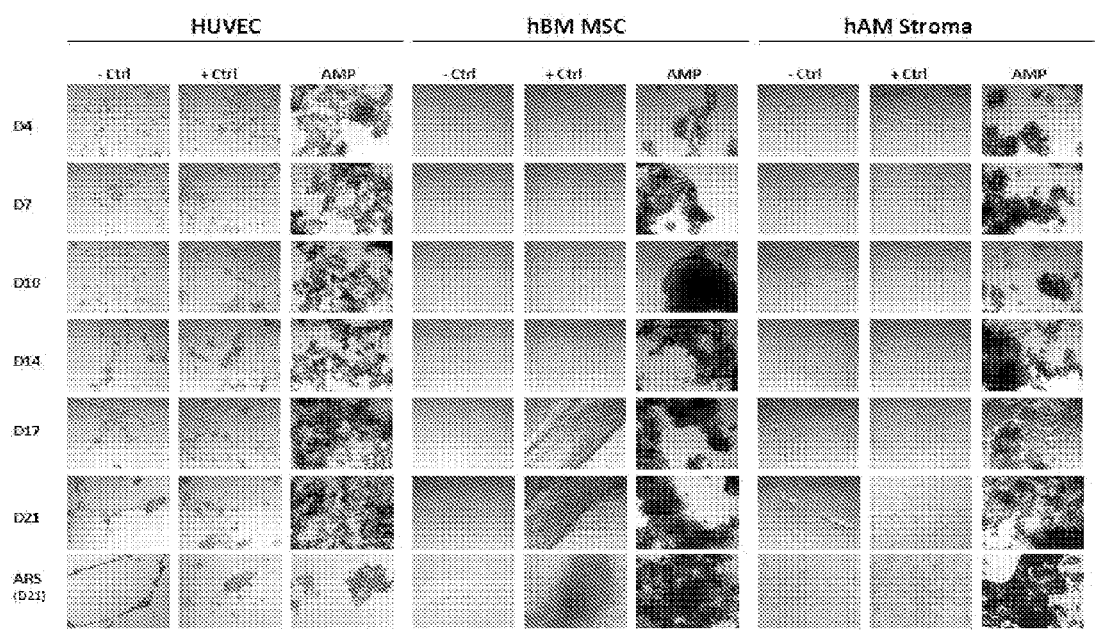
FIG. 19A. Phase contrast micrographs with or without ARS staining of HUVEC, hBMMSCs, and hAM stromal stem cells from Day 4 to Day 21. HUVEC cells formed a net-like pattern of cell growth by Day 4. However, there was significant cell death with dead cells settled on top of the network of cells until Day 21. Most of the HUVEC cells could not be fixed with 10% paraformaldehyde and the few cells stained with ARS showed a dark brown color. Although AMP settled on top of the HUVEC cells and covered the network of cells, the AMP particles detached from the plastic well with the cells upon ARS staining; the few remaining AMP particles also stained a dark brown. hBMMSCs, without induction, maintained a long fibroblastic shape. With induction, MSCs became elongated with more raised cell edges by Day 4. By Day 10, induced MSCs developed spindle-like cells, and cells grew and overlapped each other on the monolayer. On Day 17, the overlapping spindle cells formed a dense ring about 5 mm from the center of well. ARS staining showed that the uninduced MSCs monolayer stained a cream color, and the spindle ring stained a reddish orange color. AMP-treated MSCs contained AMP particles that covered the monolayer. With time, the monolayer retracted around concentrated areas of AMP particles. ARS staining showed a deep red-brown color. hAM stromal stem cells, without induction, maintained a rectangular shape. By Day 4, with induction, cell morphology changed and cells elongated with some developing fusiform shapes. AMP particles settled and covered some of the monolayer by Day 4 in AMP-treated stroma cells. The cells not covered by AMP particles in Day 4 were rectangular in shape. By Day 17, cells not covered by AMP particles were elongated like induced stroma cells in the positive control. By Day 21, AMP particles covered the well and cells morphology could not be observed. ARS staining showed the uninduced cells staining a cream color, while the induced cells stained a light pink color. The AMP-treated cells stained a deep red-brown color similar to the AMP-treated hBMMSCs.
Figure 19B:
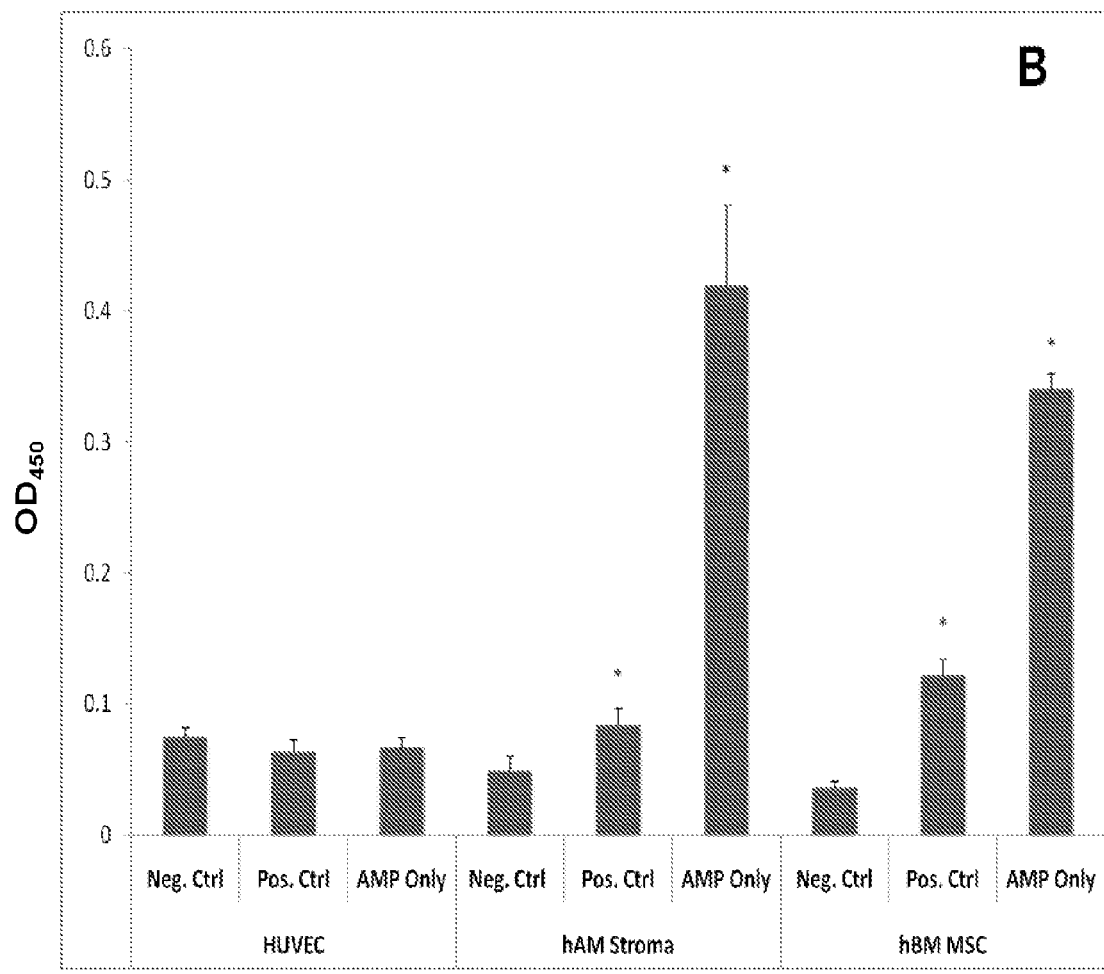
FIG. 19B. Cells were stained with ARS on Day 21 (Day 20 of induction for the positive control) and the extract with 4M GnHCl yielded the coefficient of variation in $OD_{450}$ values ranged from 2% to 15%. The * symbol denotes statistical significance of p<0.05 when compared to the negative control. No mineralization was noted in the negative control of HUVEC with either inductive agent or AMP. Nonetheless, for both hBMMSC and hAM stromal stem cells, mineralization was promoted by the inductive agent, which was less than that promoted by AMP.

Results are presented in FIGS. 19A and 19B.

Example 39

AMP Alone Can Induce Human Bone Marrow Mesenchymal Stem Cells and Human Amniotic Membrane Stromal Stem Cells to Undergo Osteogenesis and Mineralization Human Umbilical Vein Endothelial Cells serve as a negative control.

HUVEC, hBMMSCs and hAM stromal stem cells were seeded at $3 \times 10^4$ cells/cm$^2$/well in 96-well with αMEM medium plus 10% FBS. Upon confluence, the positive control groups were induced to osteoblast differentiation by adding the inductive agent containing a combination of ascorbic acid, β-glycerolphosphate, and melatonin. The AMP-treated group was treated with fresh 125 µg/ml AMP added every 3 days after confluence. Cells were stained with ARS on Day 20 and extracted by 4M guanidine hydrochloride at 37° C. for 18 hours. Extracts were then read at 450 nm.

Figure 20:
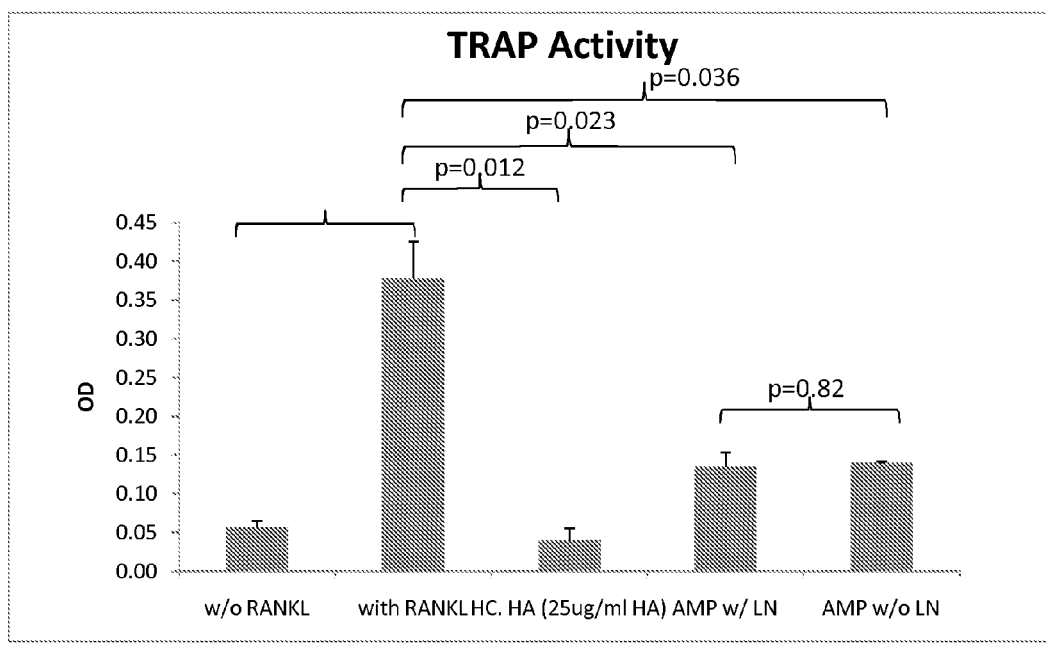
FIG. 20 exemplifies the effects of grinding AM in the presence of liquid nitrogen. TRAP activity of osteoclasts was assayed after treatment with AMP samples prepared with or w/o liquid nitrogen. At 50 µg/ml protein, AMP prepared with or w/o liquid nitrogen significantly inhibited osteoclast formation. There was no significant difference in AMP prepared with or w/o liquid nitrogen (p=0.82).

Results are presented in FIGS. 20A and 20B.

While preferred embodiments have been shown and described herein, it will be obvious to those skilled in the art that such embodiments are provided by way of example only. Numerous variations, changes, and substitutions may now occur. It should be understood that various alternatives to the embodiments described herein may be employed in practicing the described methods. It is intended that the following claims define the scope of the embodiments and that methods and structures within the scope of these claims and their equivalents be covered thereby.

What is claimed is:

1. A method of preparing a fetal support tissue powder product, consisting essentially of:
   (a) first, lyophilizing a frozen or previously frozen fetal support tissue comprising amniotic membrane, chorion, or a combination thereof to produce lyophilized fetal support tissue; and
   (b) second, grinding the lyophilized fetal support tissue to generate a fetal support tissue powder product.

2. The method of claim 1, wherein the frozen or previously frozen fetal support tissue further comprises placenta, umbilical cord, umbilical cord amniotic membrane, or any combinations thereof.

3. The method of claim 1, wherein the frozen fetal support tissue is from a fresh or previously frozen fetal support tissue.

4. The method of claim 1, wherein the fetal support tissue powder product is anti-inflammatory, anti-scarring, anti-angiogenic, anti-adhesion, or promotes wound healing.

5. The method of claim 1, further comprising cutting the frozen or previously frozen fetal support tissue into pieces prior to step (a).

6. The method of claim 1, further comprising rinsing the frozen or previously frozen fetal support tissue prior to step (a).

* * * * *